(12) United States Patent
Serreze et al.

(10) Patent No.: US 11,712,026 B2
(45) Date of Patent: Aug. 1, 2023

(54) MURINE-MHC-DEFICIENT HLA-TRANSGENIC NOD-MOUSE MODELS FOR T1D THERAPY DEVELOPMENT

(71) Applicant: The Jackson Laboratory, Bar Harbor, ME (US)

(72) Inventors: David V. Serreze, Bar Harbor, ME (US); Jeremy J. Racine, Bar Harbor, ME (US)

(73) Assignee: The Jackson Laboratory, Bar Harbor, ME (US)

( * ) Notice: Subject to any disclaimer, the term of this patent is extended or adjusted under 35 U.S.C. 154(b) by 941 days.

(21) Appl. No.: 16/163,334

(22) Filed: Oct. 17, 2018

(65) Prior Publication Data

US 2019/0110450 A1   Apr. 18, 2019

Related U.S. Application Data

(60) Provisional application No. 62/574,030, filed on Oct. 18, 2017.

(51) Int. Cl.
| | | |
|---|---|---|
| *A01K 67/027* | (2006.01) | |
| *A61K 49/00* | (2006.01) | |
| *C12N 15/85* | (2006.01) | |

(52) U.S. Cl.
CPC ...... *A01K 67/0276* (2013.01); *A61K 49/0008* (2013.01); *C12N 15/8509* (2013.01); *A01K 2217/075* (2013.01); *A01K 2227/105* (2013.01); *A01K 2267/0325* (2013.01); *A01K 2267/0362* (2013.01); *A01K 2267/0387* (2013.01); *C12N 2015/8563* (2013.01)

(58) Field of Classification Search
None
See application file for complete search history.

(56) References Cited

U.S. PATENT DOCUMENTS

| | | | |
|---|---|---|---|
| 2005/0066375 A1* | 3/2005 | Thiam | C07K 14/70539 800/8 |
| 2010/0011450 A1 | 1/2010 | Garcia et al. | |
| 2020/0060245 A1* | 2/2020 | Brehm | A01K 67/0276 |

FOREIGN PATENT DOCUMENTS

| | | |
|---|---|---|
| CN | 101022824 A | 8/2007 |
| CN | 102971420 A | 3/2013 |
| CN | 103442768 A | 12/2013 |
| CN | 104651299 A | 5/2015 |
| CN | 104812775 A | 7/2015 |
| CN | 104918483 A | 9/2015 |
| EP | 1878342 A1 | 1/2008 |
| JP | 2007-244268 A | 9/2007 |
| JP | 2009-542253 A | 12/2009 |
| WO | WO 92/11753 A1 | 7/1992 |
| WO | WO 2006/007529 A2 | 1/2006 |
| WO | WO 2008/010100 A2 | 1/2008 |
| WO | WO 2008/124142 A1 | 10/2008 |
| WO | WO 2011/130512 A1 | 10/2011 |
| WO | WO 2012/099973 A2 | 7/2012 |
| WO | WO 2014/018625 A1 | 1/2014 |
| WO | WO 2014/071397 A2 | 5/2014 |
| WO | WO 2018/102546 A1 | 6/2018 |
| WO | WO-2018209344 A1 * | 11/2018 ......... A01K 67/0276 |

OTHER PUBLICATIONS

Sellers et al. Veterinary Pathology 49(1):32-43, 2012 (Year: 2012).*
Dolatshad et al. Mammalian Genome 26:598-608, 2015 (Year: 2015).*
Ledford Nature 583:17-18, 2020 (Year: 2020).*
Schaefer et al. Nat Methods 14(4) 547-547, 2017. Author Manuscript pp. 1-3 (Year: 2017).*
Lee & Kim. Nature Biotechnology Advanced Online Publication. doi:10.1038/nbt.4207. 2018. pp. 1-2 (Year: 2018).*
Anderson and Bluestone. Annu. Rev. Immunol. 23:447-485, 2005 (Year: 2005).*
Erlich et al., HLA DR-DQ haplotypes and genotypes and type 1 diabetes risk: analysis of the type 1 diabetes genetics consortium families. Diabetes. Apr. 2008;57(4): 1084-92. doi: 10.2337/db07-1331. Epub Feb. 5, 2008.
Jarchum et al., In vivo cytotoxicity of insulin-specific CD8+ T-cells in HLA-A*0201 transgenic NOD mice. Diabetes. Oct. 2007;56(10):2551-60. Epub Jul. 9, 2007.
Johnson et al., Inhibition of autoimmune diabetes in nonobese diabetic mice by transgenic restoration of H2-E Mhc class II expression: additive, but unequal, involvement of multiple APC subtypes. J Immunol. Aug. 15, 2001;167(4):2404-10.
King, The use of animal models in diabetes research. Br J Pharmacol. Jun. 2012;166(3):877-94. doi: 10.1111/j.1476-5381.2012.01911.x.
Li et al., Identification of autoreactive CD8+ T cell responses targeting chromogranin A in humanized NOD mice and type 1 diabetes patients. Clin Immunol. Jul. 2015;159(1):63-71. doi: 10.1016/j.clim.2015.04.017. Epub May 6, 2015.
Marron et al., Functional evidence for the mediation of diabetogenic T cell responses by HLA-A2.1 MHC class I molecules through transgenic expression in NOD mice. Proc Natl Acad Sci U S A. Oct. 15, 2002;99(21):13753-8. Epub Oct. 2, 2002.
Niens et al., Prevention of "Humanized" diabetogenic CD8 T-cell responses in HLA-transgenic NOD mice by a multipeptide coupled-cell approach. Diabetes. Apr. 2011;60(4):1229-36. doi: 10.2337/db10-1523. Epub Feb. 23, 2011.

(Continued)

*Primary Examiner* — Marcia S Noble
(74) *Attorney, Agent, or Firm* — Wolf, Greenfield & Sacks, P.C.

(57) ABSTRACT

The present disclosure relates to genetically modified nonobese diabetic (NOD) mice deficient in murine class I MHC molecules, class II molecules, or both class I and class II MHC molecules. The MHC knockout transgenic mice provided herein are useful, for example, for developing therapies for diabetes.

9 Claims, 36 Drawing Sheets

Specification includes a Sequence Listing.

(56) References Cited

OTHER PUBLICATIONS

Pascolo et al., HLA-A2.1-restricted education and cytolytic activity of CD8(+) T lymphocytes from beta2 microglobulin (beta2m) HLA-A2.1 monochain transgenic H-2Db beta2m double knockout mice. J Exp Med. Jun. 16, 1997;185(12):2043-51.

Schloss et al., HLA-B*39:06 Efficiently Mediates Type 1 Diabetes in a Mouse Model Incorporating Reduced Thymic Insulin Expression. J Immunol. May 15, 2018;200(10):3353-3363. doi: 10.4049/jimmunol.1701652. Epub Apr. 9, 2018.

Serreze et al., "Humanized" HLA transgenic NOD mice to identify pancreatic beta cell autoantigens of potential clinical relevance to type 1 diabetes. Ann N Y Acad Sci. Apr. 2007;1103:103-11. Epub Mar. 21, 2007.

Serreze et al., Bridging Mice to Men: Using HLA Transgenic Mice to Enhance the Future Prediction and Prevention of Autoimmune Type 1 Diabetes in Humans. Methods Mol Biol. 2016;1438:137-51. doi: 10.1007/978-1-4939-3661-8_9.

Serreze et al., Loss of intra-islet CD20 expression may complicate efficacy of B-cell-directed type 1 diabetes therapies. Diabetes. Nov. 2011;60(11):2914-21. doi: 10.2337/db11-0705. Epub Sep. 16, 2011.

Serreze et al., Major histocompatibility complex class I-deficient NOD-B2mnull mice are diabetes and insulitis resistant. Diabetes. Mar. 1994;43(3):505-9.

Shi et al., Germ line deletion of the CD1 locus exacerbates diabetes in the NOD mouse. Proc Natl Acad Sci U S A. Jun. 5, 2001;98(12):6777-82.

Simecek et al., Genetic Analysis of Substrain Divergence in Non-Obese Diabetic (NOD) Mice. G3 (Bethesda). Mar. 3, 2015;5(5):771-5. doi: 10.1534/g3.115.017046.

Takai et al., HLA-A*0201-restricted T cells from humanized NOD mice recognize autoantigens of potential clinical relevance to type 1 diabetes. J Immunol. Mar. 1, 2006;176(5):3257-65.

Wang et al., CD 1-restricted NK T cells protect nonobese diabetic mice from developing diabetes. J Exp Med. Aug. 6, 2001;194(3):313-20.

U.S. Appl. No. 16/612,450, filed Nov. 11, 2019, Published, 2020-0060245.

International Search Report and Written Opinion dated Sep. 10, 2018 in connection with Application No. PCT/US2018/032548.

International Preliminary Report on Patentability dated Nov. 21, 2019 in connection with Application No. PCT/US2018/032548.

Ashizawa et al., Antitumor Effect of Programmed Death-1 (PD-1) Blockade in Humanized the NOG-MHC Double Knockout Mouse. Clin Cancer Res. Jan. 1, 2017;23(1):149-158. doi: 10.1158/1078-0432.CCR-16-0122. Epub Jul. 25, 2016.

Bosma et al., The mouse mutation severe combined immune deficiency (scid) is on chromosome 16. Immunogenetics. 1989;29(1):54-7.

Brehm et al., Generation of improved humanized mouse models for human infectious diseases. J Immunol Methods. Aug. 2014;410:3-17. doi: 10.1016/j.jim.2014.02.011. Epub Mar. 4, 2014.

Brehm et al., 1-NOD-scid IL2rgnull (NSG) mice deficient in murine MHC Class I and Class II expression support engraftment of functional human T cells in the absence of acute xenogeneic GVHD following injection of PBMC. AACR Annual Meeting. Apr. 18, 2018. https://www.abstractsonline.com/pp8/#!/4562/presentation/3784 [last accessed Feb. 10, 2020], Abstract only, 1pg.

Cosgrove et al., Mice lacking MHC class II molecules. Cell. Sep. 6, 1991;66(5):1051-66.

Covassin et al., Human immune system development and survival of non-obese diabetic (NOD)-scid IL2rγ(null) (NSG) mice engrafted with human thymus and autologous haematopoietic stem cells. Clin Exp Immunol. Dec. 2013;174(3):372-88. doi: 10.1111/cei.12180.

Covassin et al., Human peripheral blood CD4 T cell-engrafted non-obese diabetic-scid IL2rγ(null) H2-Ab1 (tm1Gru) Tg (human leucocyte antigen D-related 4) mice: a mouse model of; human allogeneic graft-versus-host disease. Clin Exp Immunol. Nov. 2011;166(2):269-80. doi: 10.1111/j.1365-2249.2011.04462.x.;.

Dai et al., Stress-impaired transcription factor expression and insulin secretion in transplanted human islets. J Clin Invest. May 2, 2016;126(5):1857-70. doi: 10.1172/JCI83657. Epub Apr. 11, 2016.

Ito et al., NOD/SCID/gamma(c)(null) mouse: an excellent recipient mouse model for engraftment of human cells. Blood. Nov. 1, 2002;100(9):3175-82.

King et al., Human peripheral blood leucocyte non-obese diabetic-severe combined immunodeficiency interleukin-2 receptor gamma chain gene mouse model of xenogeneic graft-versus-host-like disease and the role of host major histocompatibility complex. Clin Exp Immunol. Jul. 2009;157(1):104-18. doi: 10.1111/j.1365-2249.2009.03933.x.

Madsen et al., Mice lacking all conventional MHC class II genes. Proc Natl Acad Sci USA. Aug. 31, 1999;96(18):10338-43.

Pearson et al., Non-obese diabetic-recombination activating gene-1 (NOD-Rag1 null) interleukin (IL)-2 receptor common gamma chain (IL2r gamma null) null mice: a radioresistant model for human lymphohaematopoietic engraftment. Clin Exp Immunol. Nov. 2008;154(2):270-84. doi: 10.1111/j.1365-2249.2008.03753.x. Epub Sep. 8, 2008.

Perarnau et al., Single H2Kb, H2Db and double H2KbDb knockout mice: peripheral CD8+ T cell repertoire and anti-lymphocytic choriomeningitis virus cytolytic responses. Eur J Immunol. Apr. 1999;29(4):1243-52.

Schultz et al., Human lymphoid and myeloid cell development in NOD/LtSz-scid IL2R gamma null mice engrafted with mobilized human hemopoietic stem cells. J Immunol. May 15, 2005;174(10):6477-89.

Tong et al., Study of CAR in Multiple Myeloma Therapy. Chinese Journal of Experimental Hematology. Feb. 20, 2016:279-284.

Vugmeyster et al., Major histocompatibility complex (MHC) class I KbDb −/− deficient mice possess functional CD8+ T cells and natural killer cells. Proc Natl Acad Sci U S A. Oct. 13, 1998;95(21):12492-7.

Wang et al., Immune System Humanization of Mice. Chinese Journal of Immunology. Mar. 20, 2016:289-298.

Yaguchi et al., Human PBMC-transferred murine MHC class I/II-deficient NOG mice enable long-term evaluation of human immune responses. Cell Mol Immunol. Nov. 2018;15(11):953-962. doi: 10.1038/cmi.2017.106. Epub Nov. 20, 2017.

Yaguchi et al., MHC class I/II deficient NOG mice are useful for analysis of human T/B cell responses for humantumor immunology research. J ImmunoTher Cancer. Nov. 8-10, 2013;1(1):P39. Poster Presentation, 1pg.

Grusby et al., Depletion of CD4+ T cells in major histocompatibility complex class II-deficient mice. Science. Sep. 20, 1991;253(5026):1417-20. doi: 10.1126/science.1910207.

Pino et al., Development of novel major histocompatibility complex class I and class II-deficient NOD-SCID IL2R gamma chain knock-out mice for modeling human xenogeneic graft-versus-host disease. Methods Mol Biol. 2010;602:105-17. doi: 10.1007/978-1-60761-058-8_7. Abstract.

Beier et al., Perinatal lethality (ple): a mutation caused by integration of a transgene into distal mouse chromosome 15. Genomics. May 1989;4(4):498-504. doi: 10.1016/0888-7543(89)90272-3.

Dobie et al., Variegated transgene expression in mouse mammary gland is determined by the transgene integration locus. Proc Natl Acad Sci U S A. Jun. 25, 1996;93(13):6659-64. doi: 10.1073/pnas.93.13.6659.

Garrick et al., Repeat-induced gene silencing in mammals. Nat Genet. Jan. 1998;18(1):56-9. doi: 10.1038/ng0198-56.

Hatada et al., The influence of chromosomal location on the expression of two transgenes in mice. J Biol Chem. Jan. 8, 1999;274(2):948-55. doi: 10.1074/jbc.274.2.948.

Palmiter et al., Germ-line transformation of mice. Annu Rev Genet. 1986;20:465-99. doi: 10.1146/annurev.ge.20.120186.002341. Author Manuscript, 35 pages.

Schultz et al., Human cancer growth and therapy in NOD/SCID/IL2Rγ$^{null}$ (NSG) mice. Cold Spring Harb Protoc. Jul. 1, 2014;2014(7):694-708. doi: 10.1101/pdb.top073585. Author Manuscript, 24 pages.

\* cited by examiner

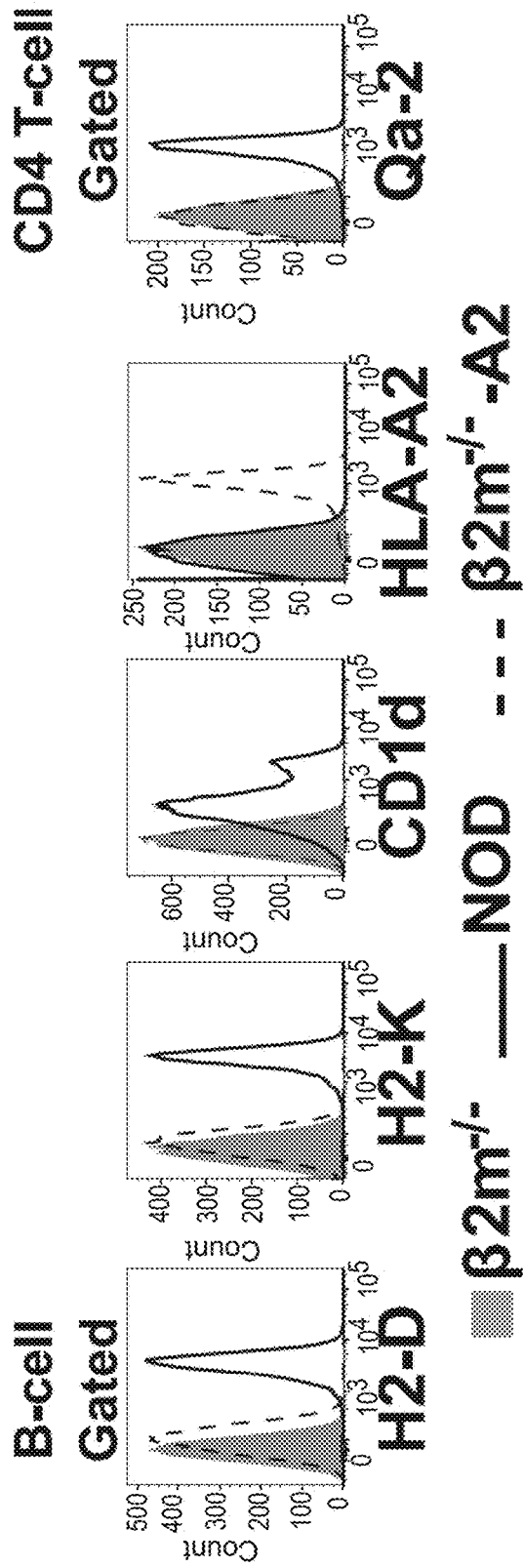
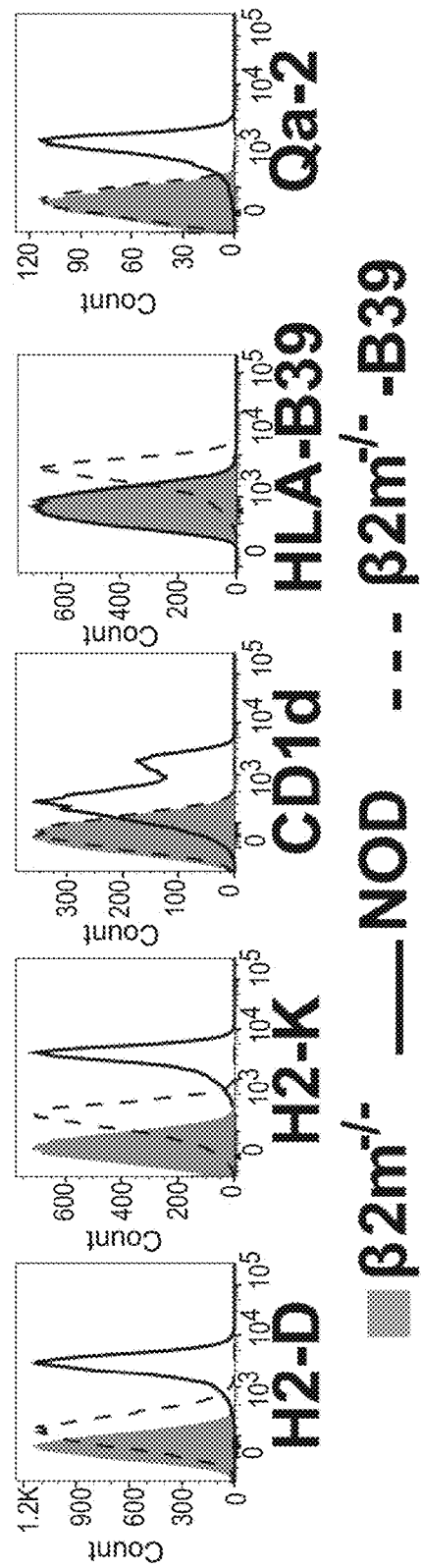
FIG. 1A
FIG. 1B

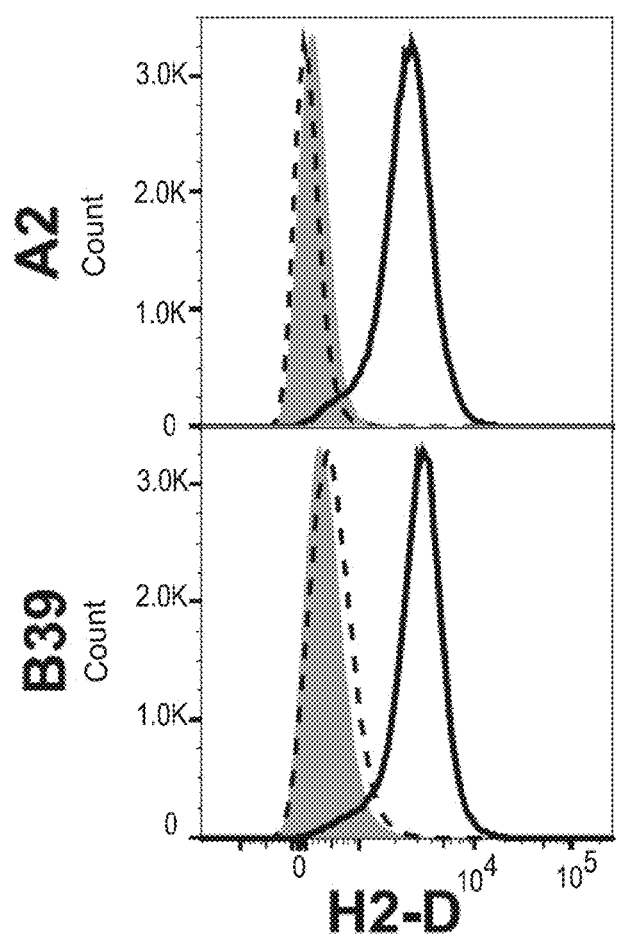 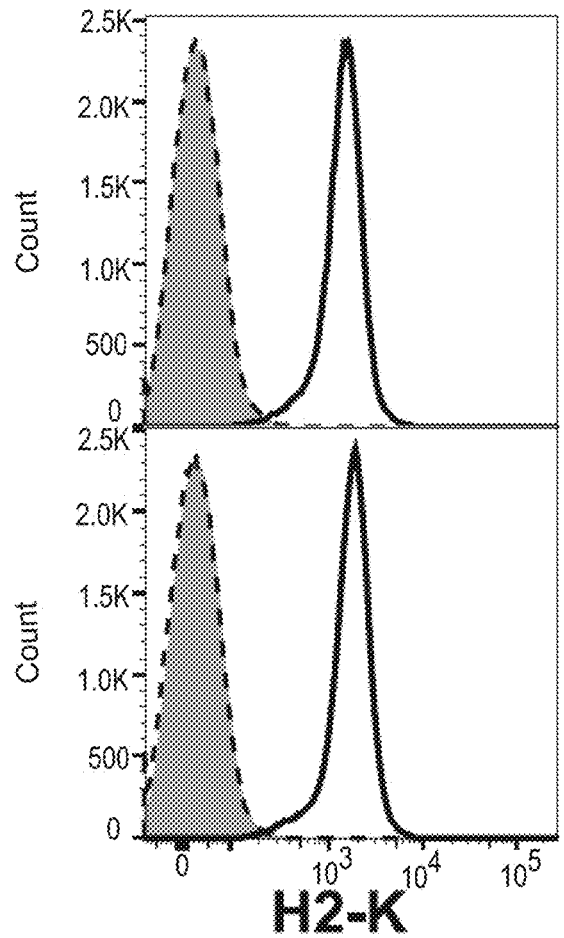
*FIG. 6C*  *FIG. 6D*

H2-Ab1<em1Dvs>

```
5' - GGCATTTCGTGCACCAGTTCAAGGGCGAGTGCTACTTCACCAACGGGACGCAGCGCATAC - 3'
     ||||||||||||||||||||||||||||||||||||||||||||||||||||||||||
5' - GGCATTTCGTGCACCAGTTCAAGGGCGAGTGCTACTTCACCAACGGGACGCAGCGC---- - 3'

5' - GGCTCGTGACCAGATACATCTACAACCGGGAGGAGTACCTGCGCTTCGACAGCGACGTGG - 3'

5' - ------------------------------------------------------------ - 3'

5' - GCGAGTACCGCGCGGTGACCGAGCTGGGGCGGCACTCAGCCGAGTACTACAATAAGCAGT - 3'

5' - ------------------------------------------------------------ - 3'

5' - ACCTGGAGCGAACGCGGGCCGAGCTGGACACGGCGTGCAGACACAACTACGAGGAGACGG - 3'
                                                             |||
5' - ---------------------------------------------------------CGG - 3'

5' - AGGTCCCCACCTCCCTGCGGCGGCTTG - 3'  SEQ ID NO: 19
     |||||||||||||||||||||||||||
5' - AGGTCCCCACCTCCCTGCGGCGGCTTG - 3'  SEQ ID NO: 20
```

*FIG. 7B*

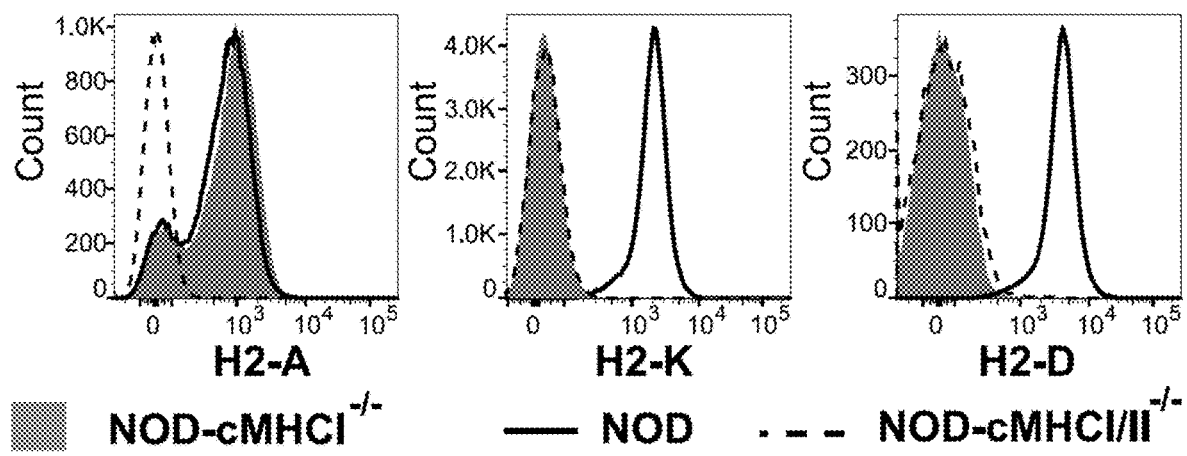

*FIG. 7C*

MURINE-MHC-DEFICIENT HLA-TRANSGENIC NOD-MOUSE MODELS FOR T1D THERAPY DEVELOPMENT

RELATED APPLICATION

This application claims the benefit under 35 U.S.C. § 119(e) of U.S. provisional application No. 62/574,030, filed Oct. 18, 2017, which is incorporated by reference herein in its entirety.

FEDERALLY SPONSORED RESEARCH

This invention was made with government support under Grant Nos. 1F32DK111078, 3-PDF-2017-372-A-N, DK-46266, DK-95735, OD-020351-5022, OD-020351-5019, R01 DK064315, DK094327, AI119225, P30 CA013330, P60 DK020541, DK103368, and T32 GM007288 awarded by National Institutes of Health. The government has certain rights in the invention.

BACKGROUND

Type 1 diabetes (T1D) is a highly polygenic autoimmune disorder in which T-cells destroy insulin producing pancreatic β-cells and involves complex interactions among developmental, genetic, and environmental factors. Non-obese diabetic (NOD) mice are used as an animal model for T1D, exhibiting a susceptibility to spontaneous development of autoimmune, T cell-mediated insulin-dependent diabetes mellitus. Diabetes develops in NOD mice as a result of insulitis, a leukocytic infiltrate of the pancreatic islets. Despite the NOD mouse contributing to our knowledge of T1D pathogenesis, it has not proved an ideal model for developing therapies with clinical efficacy.

SUMMARY

Provided herein, in some aspects are improved mouse models for developing T1D therapies. In both humans and the NOD mouse, certain major histocompatibility complex (MHC; designated HLA in humans) class I and II variants are primary genetic contributors to T1D development by respectively mediating pathogenic $CD8^+$ and $CD4^+$ T-cell responses. The first generation NOD.β2m$^{-/-}$.HHD model (NOD mice homozygous for the $β2m^{tm1Unc}$ mutation and carrying the HLA-A/H2-D/B2M transgene) expresses, in the absence of murine counterparts, the human HLA-A2.1 (also referred to as HLA-A*02:01) class I variant (belonging to the HLA-A2 allele group) linked to disease in 60% of T1D patients through an ability to support pathogenic $CD8^+$ T-cell responses.

Another strain of T1D susceptible HLA-humanized mice, NOD.β2m$^{-/-}$.B39, was also recently developed; however, because β2m (β2-microglobulin) is a critical component of the FcRn complex and IgG salvage pathways, these first generation HLA-humanized NOD mice are not appropriate for testing antibody-based therapies. The present disclosure provides, in some aspects, complete murine class I ablated NOD mice (NOD-cMHCI$^{-/-}$) as well as NOD-H2-D$^{b-/-}$ and NOD-H2-K$^{d-/-}$ mice, to separate the independent contributions of these common MHC I variants to diabetes. This NOD.MHCI$^{-/-}$ stock has been used, as provided herein, as a platform for generating improved humanized models by introducing T1D relevant HLA class I A2.1 and B39 variants. The present disclosure also provides, in some aspects a complete classical-MHC-deficient NOD stock in which H2-Ab1$^{g7}$ has also been ablated (NOD-cMHCI/II$^{-/-}$). Such a model can be utilized, for example, to introduce selected combinations of HLA class I and II genes linked to diabetes development and test potential clinical interventions tailored to specific HLA combinations.

Thus, some aspects of the present disclosure provide a genetically modified non-obese diabetic (NOD) mouse comprising a mutation in a gene encoding H2-K (e.g., H2-K1$^d$) and/or a mutation of a gene encoding H2-D (e.g., H2-D1$^b$) in the genome of the NOD mouse. In some embodiments, the genome of the NOD mouse further comprises a mutation of a gene encoding H2-A (e.g., for example, the beta chain of H2-A, i.e., H2-Ab1). A gene encoding H2-K is herein referred to as a H2-K gene. A gene encoding H2-D is herein referred to as a H2-D gene. A gene encoding H2-A is herein referred to as a H2-A gene.

Some aspects of the present disclosure provide a genetically modified non-obese diabetic (NOD) mouse comprising in the genome of the NOD mouse a homozygous mutation in H2-D1$^b$, a homozygous mutation in H2-K1$^d$, and a homozygous mutation in H2-Ab1$^{g7}$ (e.g., designated NOD/ShiLtDvs-H2-K1$^{em1Dvs}$ H2-Ab1$^{em1Dvs}$ H2-D1$^{em5Dvs}$/Dvs).

Other aspects of the present disclosure provide a genetically modified non-obese diabetic (NOD) mouse comprising in the genome of the NOD mouse a homozygous mutation in H2-D1$^b$, a homozygous mutation in H2-K1$^d$, and a human HLA-A2 transgene (e.g., designated NOD/ShiLtDvs-H2-K1$^{em1Dvs}$ H2-D1$^{em5Dvs}$ Tg(HLA-A/H2-D/B2M)1Dvs/Dvs).

Yet other aspects of the present disclosure provide a genetically modified non-obese diabetic (NOD) mouse comprising in the genome of the NOD mouse a homozygous mutation in H2-D1$^b$, a homozygous mutation in H2-K1$^d$, and a human HLA-B39 transgene (e.g., designated NOD/ShiLtDvs-H2-K1$^{em1Dvs}$ H2-D1$^{em5Dvs}$ Tg(HLA-B39/H2-D/B2M)2Dvs/Dvs).

Further, the present disclosure, in some aspects, provides methods of producing the genetically modified NOD mouse of any one of the embodiments herein using CRISPR/Cas genome editing to introduce at least one of the mutations into the genome of the NOD mouse.

Also provided herein are cells comprising a homozygous mutation in the H2-K genes and/or a homozygous mutation in the H2-D genes in the genome of the cell. In some embodiments, the cells further comprise a homozygous mutation in the H2-A genes in the genome of the cell.

The present disclosure, in other aspects, provides methods comprising administering a test agent to the genetically modified NOD mouse of any one of the embodiments herein, and assaying the genetically modified NOD mouse for a symptom of diabetes.

Additional methods comprise, in some aspects, introducing into the genome of the genetically modified NOD mouse of any one of the embodiments here a nucleic acid encoding a human MHC class I molecule and/or a nucleic acid encoding a human MHC class II molecule, and producing a humanized NOD mouse comprising a genome that expresses the human MHC class I molecule and/or expresses the human MHC class II molecule.

BRIEF DESCRIPTION OF THE DRAWINGS

FIGS. 1A-1B. HLA-humanized non-obese diabetic (NOD) mice lack classical, but not non-classical MHC I molecules. (FIGS. 1A-1B) Representative histograms showing splenic B-cell expression of H2-D, H2-K, CD1d, transgenic human HLA class I, or splenic $CD4^+$ T-cell expression of Qa-2, comparing NOD and β2m$^{-/-}$ controls to NOD.β2m$^{-/-}$-A2 (FIG. 1A) or NOD.β2m$^{-/-}$-B39 mice (FIG. 1B).

(FIG. 2A) Diagram (top) and sequence trace (bottom) showing guide sequence (bold) and PAM site within exon 2 of H2-D1$^b$ (GTACCGGGGCTCCTCGAGGC; SEQ ID NO:3) used to generated NOD-H2-D$^{-/-}$ mice (officially designated NOD/ShiLtDvs-H2-D1$^{em4Dvs}$/Dvs). The subscript nucleotide represents the H2-D1$^{em4Dvs}$ mutation that is denoted with * on the sequence trace where that nucleotide is missing. (FIG. 2B) Representative flow cytometry histogram showing expression of H2-D and H2-K antibody staining on the surface of splenic B-cells comparing 10-week-old female NOD, NOD.β2m$^{-/-}$ and NOD-H2-D$^{-/-}$ mice. (FIG. 2C) Quantification of the mean fluorescence intensity (MFI) of H2-D and H2-K antibody staining on splenic B-cells showing Mean±SEM. (FIG. 2D) Representative flow cytometry showing CD4 vs CD8 of gated CD45.1±thymocytes comparing 10-week-old female NOD and NOD-H2-D$^{-/-}$ mice. (FIGS. 2E-2F) Quantification of percentage (FIG. 2E) and yield (FIG. 2F) of CD45.1$^+$ thymic subsets showing Mean±SEM. (FIG. 2G) Representative flow cytometry showing amongst splenocytes TCRβ vs FSC-A (top) and amongst TCRβ-gated CD4 vs CD8 (bottom) from 10-week-old female mice. (FIGS. 2H-2I) Percent CD8$^+$ amongst TCRβ-gated cells (FIG. 2H) and yield (FIG. 2I) of spleen and PancLN CD4$^+$ and CD8$^+$ T-cells showing Mean±SEM. All scatter plots plot individual mice (9-16 mice per group per analysis) pooled from two to three experiments.

(FIG. 3A) Diagram (top) and sequence trace (bottom) showing guide sequence (bold) and PAM site within exon 3 of H2-K1$^d$ (TGGTGATGCAGAGTATTACA; SEQ ID NO:6) used to generate NOD-H2-K$^{-/-}$ mice (officially designated NOD/ShiLtDvs-H2-K1$^{em4Dvs}$/Dvs). The subscript nucleotides represent the H2-K1$^{em4Dvs}$ mutation that is denoted with * on the sequence trace where those nucleotides are missing. (FIG. 3B) Representative flow cytometry histogram showing expression of H2-D and H2-K on the cell surface of splenic B-cells comparing 10-15-week-old female NOD, NOD-H2-D$^{-/-}$ and NOD-H2-K$^{-/-}$ mice. (FIG. 3C) Quantification of the MFI of H2-D and H2-K antibody staining on splenic B-cells showing Mean±SEM. Individual mice are plotted and there are 7-15 mice per group combined from two experiments. (FIG. 3D) Representative flow cytometry showing CD4 vs CD8 of gated CD45.1±thymocytes comparing 10-15-week-old female NOD and NOD-H2-K$^{-/-}$ mice. (FIGS. 3E-3F) Quantification of percentage (FIG. 3E) and yield (FIG. 3F) of CD45.1±thymic subsets showing Mean±SEM, using 8-15 mice per group combined from five experiments. (FIG. 3G) Representative flow cytometry showing amongst splenocytes Thy1.2 vs FSC-A (top) and amongst Thy1.2-gated CD4 vs CD8 (bottom) from 10-week-old female mice to 15-week-old female mice. (FIGS. 3H-3I) Percent CD8$^+$ amongst Thy1.2-gated cells (FIG. 3H) and yield (FIG. 3I) of spleen and PancLN CD4$^+$ and CD8$^+$ T-cells showing Mean±SEM 8-16 mice per group combined from six experiments.

(FIG. 4A) T1D incidence curves for NOD, NOD-H2-D$^{-/-}$ and NOD-H2-K$^{-/-}$ female mice. NOD is combined from two independent cohorts of 15 and 16 mice respectively. (FIG. 4B) Mean insulitis score of 10-week-old mice to 15-week-old mice. (FIG. 4C) Mean insulitis score of mice after 30 weeks of age, with diabetics automatically receiving a score of 4. (FIG. 4D) Representative flow cytometry of NOD, NOD-H2-D$^{-/-}$, and NOD-H2-K$^{-/-}$ showing Thy1.2 amongst islet-infiltrating cells (top), CD4 vs CD8 amongst gated T-cells (middle), and CD44 vs CD62L amongst gated islet CD8$^+$ T-cells (bottom). (FIGS. 4E-4F) Quantification of percent Thy1.2k amongst islet infiltrating cells (FIG. 4E), CD4 and CD8 amongst islet Thy1.2±cells (FIG. 4F) and percent CD44$^+$CD62L$^-$ effector, CD44$^-$CD62L$^+$ naïve, and CD44$^+$CD62L$^+$ central memory CD8$^+$ T-cells (FIG. 4G) showing NOD vs NOD-H2-D$^{-/-}$ vs NOD-H2-K$^{-/-}$ mice. NOD-H2-K$^{-/-}$ data includes 8 mice from the other two NOD-H2-K$^{-/-}$ lines described in FIGS. 8A-8C.

(FIG. 5A) Diagram and sequencing traces showing location of guides and mutations in exon 2 of H2-D1$^b$ (top) (GTACATCTCTGTCGGCTATG; SEQ ID NO:9) and H2-K1$^d$ (bottom) (ATAATCCGAGATTTGAGCCG; SEQ ID NO:12). Guide sequence is bold, mutations are marked by subscripted nucleotides, and marked on the sequencing trace with a *. Strain officially designated NOD/ShiLtDvs-H2-K1$^{em1Dvs}$ H2-D1$^{em5Dvs}$/Dvs. (FIG. 5B) Representative flow cytometry histogram (top) showing expression of H2-D and H2-K on the surface of splenic B-cells comparing 10-week-old female NOD, NOD.β2m$^{-/-}$ and NOD-cMHCI$^{-/-}$ mice. Quantification of the MFI of H2-D and H2-K antibody staining on splenic B-cells showing Mean±SEM (bottom). Individual mice are plotted and are combined from two independent experiments. There are 5-10 mice per group combined from two experiments. (FIG. 5C) Representative flow cytometry showing amongst splenocytes TCRβ vs FSC-A (top) and amongst TCRβ-gated CD4 vs CD8 (bottom) from 10-week-old female mice. (FIG. 5D) Yield of splenic CD4$^+$ and CD8$^+$ T-cells showing Mean±SEM, 5-23 mice per group combined from five experiments. (FIG. 5E) T1D incidence comparing NOD, NOD-cMHCI$^{-/-}$ and NOD.β2m$^{-/-}$ female mice. (FIG. 5F) Mean insulitis score at end of incidence showing 9-15 mice per group, with diabetic mice receiving a score of 4.

FIGS. 6A-6M. Novel NOD-cMHCI$^{-/-}$-HLA mice retain non-classical MHCI, NKT-cells and FcRn functionality. A2 or B39 expressing transgenes were crossed into NOD-cMHCI$^{-/-}$ mice to generate the NOD-cMHCI$^{-/-}$-A2 (official designation NOD/ShiLtDvs-H2-K1$^{em1Dvs}$ H2-D1$^{em5Dvs}$ Tg(HLA-A/H2-D/B2M)1Dvs/Dvs) and NOD-cMHCI$^{-/-}$-B39 stocks (official designation NOD/ShiLtDvs-H2-K1$^{em1Dvs}$ H2-D1$^{em5Dvs}$ Tg(HLA-B39/H2-D/B2M)2Dvs/Dvs). (FIGS. 6A-6B) Representative spleen flow cytometry of gated TCRβ$^+$ cells showing a comparison of CD4 vs CD8 T-cell subset levels in NOD-cMHCI$^{-/-}$-A2 (FIG. 6A) or NOD-cMHCI$^{-/-}$-B39 (FIG. 6B) to NOD and NOD-cMHCI$^{-/-}$ mice. Data is representative of at least 10 mice per group examined from 8-20 weeks of age across three separate experiments. (FIGS. 6C-6F) Representative histograms showing H2-D (FIG. 6C), H2-K (FIG. 6D), HLA class I (FIG. 6E), and CD1d (FIG. 6F) expression on gated splenic B-cells from NOD (solid line), NOD-cMHCI$^{-/-}$-HLA-A2 or HLA-B39 (dashed line), and NOD.β2m$^{-/-}$-HLA (shaded FIGS. 6C, 6F) or NOD.β2m$^{-/-}$ (shaded FIGS. 6D-6E) mice. (FIG. 6G) Representative histograms showing Qa-2 expression on gated splenic CD4$^+$ T-cells from NOD (solid line), NOD.β2m$^{-/-}$-HLA (shaded line), and NOD-cMHCI$^{-/-}$-HLA (dashed line) mice. (FIGS. 6H-6I) Representative flow cytometry showing staining of gated splenic TCRβ$^+$ cells with a CD1d-α-GalCer tetramer vs FSC-A comparing NOD, NOD.β2m$^{-/-}$-A2 and NOD-cMHCI$^{-/-}$-A2 (FIG. 6H) or NOD.β2m$^{-/-}$-B39 and NOD-cMHCI$^{-/-}$-B39 (FIG. 6I). (FIG. 6J) T1D incidence and end of incidence survivor insulitis (FIG. 6K) for female NOD-cMHCI$^{-/-}$-A2 and NOD-cMHCI$^{-/-}$-B39 mice. (FIGS. 6L-6M) NOD, NOD.β2m$^{-/-}$-A2, and NOD-cMHCI$^{-/-}$-A2 mice were injected on Day 0 with mouse IgG1 (1B7.11) (FIG. 6L) and humanized IgG1 (Herceptin) (FIG. 6M) at 10 mg/kg and 5 mg/kg (0.1 ml/20 g body weight) respectively. Blood was obtained on days 1, 2, 3, 5, 7, 14, 21, and 28 after injection. Plasma was frozen at −20° C. until the end of the study. Data is plotted as Mean±SEM of remaining antibody detectable in the blood. Data for NOD.β2m$^{-/-}$-A2 mice on days 14, 21, 28 (1B7.11) and day 3, 5, 7, 14, 21, 28 (Herceptin) were below the detection limit of the ELISA. There were 8-10 mice per group per time point.

FIGS. 7A-7J. Novel direct-in-NOD-cMHCI/II$^{-/-}$ mice. (FIG. 7A) Diagram showing sgRNA guide (bold) and PAM sites within exon 2 of H2-Ab1$^{g7}$ (CCAACGGGACGCAGCGCATA (SEQ ID NO:15); CGACGTGGGCGAGTACCGCG (SEQ ID NO:16); CGAAGCGCAGGTACTCCTCC (SEQ ID NO: 17); ACACAACTACGAGGAGACGG (SEQ ID NO:18). (FIG. 7B) Alignment diagram showing location of a 181 base pair (bp) deletion within exon 2 of H2-Ab1 with guide sites listed in bold. Resultant NOD-cMHCI/II$^{-/-}$ mice officially designated NOD/ShiLtDvs-H2-K1$^{em1Dvs}$ H2-Ab1$^{em1Dvs}$ H2-D1$^{em5Dvs}$/Dvs. (FIG. 7C) Representative flow cytometry panels showing H2-A, H2-K, and H2-D expression on gated splenic B-cells. (FIG. 7D) Quantification of MFI antibody staining for each MHC comparing NOD and NOD-cMHCI/II$^{-/-}$ mice. (FIG. 7E) Representative flow cytometry panel showing percent Thy1.2k amongst splenocytes. (FIG. 7F) Quantification of % Thy1.2±cells comparing NOD, NOD-cMHCI$^{-/-}$ and NOD-cMHCI/II$^{-/-}$ mice. Data is combined from two experiments showing 9-10 female mice per group at 9-12 weeks of age. (FIG. 7G) Representative flow cytometry panel showing percent TCRγδ vs TCRβ amongst Thy1.2±cells. (FIG. 7H) Quantification of % TCRαβ vs TCRγδ comparing NOD, NOD-cMHCI$^{-/-}$ and NOD-cMHCI/II$^{-/-}$ mice. (FIG. 7I) Quantification of the yield of CD4$^{++}$ (CD1d-α-GalCer$^-$), CD8$^+$, NKT (CD4$^+$ and CD4$^-$ CD1d-α-GalCer$^+$) and CD4$^-$ CD8$^-$ Thy1.2$^+$ TCRβ$^+$ T-cells. (FIG. 7J) Mean insulitis score at 9-12 weeks of age comparing NOD and NOD-cMHCI/II$^{-/-}$ mice.

(FIG. 8A) Grey lines show NOD-H2-D$^{em4Dvs}$ and one of the two cohorts of NOD presented in FIG. 4. Founder KZ00009 carried an 11 bp deletion and generated NOD/ShiLtDvs-H2-D1$^{em1Dvs}$/Dvs a line that was run through complete diabetes incidence but is now extinct. Founder KZ00007 carried a 2 bp deletion in exon 2 and generated NOD/ShiLtDvs-H2-D1$^{em3Dvs}$/Dvs mice. Founder KZ00041 carried a 16 bp deletion within exon 2 and was backcrossed to NOD for a 2$^{nd}$ time before intercrossing to generate NOD/ShiLtDvs-H2-D1$^{em2Dvs}$/Dvs mice. Mutations em3Dvs and em2Dvs have been frozen as sperm. For Batch 1 PCR primers described in methods, PCR conditions using DreamTaq polymerase were as follows: 0.6 µM each primer, 1.5× PCRx Enhancer, 0.4 mM dNTPs. 95° 45s, 67.5° 45s, 72° 45s, for 35 cycles. Batch 2 PCR cycles were as follows: 95° 30s, 61° 30s, 72° 45s, for 35 cycles. (FIG. 8B) Founder LK00086 was crossed to NOD and two separate mutations in exon 3 were identified a 1 bp (FIG. 8C) insertion (NOD/ShiLtDvs-H2-K1$^{em5Dvs}$/Dvs) and 1 bp deletion (NOD/ShiLtDvs-H2-K1$^{em6Dvs}$/Dvs). Heterozygous pups carrying the em5Dvs mutation were intercrossed and homozygosity was determined by flow cytometry. A single mouse carrying the em6Dvs mutation was backcrossed to NOD for a 2$^{nd}$ generation. Heterozygous pups were then crossed to fix for homozygosity but has not been further analyzed. Founder LK00095 was derived from a 2$^{nd}$ guide targeting H2-K1 (GTATTACAGGGCCTACCTAG) (SEQ ID NO:21) and was crossed to NOD, and a single bp (T) insertion being identified in exon 3 (NOD/ShiLtDvs-H2-K1$^{em7Dvs}$/Dvs). Homozygosity was fixed as previously described. All lines have been frozen as sperm. For H2-K1 primers described in the methods, PCR conditions using DreamTaq polymerase were as follows: 0.8 µM each primer, 1× PCRx Enhancer, 0.4 mM dNTPs. 95° 30s, 60° 30s, 72° 45s, for 35 cycles. (FIG. 8C) Founder LM00014 generated NOD/ShiLtDvs-H2-K1$^{em2Dvs}$ H2-D1$^{em6Dvs}$/Dvs, a line carrying a 1 bp insertion within exon 2 of H2-D1 paired with an 8 bp deletion and 4 bp insertion within exon 2 of H2-K1. Founder LM00035 was generated with a different guide for H2-D1 (AG-ATGTACCGGGGCTCCTCG) (SEQ ID NO:22) paired with the aforementioned H2-K1 guide. A single line carrying a 10 bp deletion within exon 2 of H2-D1 paired with a 2 bp deletion within exon 2 of H2-K1 was generated. A heterozygous pup was backcrossed to NOD for a 2$^{nd}$ generation. Pups from this cross were then intercrossed to generate NOD/ShiLtDvs-H2-K1$^{em3Dvs}$ H2-D1$^{em7Dvs}$/Dvs. The two lines carrying H2-K1$^{em2Dvs}$ H2-D1$^{em6Dvs}$ and H2-K1$^{em3Dvs}$ H2-D1$^{em7Dvs}$ have been frozen as sperm. PCR conditions for H2-D1 were performed as in FIG. 8A. For H2-K1 primers described for NOD-cMHCI$^{-/-}$ mice in methods, PCR conditions using DreamTaq polymerase were as follows: 0.6 µM each primer, 1.5× PCRx Enhancer, 0.4 mM dNTPs. 95° 30s, 61° 30s, 72° 45s, for 35 cycles.

(FIG. 11A) Representative flow cytometry showing CD4 vs CD8 amongst splenic Thy1.2$^+$ TCRαβ cells in NOD, NOD-cMHCI$^{-/-}$ and NOD-cMHCI/II$^{-/-}$ mice. (FIG. 11B) Representative flow cytometry showing CD4 vs CD1d-α-GalCer amongst splenic Thy1.2$^+$ TCRαβ$^+$ cells in NOD, NOD-cMHCI$^{-/-}$ and NOD-cMHCI/II$^{-/-}$ mice. For PCR primers described in the methods, PCR conditions using Platinum SuperFi Taq were as follows: 0.6 µM each primer, 1× SuperFi GC Enhancer, 0.4 mM dNTPs. 98° 10s, 68.7° 10s, 72° 15s, for 40 cycles.

DETAILED DESCRIPTION

Figure 2A:
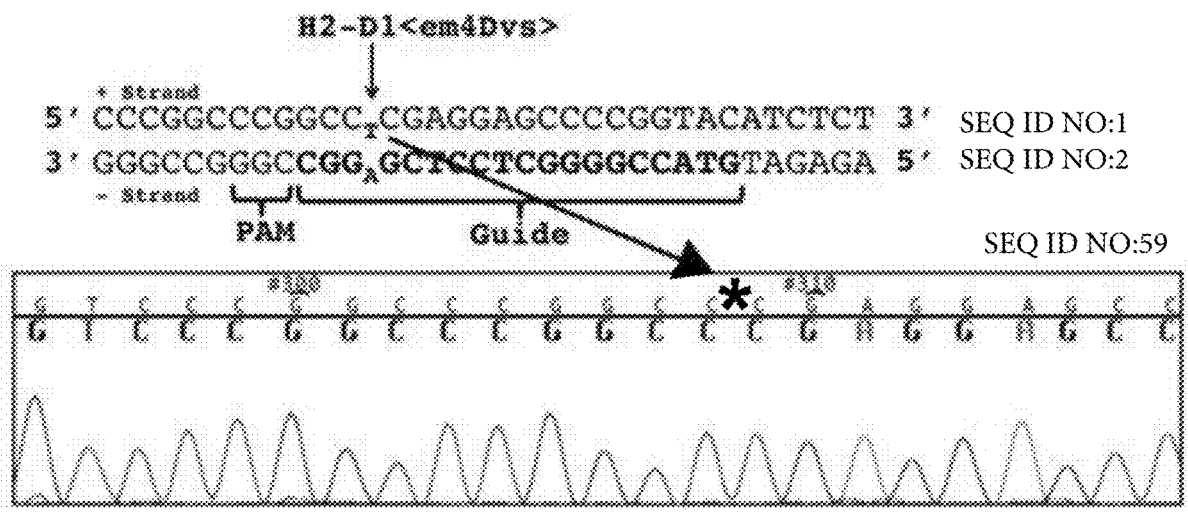
FIGS. 2A-2I. Novel, direct-in-NOD H2-D knockout mouse generated with CRISPR/Cas9.

Non-obese diabetic (NOD) mice have greatly advanced knowledge of the genetics and pathogenic mechanisms underlying autoimmune mediated type 1 diabetes (T1D) (1). However, NOD mice have been less successful as a model for translating this knowledge into clinically applicable therapies (2). A potential way to improve NOD as a preclinical platform is to "humanize" the strain with a variety of genes relevant to T1D patients (3; 4). A desired humanization process would turn an inbred mouse potentially representing one T1D patient profile, into a multiplex platform capable of representing an array of such individuals. Such pipeline models could be used to test therapies with potential efficacy in heterogeneous at-risk T1D subjects.

While polygenic in nature, specific major histocompatibility complex (MHC, designated HLA in humans) haplotypes provide the strongest T1D risk factor (5; 6). Hence, a flexible panel of HLA-"humanized" NOD mice may provide improved models for testing potentially clinically applicable T1D interventions. In humans, particular HLA class II variants such as DQ8 and DR3/4 mediating autoreactive $CD4^+$ T-cell responses strongly contribute to T1D susceptibility (7-9). Similarly, the murine $H2-A^{g7}$ class II variant, highly homologous with the human DQ8 molecule, is a primary T1D contributor in NOD mice (10). However, findings that NOD mice made deficient in MHC class I expression and $CD8^+$ T-cells by introduction of an inactivated $\beta 2m$ allele (NOD.$\beta 2m^{-/-}$) are completely T1D resistant (11) indicated this immunological arm is also critical to disease development. It was subsequently found that particular HLA class I variants also contribute to T1D susceptibility in patients (12-16). Thus, a desirable pipeline model system would enable generation of NOD mice expressing chosen combinations of human T1D associated HLA class I and II variants in the absence of their murine counterparts that could then serve to test potential clinically relevant disease interventions.

T1D associated class I susceptibility variants in humans include HLA-A*02:01 (hereafter HLA-A2.1) and HLA-B*39:06 (hereafter B39) (12-19). HLA-A2 is in strong linkage disequilibrium with the DR4/DQ8 class II haplotype, the primary contributor to T1D development in Caucasians (14). Hence, the A2 class I variant will be present in the preponderance of T1D patients. While representing a relatively low frequency allele, the B39 variant supports aggressive early age of onset T1D development (15; 16). The original HHD transgene construct contains the genomic promoter and first three exons of HLA-A*02:01, encoding the antigen presenting α1 and α2 domains, and a covalently linked human β2m with the α3, transmembrane, and cytoplasmic domains of murine $H2-D^b$ origin allowing for proper signaling within mice (20). When introduced into normally disease-resistant NOD.$\beta 2m^{-/-}$ mice, HHD transgene expression of HLA-A2.1 in the absence of any murine class I molecules restored the generation of pathogenic $CD8^+$ T-cells mediating insulitis and T1D development (21). These mice allowed identification of HLA-A2.1 restricted autoantigenic epitopes derived from the pancreatic β-cell proteins insulin and IGRP (21-23) also targeted by $CD8^+$ T-cells from human patients expressing this class I variant (24-29). This subsequently led to development of some proof-of-principle antigen-specific therapeutics (30). The B39 variant appears to be a highly potent human T1D contributory class I molecule particularly in terms of promoting early age disease onset (12; 17-19). Introduction of a modified HHD transgene-cassette, in the absence of murine class I molecules, induced expression of the α1 and α2 domains of B39, rather than A2 with the rest of the construct remaining as originally described (20), also restored generation of T1D inducing $CD8^+$ T-cells in NOD.$\beta 2m^{-/-}$ mice (31). These findings illustrate the potential of having patient-derived models for testing possible T1D therapies.

The first-generation HLA-A2 and HLA-B39 transgenics required pairing with the $\beta 2m^{-/-}$ mutation to eliminate murine MHC I expression. While $\beta 2m^{-/-}$ mice lack expression of the classical murine H2-D and H2-K MHC class I molecules, this mutation additionally ablates non-classical MHC molecules such as CD1d and Qa-2, potentially altering immune processes. $\beta 2m^{-/-}$ mice also lack expression of FcRn, a non-classical MHC I molecule critical for serum IgG and albumin homeostasis pathways including processing and presentation of IgG complexed antigens to T-cells (32-35). Hence, $\beta 2m^{-/-}$ NOD mouse models are unsuited for investigating potential antibody-based or serum albumin-based (36) T1D interventions. To overcome these hurdles, we utilized CRISPR/Cas9 technologies to generate novel NOD stocks in which the classical $H2-K1^d$ and $H2-D1^b$ class I genes were directly ablated individually or in tandem (respectively designated NOD-H2-$K^{-/-}$, NOD-H2-$D^{-/-}$, and NOD-cMHCI$^{-/-}$). We then genetically eliminated the $H2-A^{g7}$ class II variant in NOD-cMHCI$^{-/-}$ mice resulting in a strain fully lacking classical murine MHC molecules (NOD-cMHCI/II$^{-/-}$). These strains retain β2m dependent FcRn activity and can be used as platforms for the introduction of selected combinations of T1D patient relevant HLA class I and II variants. As a first step in validating such second-generation HLA-humanized models, we report HLA-A2 or B39 encoding HHD transgenes support development of T1D inducing $CD8^+$ T-cells in such strains.

"Humanization" of NOD mice allowing expression of chosen HLA combinations has potential to facilitate the mechanistic analysis and development of clinically translatable T1D interventions based on individualized human genetic configurations. Towards that goal, our earlier work described NOD mice expressing the common T1D associated human HLA-A*02:01 class I allele (21; 45). We recently further advanced these resources (31) by transgenically introducing the T1D-susceptibility HLA-B*39:06 class I variant (12; 17-19) into NOD mice. While a relatively low abundance allele, the human B9 class I variant supports aggressive early onset T1D (15; 16) seemingly independent of HLA class II effects (12). The continued expansion of HLA susceptibility alleles in NOD mice is essential for improving the ability of mouse models to test therapeutics for genetically diverse T1D patient populations, as a therapy that may work with the common HLA-A2 allele in place may not be sufficient for the earlier onset disease associated with HLA-B39 (15; 16). We should note that not all HLA class I alleles are capable of supporting T1D in NOD mice, as transgenic expression of HLA-B27 actually inhibits disease development (45).

In the course of these studies, we generated NOD-H2-$D^{-/-}$ and NOD-H2-$K^{-/-}$ mice enabling assessment of the individual contributions of these two genes to T1D development. The lack of either class I variant decreased T1D development indicating a requirement for both H2-D and H2-K restricted antigens in disease pathogenesis. Initial analysis indicates islet-infiltrating $CD8^+$ T-cells in H2-$K^{-/-}$ mice have a more activated phenotype than in NOD or NOD-H2-$D^{-/-}$ mice. It is currently unknown why while proportionally increased, islet-effector $CD8^+$ T-cells in NOD-H2-$K^{-/-}$ mice appear to have dampened pathogenic activity. Work is currently underway to determine specific T-cell populations present and absent within each of these new strains, and how they lead to the seeming discordance between effector status versus insulitis levels.

Figure 10:
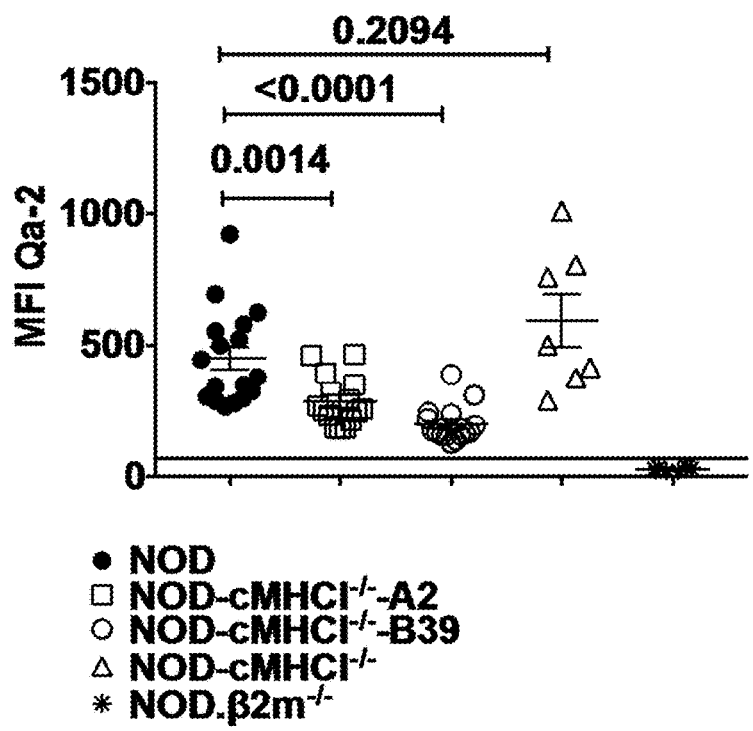
FIG. 10. Qa-2 Expression reduced in NOD-cMHCI$^{-/-}$-HLA mice compared to NOD mice. Quantification of the Mean Fluorescence Intensity (MFI) of Qa-2 antibody staining on splenic CD4$^+$ T-cells from 8-week-old mice to 20-week-old mice comparing NOD vs NOD-cMHCI$^{-/-}$-HLA and NOD-cMHCI$^{-/-}$ mice. NOD.β2m$^{-/-}$ mice are shown for background. Data is combined from four separate experiments. Data is presented as Mean±SEM.

Our previous generation NOD-HLA-humanized models rely on the β2m$^{-/-}$ mutation to eliminate murine MHC I class I expression. β2m plays important roles in immune function beyond stabilizing H2-K and H2-D molecules on the cell surface. The NOD-cMHCI$^{-/-}$-A2 and NOD-cMHCI$^{-/-}$-B39 models described herein retain non-classical MHC I molecules as evidenced by CD1d and Qa-2 expression (FIG. 6). While NOD-cMHCI$^{-/-}$-A2 and NOD-cMHCI$^{-/-}$-B39 mice both express Qa-2, they do so at lower levels than in NOD controls (FIG. 10). Due to its association with early onset of T1D in humans (15; 16), we were surprised at the low level of disease in first generation NOD.β2m$^{-/-}$-B39 mice (31). Interestingly, more robust T1D development was observed when HLA-B39 was expressed in NOD-cMHCI$^{-/-}$ mice compared to when the same transgene was paired with an ablated β2m molecule (31). This suggests there may be a significant contribution(s) of non-classical MHC I molecules to T1D development in the context of HLA-B39 restricted pathogenic CD8$^+$ T-cells. This might include an ability of Qa1 to modulate NK cell activity (46). Previous studies found T1D development is exacerbated in CD1d$^{-/-}$ NOD mice (47). Thus, failure to express the non-classical CD1d MHC class I molecule is unlikely to explain the lower T1D penetrance in NOD.β2m$^{-/-}$-B39 than NOD-cMHCI$^{-/-}$-B39 mice. However, we cannot yet rule out that a CD1d-restricted NKT cell population in NOD-MHCI$^{-/-}$-HLA mice takes on a more pathogenic phenotype (48). Polymorphic genes in the congenic region surrounding β2m may contribute to decreased disease penetrance in NOD.β2m$^{-/-}$-HLA mice. This possible bystander-gene effect is avoided in NOD-cMHCI$^{-/-}$-HLA mice. Finally, another important feature of the reported HLA-humanized NOD direct-murine MHC knockout mice is that they retain FcRn functionality, allowing them to be used to test potential antibody and serum albumin-based T1D interventions.

While the NOD-cMHCI$^{-/-}$-A2 and NOD-cMHCI$^{-/-}$-B39 models described here are improvements on the β2m$^{-/-}$ varieties, they are an intermediate step to full HLA I and II humanization as they retain the murine H2-A$^{g7}$ T1D susceptibility molecule. In their current state, NOD-cMHCI$^{-/-}$-A2 and NOD-cMHCI$^{-/-}$-B39 mice can serve to identify β-cell autoantigens presented by these human class I antigens to diabetogenic CD8$^+$ T-cells, and to test therapies that may attenuate such pathogenic effectors. These models may be improved by replacing murine H2-Ab1$^{g7}$ with human HLA class II transgenes. Towards this end, the NOD-cMHCI/II$^{-/-}$ mice provided herein are the ideal platform for introducing any combination of HLA class I- and II-encoding transgenes. In this manner, flexible models can be generated for subpopulations of T1D patients expressing various HLA class I- and II-allelic combinations. We were surprised that in the absence of all classical MHC molecules, T-cells still constituted ~12% of splenocytes in NOD-cMHCI/II$^{-/-}$ mice. While we cannot completely rule out non-classical H2-Aα/Eβ heterodimers forming in this model, to date we have been unable to detect them via available MHC II reactive antibodies (AMS32.1, M5/114, AF6-120, 10-2.16, 17-3-3). We speculate that in the absence of classical MHC molecules, T-cells selected on non-classical MHC molecules have space to expand in these new models. These may include Type II NKT cells, which are not detected by CD1d-α-GalCer tetramers, MR1 restricted MAIT cells, and other class Ib selected T-cells (49). Additionally, CD90 (with antigen presenting cell co-stimulation) can trigger T-cell proliferation in the absence of TCR engagement (50). Thus, T-cells may undergo non-classical CD90-based selection/homeostatic expansion in NOD-cMHCI/II$^{-/-}$ mice. Therefore, in addition for its utility in generating new models with differing HLA class I and II allelic combinations, these NOD-cMHCI/II$^{-/-}$ may be useful in studying non-classically selected T-cells.

In some embodiments, the present disclosure provides a genetically modified non-obese diabetic (NOD) mouse comprising in the genome of the NOD mouse a homozygous mutation in H2-D1$^b$, a homozygous mutation in H2-K1$^d$, and a homozygous mutation in H2-Ab1$^{g7}$ (e.g., designated NOD/ShiLtDvs-H2-K1$^{em1Dvs}$ H2-Ab1$^{em1Dvs}$ H2-D1$^{em5Dvs}$/Dvs).

In other embodiments, the present disclosure provides a genetically modified non-obese diabetic (NOD) mouse comprising in the genome of the NOD mouse a homozygous mutation in H2-D1$^b$, a homozygous mutation in H2-K1$^d$, and a human HLA-A2 transgene (e.g., designated NOD/ShiLtDvs-H2-K1$^{em1Dvs}$ H2-D1$^{em5Dvs}$ Tg(HLA-A/H2-D/B2M)1Dvs/Dvs).

In yet other embodiments, the present disclosure provides a genetically modified non-obese diabetic (NOD) mouse comprising in the genome of the NOD mouse a homozygous mutation in H2-D1$^b$, a homozygous mutation in H2-K1$^d$, and a human HLA-B39 transgene (e.g., designated NOD/ShiLtDvs-H2-K1$^{em1Dvs}$ H2-D1$^{em5Dvs}$ Tg(HLA-B39/H2-D/B2M)2Dvs/Dvs).

A (at least one, one or more) mutation in a gene may be an insertion, a deletion, a substitution, and/or other modification of the nucleotide sequence of the gene. In some embodiments, a gene mutation reduces expression of the gene (e.g., by at 10%, 20%, 30%, 40%, 50%, 60%, 70%, 80%, 90%, or 95%), relative to a control (e.g., a gene not having the mutation). In other embodiments, a gene mutation eliminates expression of gene (e.g., the product of the gene, e.g., the protein encoded by the gene, cannot be detected, e.g., using antibody detection methods). A heterozygous mutation refers to a mutation in only one of the two copies (alleles) of a gene. A homozygous mutation refers to a mutation in both copies (alleles) of a gene.

A gene knockout ("KO") refers to a gene that has been made inoperative ("knocked out" of the mouse genome). A gene that has been "knocked out" does not express the product (e.g., protein) encoded by the gene. For example, a H2-K1$^d$ knockout does not express H2-K. Likewise, a H2-D1$^b$ knockout does not express H2-D. As another example, a H2-Ab1$^{g7}$ knockout does not express H2-A.

Non-Obese Diabetic (NOD) Mouse Model

The NOD/ShiLtJ strain (commonly referred to as NOD) is a polygenic model for autoimmune type 1 diabetes (T1D). Diabetes in NOD mice is characterized by hyperglycemia and insulitis, a leukocytic infiltration of the pancreatic islets. Marked decreases in pancreatic insulin content occur in females at about 12 weeks of age and several weeks later in males. A 2017 phenotyping study found that 90% of females and 52% of males became diabetic by 30 weeks; median female incidence was 18 weeks. Immune phenotypes in the NOD background consist of defects in antigen presentation, T lymphocyte repertoire, NK cell function, macrophage cytokine production, wound healing, and C5 complement. These defects make the NOD background a common choice for immunodeficient mouse strains. See The Jackson Laboratory website for additional details on the NOD mouse model.

Major Histocompatibility Complex (MHC)

Some aspects of the present disclosure provide genetically modified NOD mice comprising a mutation in a gene encoding major histocompatibility complex (MHC) class I molecule (e.g., H2-K gene and/or H2-D gene) and/or a mutation in a gene encoding a MHC class II molecule (e.g., H2-A gene). In some embodiments, a genetically modified NOD mouse comprises a mutation in a H2-K gene. In some embodiments, a genetically modified NOD mouse comprises a mutation in a H2-D gene. In some embodiments, a genetically modified NOD mouse comprises a mutation in a H2-K gene and a mutation in a H2-D gene. In some embodiments, a genetically modified NOD mouse comprises a mutation in a H2-K gene, a mutation in a H2-D gene, and a mutation in a H2-A gene.

The MHC is a set of cell surface proteins essential for the adaptive immune system to recognize foreign molecules in vertebrates, which in turn determines histocompatibility. The main function of MHC molecules is to bind to antigens derived from pathogens and display them on the cell surface for recognition by the appropriate T-cells (Janeway et al. Immunobiology: The Immune System in Health and Disease. 5th edition. New York: Garland Science; 2001).

The MHC gene family is divided into three subgroups: class I, class II, and class III. class I MHC molecules have β2 subunits so can only be recognized by CD8 co-receptors. class II MHC molecules have β1 and β2 subunits and can be recognized by CD4 co-receptors.

The MHC in mice is known as the H2 complex or H2.

Mouse MHC includes the "classical MHC class I" (MHC-Ia) that includes subclasses H2-D, H2-K, and H2-L, the "non-classical MHC class I" (MHC-Ib) that includes subclasses H2-Q, H2-M, and H2-T, the "classical MHC class II" (MHC-IIa) that includes subclasses H2-A(I-A) and H2-E (I-E), and the "non-classical MHC class II" (MHC-IIb) that includes subclasses H2-M and H2-O. MHC class I molecules is composed of a 45 kD highly glycosylated heavy chain non-covalently associated with a 12 kD β2-microglobulin, a polypeptide that is also found free in serum. Mouse MHC class II genes are located in the H2 I region. The class II antigen is composed of a 33 kD α chain and a 28 kD β chain. MHC class I antigens are expressed on almost all nucleated cells. They play a role in presentation of altered self cell antigens (virally infected or tumor cells) to $CD8^+$ cytotoxicity T cells. The MHC class II antigens are expressed on antigen presenting cells (B cells, monocytes/macrophages, dendritic cells, and Langerhans cells, etc.). They are involved in presentation of processed peptide antigens to $CD4^+$ cells. MHC molecules are highly polymorphic. In general, each laboratory mouse strain is homozygous and has a unique MHC haplotype. The MHC haplotype in these strains is designated by a small letter (a, b, d, k, q, s, etc.). Specific information on the haplotype of most known mouse strains may be found in Klein et al. (1983) Immunogenetics 17(6):553-96.

The major histocompatibility locus haplotype of an animal may be determined, in some embodiments, through conventional typing methods, for example, where outbred animals are used, or from known information concerning the genetic characteristics of the animal.

In some embodiments, the genome of a NOD mouse comprises a mutation in a H2-K gene. In some embodiments, the genome of a NOD mouse comprises a mutation in a H2-D gene. In some embodiments, the genome of a NOD mouse comprises a mutation in a H2-K gene and a mutation in a H2-D gene. The H2-K gene may be, for example, a $H2-K^d$ gene. The H2-D gene may be, for example, a $H2-D^b$ gene. Thus, in some embodiments, the genome of a NOD mouse comprises a mutation in a $H2-K^d$ gene and a mutation in a $H2-D^b$ gene (NOD-cMHCI$^{-/-}$).

The genome of a NOD mouse, in some embodiments, further comprises a mutation in a H2-A gene. The H2-A gene may be, for example, a H2-Ab1$^{g7}$ gene. In some embodiments, the genome of a NOD mouse comprises a mutation in a H2-K gene, a mutation in a H2-D gene, and a mutation in a H2-A gene. Thus, in some embodiments, the genome of a mouse comprises a mutation in a $H2-K^d$ gene, a $H2-D^b$ gene, and a H2-Ab1$^{g7}$ gene (NOD-cMHCI/II$^{-/-}$).

The human MHC is also called the HLA (human leukocyte antigen). In human, the MHC class I molecules include HLA-A (e.g., HLA-A1, HLA-A2), HLA-B, HLA-C, HLA-E, HLA-F, HLA-G, HLA-K, and HLA-L molecules. Classical human MHC class I molecules include HLA-A, HLA-B, HLA-C.

In human, the MHC class II molecules include HLA-DP (e.g., HLA-DPA1, HLA-DPB1), HLA-DQ (e.g., HLA-DQA1, HLA-DQB1), HLA-DR (e.g., HLA-DRA, HLA-DRB1, HLA-DRB3, HLA-DRB4, HLA-DRB5), HLA-DM, HLA-DOA, and HLA-DOB. Classical human MHC class II molecules include HLA-DPA1, HLA-DPB1, HLA-DQA1, HLA-DQB1, HLA-DRA, and HLA-DRB1.

In some embodiments, the genome of a NOD mouse of the present disclosure further comprises a nucleic acid encoding human HLA-A, a nucleic acid encoding human HLA-B, or a nucleic acid encoding a human HLA-A gene and a nucleic acid encoding a human HLA-B gene. In some embodiments, the HLA-A is HLA-A*02:01 (also referred to as HLA-A2). In some embodiments, the HLA-B is HLA-B*39:06 (also referred to as HLB-B39). Thus, in some embodiments, the genome of a NOD mouse further comprises a nucleic acid encoding human HLA-A2, a nucleic acid encoding human HLA-B39, or a nucleic acid encoding a human HLA-A2 gene and a nucleic acid encoding a human HLA-B39 gene. In some embodiments, the genome of a NOD mouse of the present disclosure further comprises a nucleic acid encoding human HLA-DQ, a nucleic acid encoding human HLA-DR, or a nucleic acid encoding human HLA-DQ and a nucleic acid encoding HLA-DR. In some embodiments, the HLA-DQ is HLA-DQ8 (Nabozny G et al. J. Exp. Med. 1996; 183: 27-37). In some embodiments, the HLA-DR is HLA-DR3/4. Thus, in some embodiments, the genome of a NOD mouse of the present disclosure further comprises a nucleic acid encoding human HLA-DQ8, a nucleic acid encoding human HLA-DR3/4, or a nucleic acid encoding human HLA-DQ8 and a nucleic acid encoding HLA-DR3/4.

The genetically modified NOD mice of the present disclosure advantageously retain non-classical murine MHC I molecule expression and FcRn activity (unlike NOD.β2m$^{-/-}$ mice), enabling use of the mice for the development of antibody-based T1D interventions. The neonatal Fc receptor (FcRn), also known as the Brambell receptor, is an Fc receptor which is similar in structure to the MHC class I molecule and also associates with β2-microglobulin. It was first discovered in rodents as a unique receptor capable of transporting IgG from mother's milk across the epithelium of newborn rodent's gut into the newborn's bloodstream. Further studies revealed a similar receptor in humans. In humans, however, it is found in the placenta to help facilitate transport of mother's IgG to the growing fetus and it has also been shown to play a role in monitoring IgG turnover (Kuo et al., Neonatal Fc receptor and IgG-based therapeutics, mAbs, 2011, 3 (5): 422-430). Mouse models lacking FcRN activity, which is required for IgG maintenance, cannot be used for testing antibody-based T1D interventions.

Genetically Modified Mice

A genetically modified mouse (*Mus musculus*) is a mouse that has had its genome altered through the use of genetic engineering techniques. Genetically modified mice are commonly used for research or as animal models of human diseases, and are also used for research on genes. There are three basic technical approaches for producing genetically modified mice.

The first involves pronuclear injection into a single cell of the mouse embryo, where it will randomly integrate into the mouse genome (Gordon J W et al. *Proc. Natl. Acad. Sci. USA* 1980; 77 (12): 7380-7384). This method creates a transgenic mouse and is used to insert new genetic information into the mouse genome or to over-express endogenous genes.

The second approach involves modifying embryonic stem cells with a DNA construct containing DNA sequences homologous to the target gene. Embryonic stem cells that recombine with the genomic DNA are selected for and they are then injected into the mice blastocysts (Thomas K R, Capecchi M R *Cell* 1987; 51 (3): 503-12). This method is used to manipulate a single gene, in most cases "knocking out" the target gene, although more subtle genetic manipulation can occur (e.g., only changing single nucleotides).

The third approach uses the CRISPR/Cas (Clustered Regularly Interspaced Short Palindromic Repeats (CRISPR)/CRISPR-associated proteins (Cas)) gene editing system. Mouse models can be generated with CRISPR/Cas9 by injecting Cas9 mRNA and either one or multiple single guide RNAs (sgRNA) directly into mouse embryos to generate precise genomic edits into specific loci (see, e.g., Harms D W et al. *Curr. Protoc. Hum. Genet.* 2014; 83(1); and Qin W et al. *Genetics* 2015; 200(2): 423-430). Mice that develop from these embryos are genotyped or sequenced to determine if they carry the desired mutation(s), and those that do are bred to confirm germline transmission. As CRISPR/Cas9 will work in most mouse strains, new mutations can be directly generated in a genetic background of choice. This eliminates the need, time, and resources to backcross mutations from one genetic background to another, which is a typical practice when generating mutant mice by traditional methods. New mutations also can be added to existing mouse strains that already carry desired mutations, reducing the time and costs to generate double and triple mutant mice.

Genetically modified mice of the present disclosure comprise a mutation in a gene encoding a MHC class I and/or class I molecule. It should be understood that various methods can be used to disrupt the MHC gene to produce a genetically modified animal. Additional methods of genetic engineering include, but are not limited to, chemical mutagenesis, irradiation, homologous recombination and transgenic expression of antisense RNA. Such techniques are well-known in the art and further include, but are not limited to, pronuclear microinjection and transformation of embryonic stem cells. See, e.g., J. P. Sundberg and T. Ichiki, Eds., Genetically Engineered Mice Handbook, CRC Press; 2006; M. H. Hofker and J. van Deursen, Eds., Transgenic Mouse Methods and Protocols, Humana Press, 2002; A. L. Joyner, Gene Targeting: A Practical Approach, Oxford University Press, 2000; Manipulating the Mouse Embryo: A Laboratory Manual, 3rd edition, Cold Spring Harbor Laboratory Press; Dec. 15, 2002, ISBN-10: 0879695919; Kursad Turksen (Ed.), Embryonic stem cells: methods and protocols in Methods Mol Biol. 2002; 185, Humana Press; Current Protocols in Stem Cell Biology, ISBN: 978047015180; Meyer et al. PNAS USA, vol. 107 (34), 15022-15026.

The genetically modified NOD mice of the present disclosure, in some embodiments, are generated using the CRISPR/Cas9 system. For example, as provided herein, guide RNA (gRNA) molecules may be designed to target Cas9 nuclease to exon 3 of H2-K1 (e.g., ATAATCCGAGAT-TTGAGCCG; SEQ ID NO:12), to exon 2 of H2-D1 (e.g., GTACATCTCTGTCGGCTATG; SEQ ID NO:9), and/or to exon 2 of H2-AB1$^{g7}$ (e.g., CCAACGGGACGCAGCG-CATA (SEQ ID NO:15); CGACGTGGGCGAGTACCGCG (SEQ ID NO:16); CGAAGCGCAGGTACTCCTCC (SEQ ID NO:17); ACACAACTACGAGGAGACGG; SEQ ID NO:18). See Figures for example sequences.

A gRNA is a ribonucleic acid, in some embodiments, having a scaffold sequences that associates (e.g., binds to) Cas nuclease and a spacer sequence that determines specificity by binding to a target sequence (e.g., in the genome). Scaffold sequences are known and described, for example, in Jinek et al. *Science* 2012; 337(6096): 816-821, and Ran et al. *Nature Protocols* 2013; 8: 2281-2308. The gRNA spacer sequence, in some embodiments, has a length of about 15 to 25 (e.g., 15, 16, 17, 18, 19, 20, 21, 22, 23, 24, or 25) nucleotides.

Non-limiting examples of Cas proteins that may be used as provided herein include Cas1, Cas1B, Cas2, Cas3, Cas4, Cas5, Cas5e (CasD), Cas6, Cas6e, Cas6f, Cas7, Cas8a1, Cas8a2, Cas8b, Cas8c, Cas9 (Csn1 or Csx12), Cas10, Cas10d, CasF, CasG, CasH, Cpf1, Csy1, Csy2, Csy3, Cse1 (CasA), Cse2 (CasB), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cu1966, and homologs or modified versions thereof. In some embodiments, the Cas nuclease is a Cas9 nuclease. The Cas9 nuclease may be obtained from *Streptococcus pyogenes*, *Streptococcus thermophilus*, *Streptococcus* sp., *Staphylococcus aureus*, *Nocardiopsis dassonvillei*, *Streptomyces pristinaespiralis*, *Streptomyces viridochromogenes*, *Streptomyces viridochromogenes*, *Streptosporangium roseum*, *Streptosporangium roseum*, *Alicyclobacillus acidocaldarius*, *Bacillus pseudomycoides*, *Bacillus selenitireducens*, *Exiguobacterium sibiricum*, *Lactobacillus delbrueckii*, *Lactobacillus salivarius*, *Microscilla marina*, *Burkholderiales bacterium*, *Polaromonas naphthalenivorans*, *Polaromonas* sp., *Crocosphaera watsonii*, *Cyanothece* sp., *Microcystis aeruginosa*, *Synechococcus* sp., *Acetohalobium arabaticum*, *Ammonifex degensii*, *Caldicelulosiruptor becscii*, *Candidatus Desulforudis*, *Clostridium botulinum*, *Clostridium difficile*, *Finegoldia magna*, *Natranaerobius thermophilus*, *Pelotomaculum thermopropionicum*, *Acidithiobacillus caldus*, *Acidithiobacillus ferrooxidans*, *Allochromatium vinosum*, *Marinobacter* sp., *Nitrosococcus halophilus*, *Nitrosococcus watsoni*, *Pseudoalteromonas haloplanktis*, *Ktedonobacter racemifer*, *Methanohalobium evestigatum*, *Anabaena variabilis*, *Nodularia spumigena*, *Nostoc* sp., *Arthrospira maxima*, *Arthrospira platensis*, *Arthrospira* sp., *Lyngbya* sp., *Microcoleus chthonoplastes*, *Oscillatoria* sp., *Petrotoga mobilis*, *Thermosipho africanus*, or *Acaryochloris marina*. In some embodiments, the Cas9 nuclease is from *S. pyogenes*, assigned SwissProt accession number Q99ZW2.

Also provided herein are cells comprising in the genome of the cells a homozygous mutation in a H2-K gene, a homozygous mutation in a H2-D gene, or a homozygous mutation in a H2-K gene and a homozygous mutation in a H2-D gene. The cells, in some embodiments, further comprise in the genome of the cells a homozygous mutation in a H2-A gene. A cell, in some embodiments, is isolated (e.g., not surrounded by tissue and/or vasculature, or not located within a mouse). A cell, in some embodiments, is isolated from (obtained from) from a genetically modified NOD mouse of the present disclosure. Non-limiting examples of cell types used as provided herein include endothelial cells, epithelial cells, fibroblasts, leukocytes, pancreatic cells, liver hepatocytes, and neuronal cells. These cells, in some embodiments, are useful in assay systems for identifying therapeutic agents described herein.

A humanized mouse is a genetically modified mouse expressing a human HLA molecule.

It should be understood that while the present disclosure primarily describes genetically modified mice, other animal model systems may be used. For example, the present disclosure encompasses other rodent (e.g., mouse and/or rat) models of T1D, such as spontaneous autoimmune models including NOD mice, BB rats and LEW.1AR1/-iddm rats, and genetically induced models including AKITA mice (see, e.g., King, *Brit. J. Pharmacol.* 2012; 166(3): 877-894).

Mouse Model for Diabetes Research

Aspects of the present disclosure provide methods that include administering a test agent to a genetically modified NOD mouse described herein, and assaying the genetically modified NOD mouse (e.g., a biological sample obtained from the modified NOD mouse) for a symptom of diabetes. The genetically modified NOD mice as provided herein may also be used, in some embodiments, to test the effects of MHC/HLA molecules, particularly combinations of MHC/HLA molecules, on the development and/or progression of diabetes. In some embodiments, the methods include introducing into the genome of the genetically modified NOD mice a nucleic acid encoding a human MHC class I molecule and/or a nucleic acid encoding a human MHC class II molecule, and producing humanized NOD mice comprising a genome that expresses the human MHC class I molecule and/or expresses the human MHC class II molecule. The humanized NOD mice (e.g., a biological sample obtained from the humanized NOD mice) may then be assessed for a symptom of diabetes (e.g., glycosuria and/or insulitis). Biological samples herein include, but are not limited to, blood (e.g., plasma and/or serum) samples, urine samples, saliva samples, bone marrow samples, spleen samples, liver samples, and cerebrospinal fluid samples.

A test agent may be administered orally and/or parenterally (e.g., intravenously, intraperitoneally, and/or subcutaneously). The dosage form for the administration is also appropriately determined depending on the administration route and/or properties of the test agent.

A test agent can be any chemical or biological agent, synthetic or naturally-occurring. Non-limiting examples of test agents include small organic or inorganic molecules, polypeptides (e.g., proteins, peptides), nucleic acids (e.g., DNA, RNA, e.g., mRNA), carbohydrates, oligosaccharides, lipids, and combinations of the foregoing. In some embodiments, a test agent is an antibody (e.g., a monoclonal antibody, a scFv). In some embodiments, a test agent is an antigen (e.g., induces an immune response).

Assessing (e.g., assaying for) a symptom of diabetes includes assessing conditions associated with diabetes development and/or progression. Glycosuria, for example, is a condition characterized by an excess of sugar in the urine, typically associated with diabetes or kidney disease. Thus, assaying for a symptom of diabetes may include a urine test of animal to measure sugar levels. In some embodiments, diabetes development is defined by glycosuric values of ≥3, e.g., as assessed with a test strip capable of testing urine, blood, or plasma for the presence and concentration of glucose and/or and ketone (acetoacetic acid). In some embodiments, the test strip is Ames Diastix. In some embodiments, the test strip contains sodium nitroprusside for testing ketone, and/or contains glucose oxidase, peroxidase, and potassium iodide for testing glucose. In some embodiments, the test strip (e.g., Ames Diastix) is used to assess glycosuria weekly. T1D onset is defined, in some embodiments, by two readings of ≥0.25% (≥300 mg/dl in blood) on two separate days.

As another example, insulitis is an inflammation of the islets of Langerhans that can result in destruction of the insulin producing beta cells of the islets and clinical diabetes. Thus, assaying for a symptom of diabetes may include measuring inflammation or other inflammatory responses in an animal. Insulitis development, in some embodiments, is assessed by histological analyses where mean insulitis scores are determined using a 0 (no visible lesions) to 4 (75-100% islet destruction) scoring method. For example, pancreases of the mice are fixed and sectioned at three nonoverlapping levels. Granulated β cells are stained with aldehyde fuchsin, and leukocytes are stained with a H&E counterstain. Islets (at least 20/mouse) are individually scored as follows: 0, no lesions; 1, peri-insular leukocytic aggregates, usually periductal infiltrates; 2, <25% islet destruction; 3, >25%-75% islet destruction; and 4, 75%-complete islet destruction. An insulitis score for each mouse can be obtained by dividing the total score for each pancreas by the number of islets examined. Data are presented as the mean insulitis score (MIS) ±SEM for the indicated experimental group. See, e.g., Johnson et al. *J Immunol* 2001; 167: 2404-2410.

B cells may contribute to diabetes in NOD mice by supporting development in the vicinity of pancreatic islets of tertiary lymphoid structures where pathogenic T cells might be activated. Thus, in some embodiment, B cells within pancreatic islet leukocytic infiltrates are assessed. For example, islet-infiltrating leukocyte populations (e.g., B cell populations) are isolated for flow cytometry. Islets can be isolated and cultured overnight on an individual donor basis, allowing for egress of associated leukocytes that are harvested for flow cytometric analyses of B-cell content. See, e.g., Serreze et al. *Diabetes* 2011; 60: 2914-2921.

A normal level of glucose in human is in the range of from about 65 mg/dL to about 140 mg/dL. Diabetes can result in transient hyperglycemia as the organism is unable to maintain normoglycemia following a glucose load (for example, a carbohydrate-containing meal). Impaired glucose tolerance in humans can be defined as a plasma glucose concentration greater than or equal to 140 mg/dl (7.8 mmol/1) two hours after ingestion of a 75 g oral glucose load. Normal ranges of blood sugar in mice are 60-130 mg/ml, similar to those in humans. Impaired insulin sensitivity can be determined by IV glucose tolerance test (FSIVGTT), insulin tolerance test (ITT), insulin sensitivity test ($1^{ST}$), and continuous infusion of glucose with model assessment (CIGMA), or the glucose clamp. See, e.g., Krentz, Insulin Resistance (Wiley-Blackwell, 2002); de Paula Martins et al., Eur. J. Obst. Gynecol. Reprod. Biol. 133(2):203-207 (2007).

Type 1 diabetes may also be assessed by assaying blood sugar levels of a mouse, optionally in conjunction with the administration of a glucose tolerance test to the mouse. Titers of circulating autoantibodies (e.g., in diagnostic assays such as Western blot, ELISA, RIA, ELISPOT, and the like) may be assayed. See, e.g., Corte-Real et al. *Ann N Y Acad Sci.* 2009; 1173: 442-8.

Tests for detection of glucose, insulin and other metabolites for humans can be performed in mice with minor modifications (e.g., use 75 mg not 75 g of glucose for oral challenge) (see, e.g., Pacini et al. Journal of Diabetes Research, doi: 10.1155/2013/986906 (2013)). The oral glucose challenge test mimics the normal route of consuming carbohydrates. The ingested glucose (usually instilled into the stomach) is absorbed in the intestinal tract and enters the splanchnic circulation and then into the systemic circulation. The increased blood glucose concentration stimulates the pancreatic beta cell to release insulin, which stimulates glucose uptake by peripheral tissues. The passage of the nutrients through the early part of the intestine stimulates the release of the gut hormones (e.g., glucose-dependent insulinotropic polypeptide, GIP, and glucagon-like peptide-1, GLP-1), which in turn augment the beta cell sensitivity to glucose, increasing the production of insulin.

For example, in a 30-min-period after anesthesia, a gavage tube (outer diameter 1.2 mm) is placed in the stomach to be used to administer glucose (dose 75 mg/mouse) in few seconds (standardized volume of 0.5 mL, approximate energy content 0.171 kcal). Blood samples are collected from the retrobulbar, intraorbital, capillary plexus into heparinized tubes before and either 5, 10, and 20 min or 15, 30, 60, and 90 min after oral gavage.

Changes in a level of glucose, insulin or other analyte can be determined by comparison with an appropriate control, such as blood glucose levels in control animals that have not received the test substance, or control animals which do not have the deficient MHC molecule(s). Existing drugs for diabetes (e.g., T1D) can be used as positive controls.

T cell Assays for the detection of T cells with specific reactivities are well known in the art, and include the mixed lymphocyte reaction (MLR) and the ELISPOT assay. ELISPOT assays are described, for example in Taguchi et al., J Immunol Meth 1990, 128:65 and Sun et al., J Immunol 1991 146:1490. In some embodiments, transgene expression of HLA-A2.1 in the absence of any murine class I molecules restores the generation of pathogenic $CD8^+$ T-cells mediating insulitis and T1D development (33). In some embodiments, transgene expression of HLA-B39 in the absence of murine class I molecules restores generation of T1D inducing $CD8^+$ T-cells.

Rates of diabetes development or insulitis development may be assessed for statistically significant differences.

EXAMPLES

The present disclosure is further illustrated by the following Examples. These Examples are provided to aid in the understanding of the disclosure, and should not be construed as a limitation of the disclosure.

Example 1. Creation of Novel NOD-H2-D$^{-/-}$ and NOD-H2-K$^{-/-}$ Mice

Figure 2B:
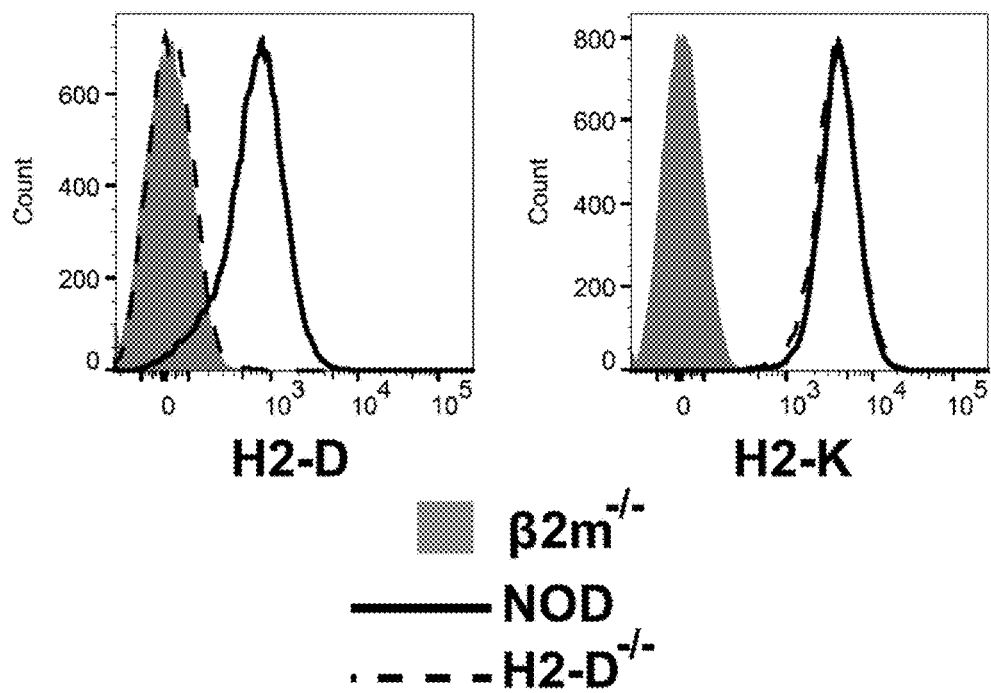
Figure 2C:
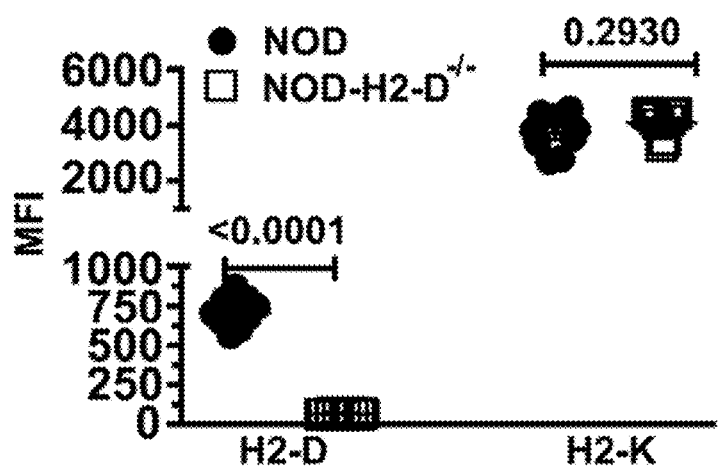
Figure 2D:
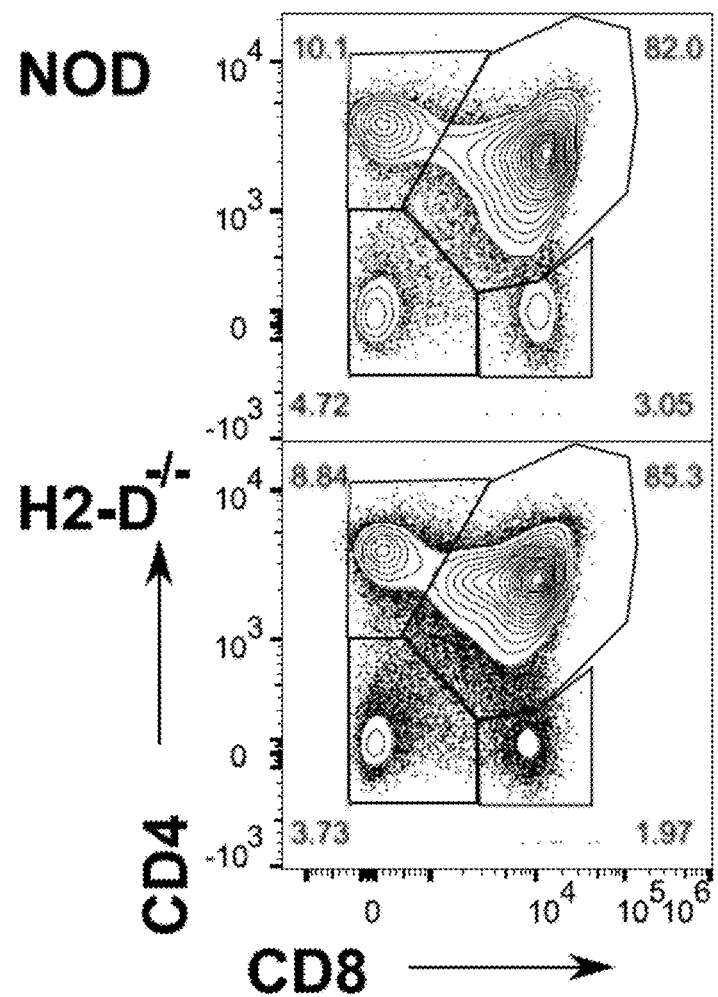
Figure 2E:
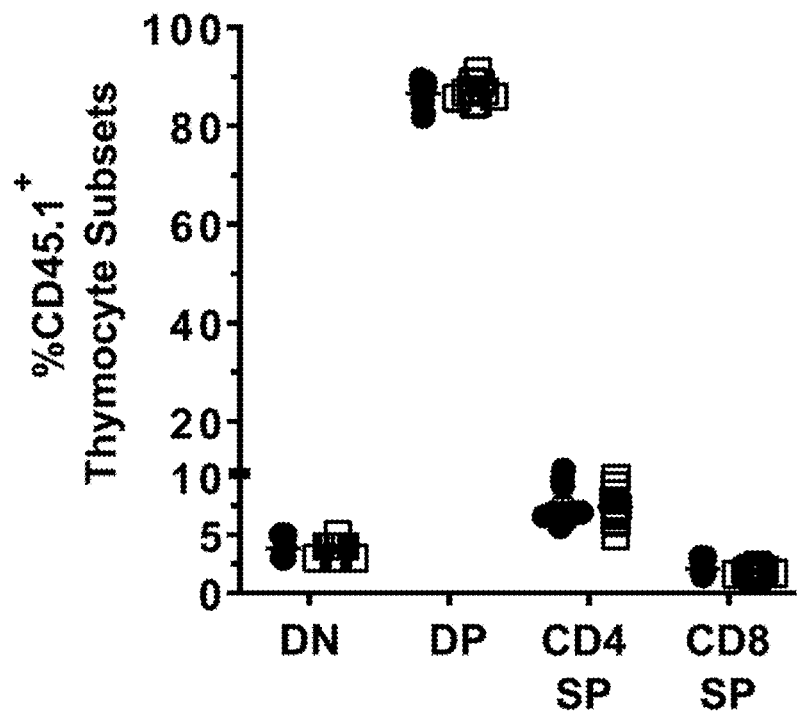
Figure 2F:
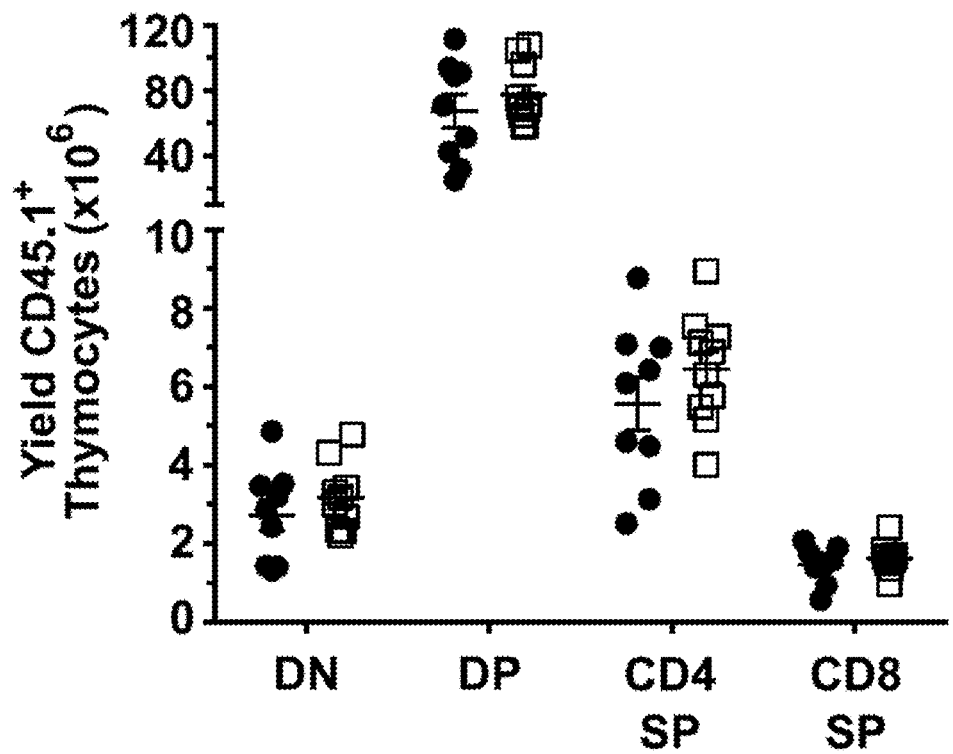
Figure 2G:
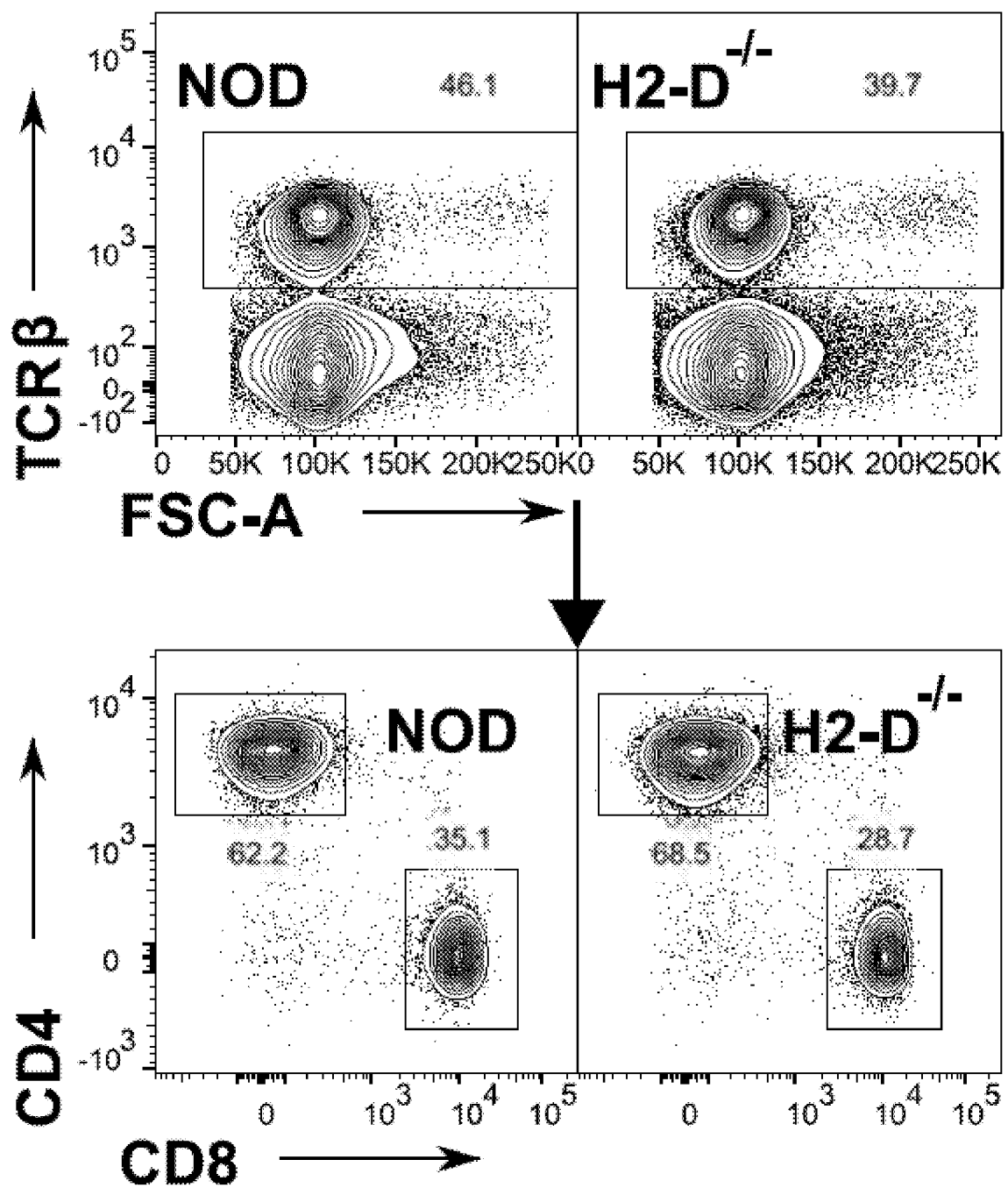
Figure 2H:
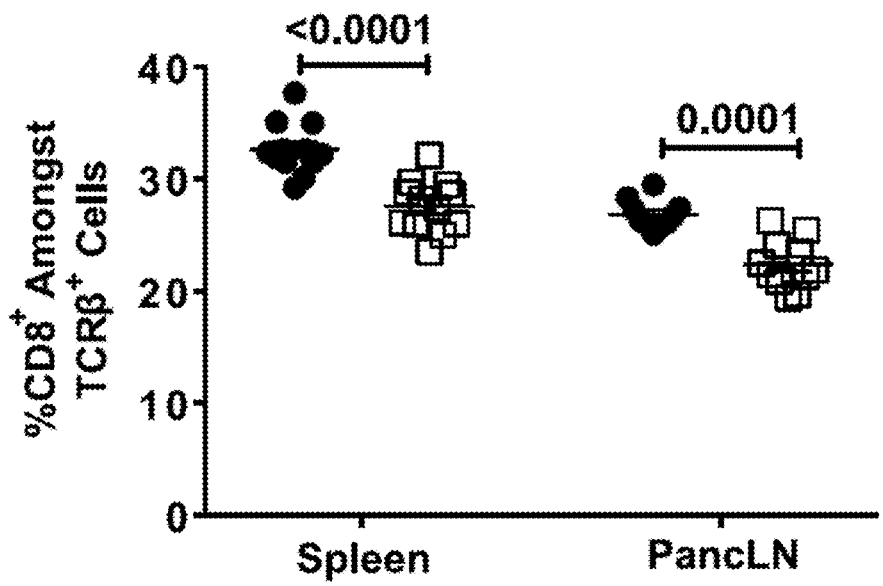
Figure 2I:
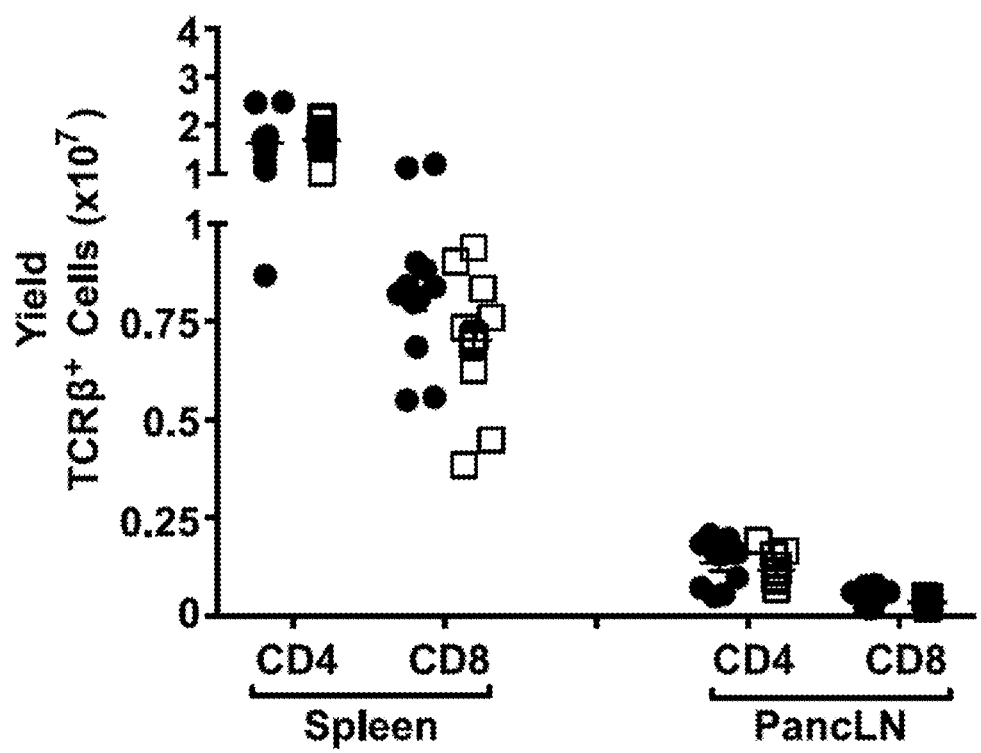

We previously generated through combined use of the $\beta 2$ m$^{-/-}$ mutation and HHD based transgenes, murine MHC class I deficient NOD mouse stocks expressing human HLA-A*02:01 (A2) (Takaki T et al. *J. Immunol.* 2006; 176: 3257) or HLA-B*39:06 (B39) (Sch J et al. *J. Immunol.* 2018; 200: 3353) counterparts capable of supporting diabetogenic $CD8^+$ T-cell responses (4; 30; 31). However, the $\beta 2$ m$^{-/-}$ mutation also ablates expression of non-classical class I molecules including CD1d or Qa-2 (FIGS. 1A-1B) and FcRn. Thus, the $\beta 2$ m$^{-/-}$ mutation negatively impacts the ability to evaluate possible T1D interventions whose activities require non-classical MHCI/β2m protein complexes. For this reason, we created new direct-in-NOD MHC I knockout models to improve upon the first-generation HLA-humanized mice. We further envisioned these novel stocks would provide a means to understand the independent contributions of the $K^d$ and $D^b$ classical class I alleles to T1D pathogenesis in NOD mice. Initially NOD-H2-D$^{-/-}$ mice were generated utilizing CRISPR/Cas9 to target exon 2 of H2-D1$^b$. Four resultant lines were bred to homozygosity (FIG. 2A, and data not shown). A NOD-H2-D$^{-/-}$ line carrying a single nucleotide deletion within exon 2 (FIG. 2A) was chosen for in-depth analysis based on breeding proclivity. As expected, B220$^+$ splenocytes (and other populations, FIG. 9) from H2-D$^{-/-}$ mice lack H2-D, but retain H2-K expression (FIGS. 2B-2C). There are no obvious perturbations of thymic populations based on frequency (FIGS. 2D-2E) or yield (FIG. 2F). However, there is a subtle shift in the percent of $CD8^+$ T-cells in the spleen and pancreatic lymph node (PancLN) (FIGS. 2G-2H). This shift, however, did not correspond to any changes in the yield of either $CD4^+$ or $CD8^+$ T-cells in spleens or PancLNs (FIG. 2I).

Figure 3A:
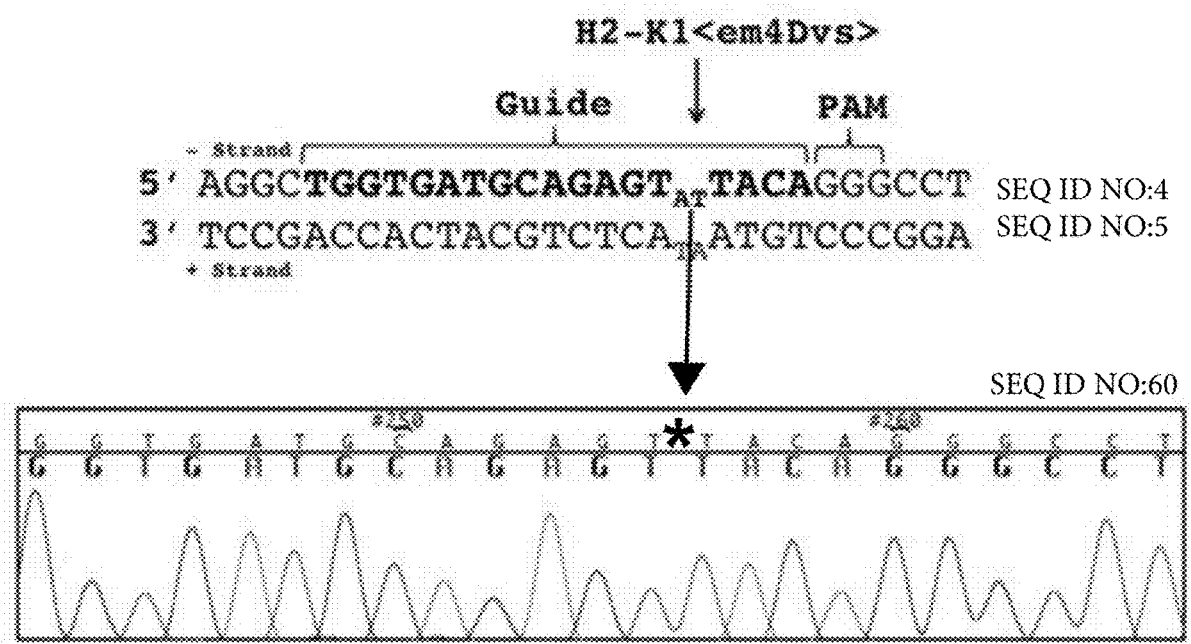
FIGS. 3A-3I. Novel, direct-in-NOD H2-K knockout mouse generated with CRISPR/Cas9.
Figure 3B:
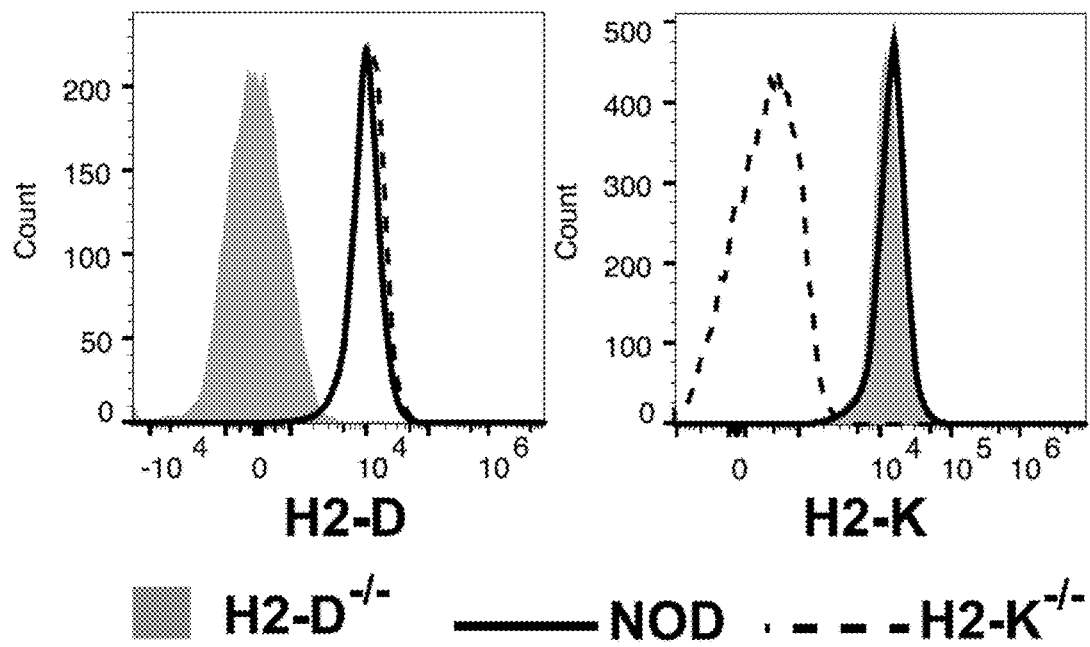
Figure 3C:
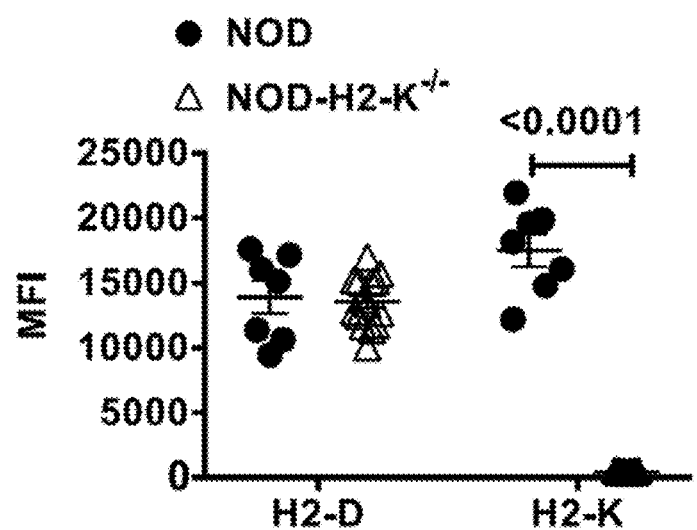
Figure 3D:
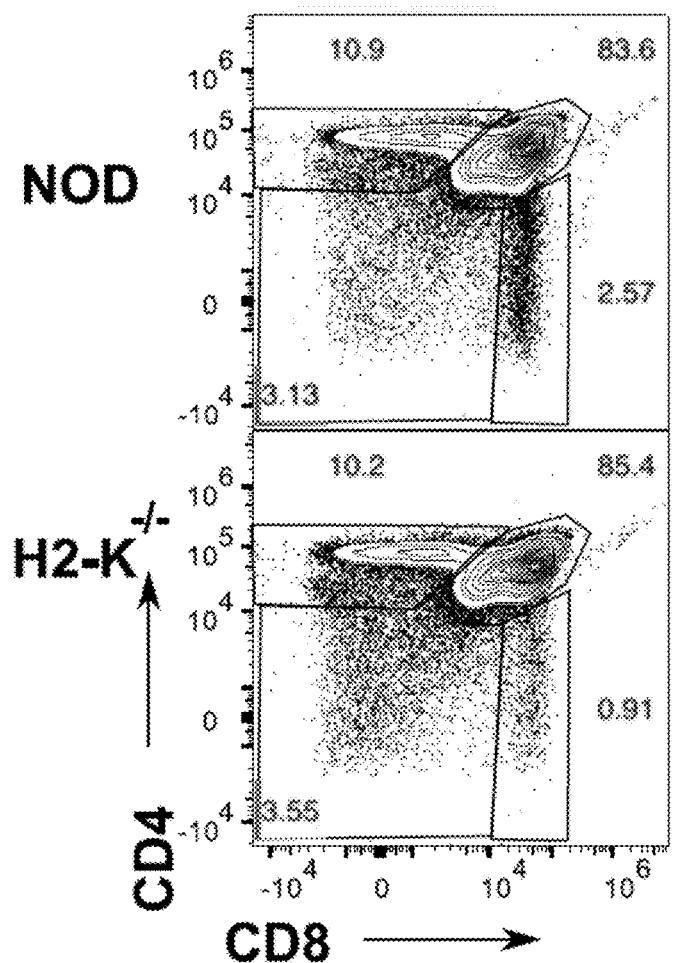
Figure 3E:
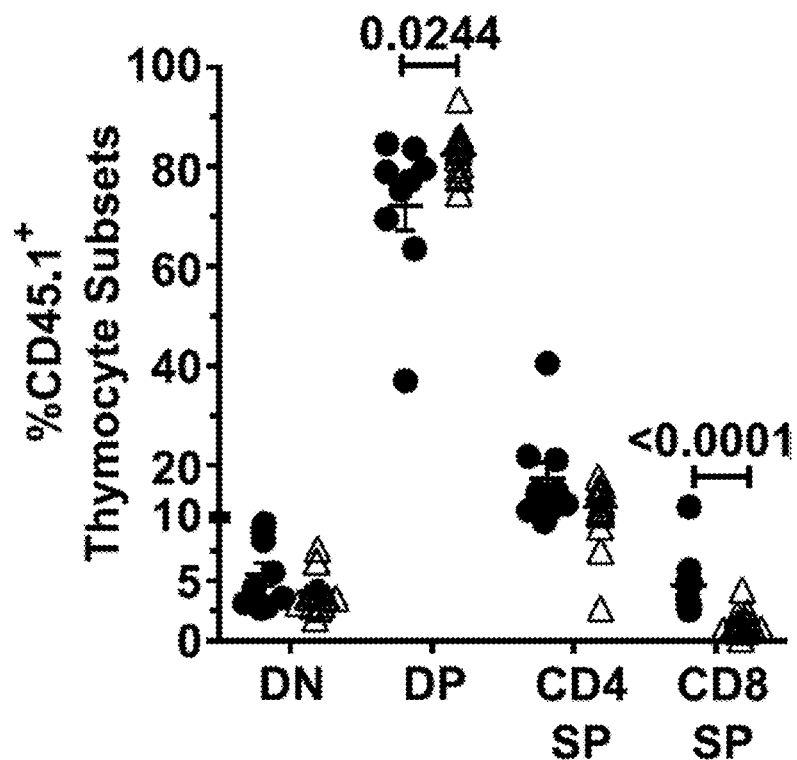
Figure 3F:
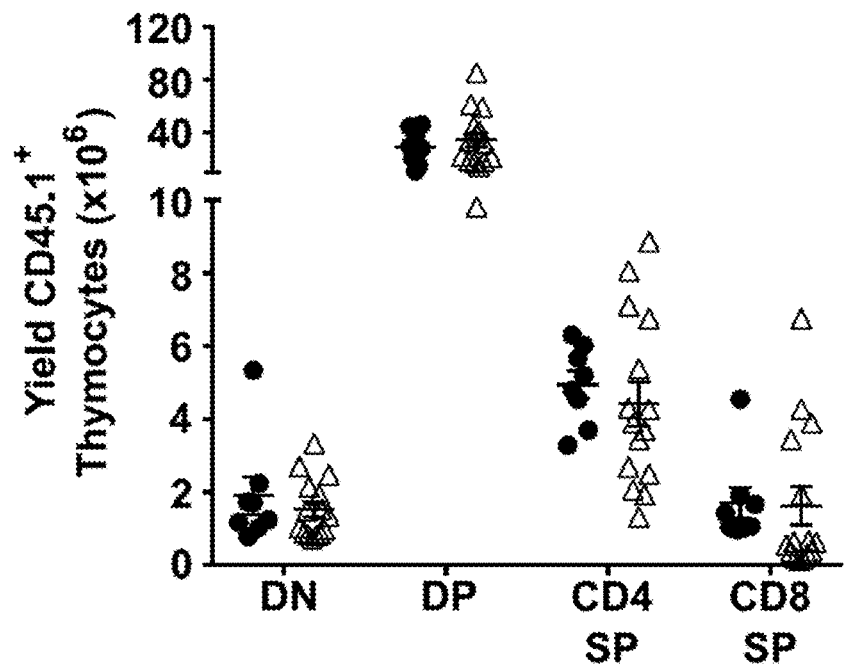
Figure 3G:
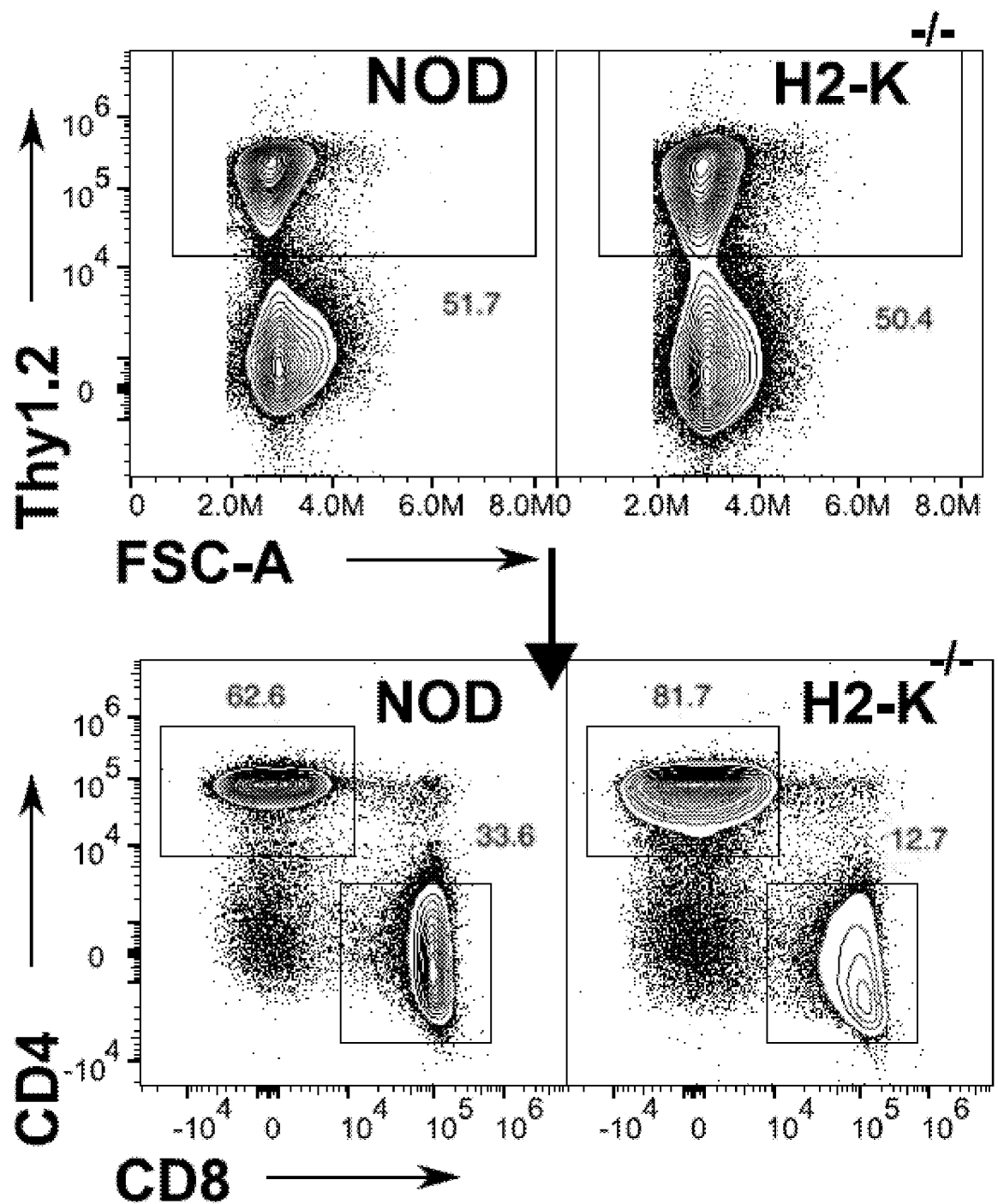
Figure 3H:
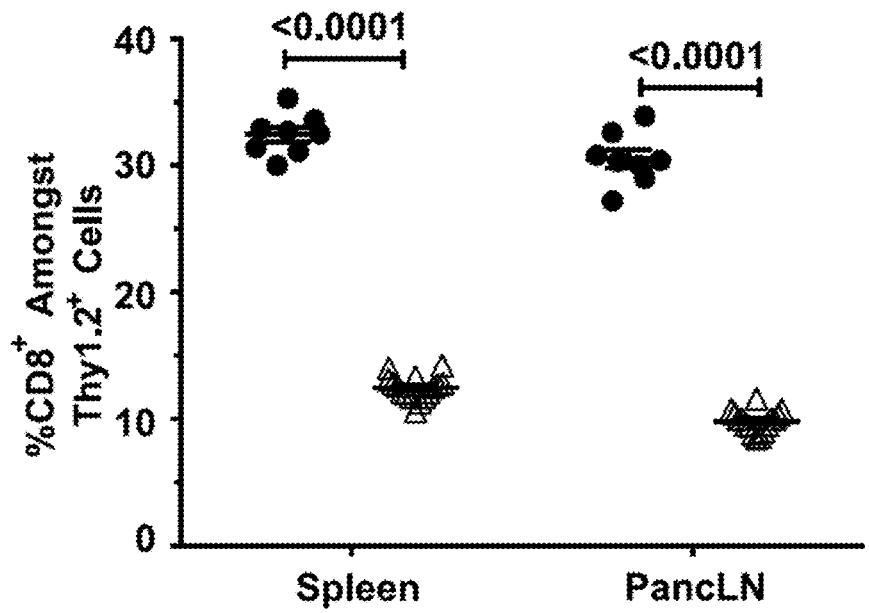
Figure 3I:
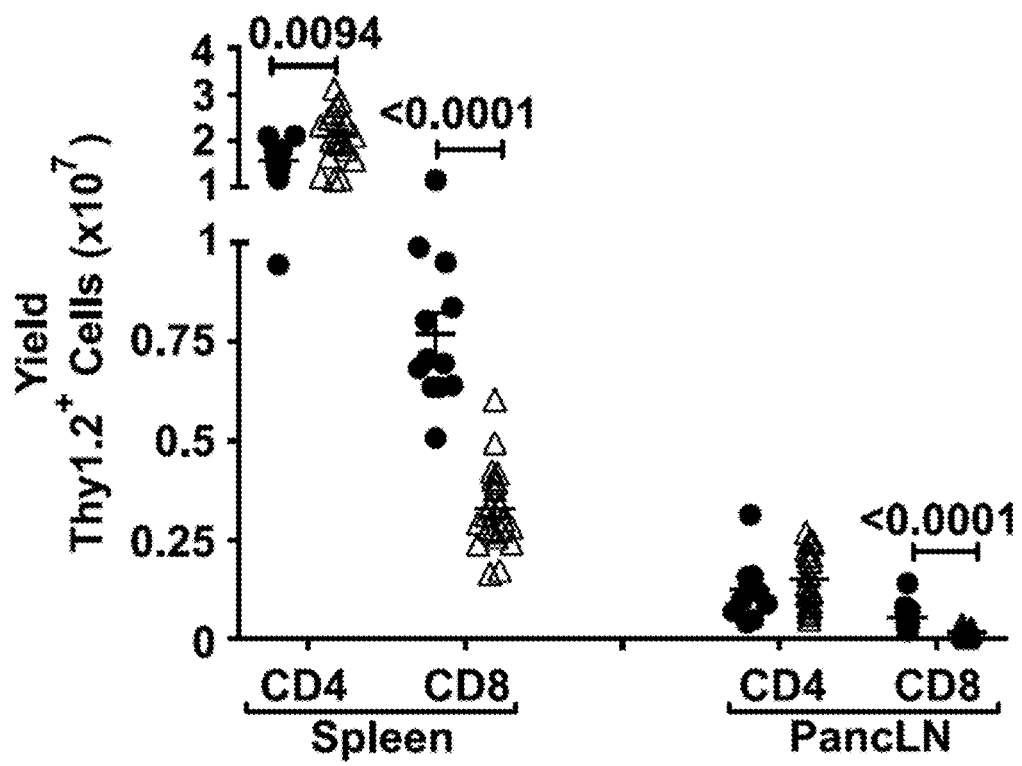
Figure 9:
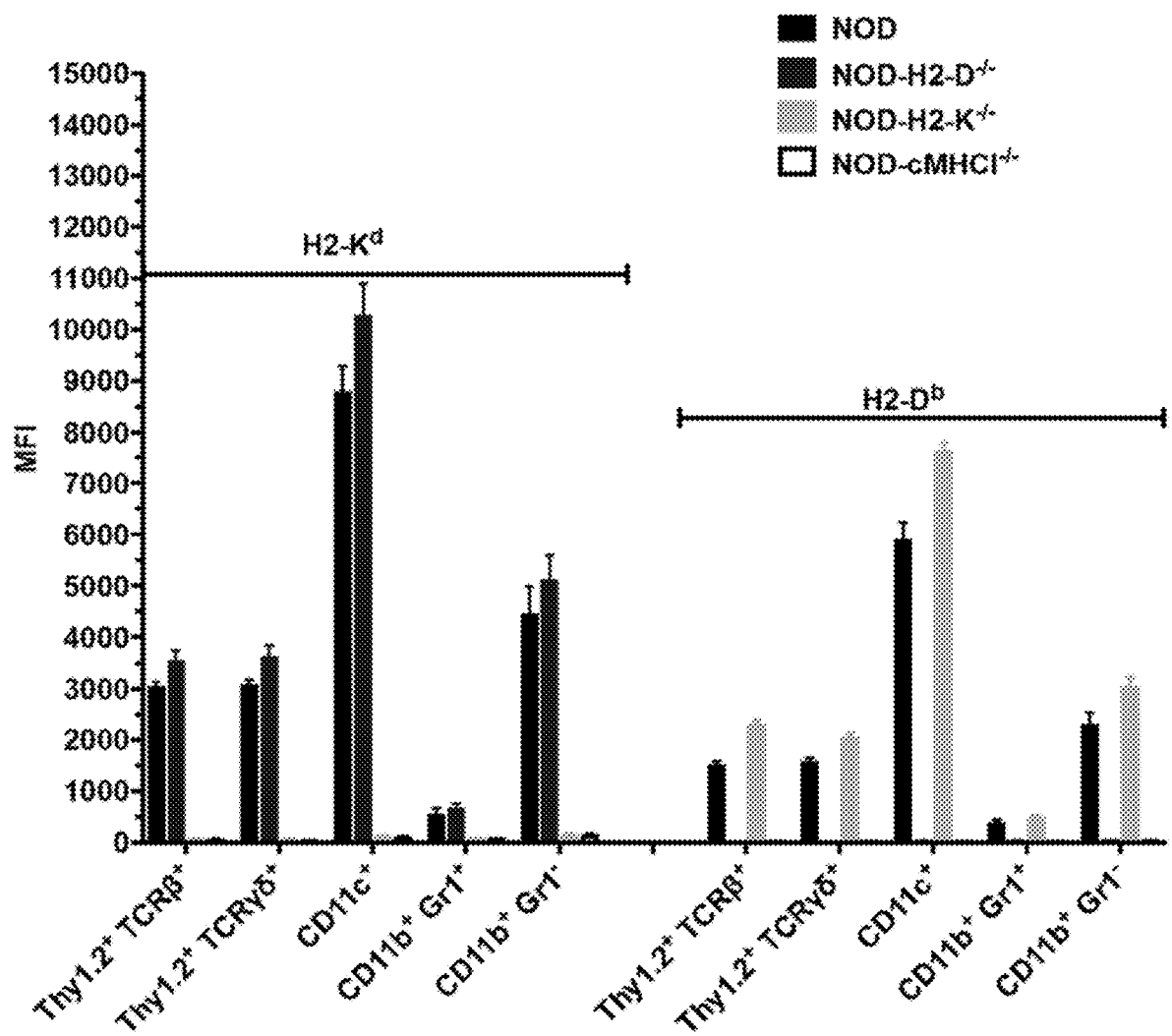
FIG. 9. Validation of H2-K1$^d$ and/or H2-D1$^b$ ablation across other splenic subsets. For NOD-H2-D$^{-/-}$, NOD-H2-K$^{-/-}$, and NOD-cMHCI$^{-/-}$ mice Median Fluorescence Intensity (MFI) of H2-K$^d$ or H2-D$^b$ antibody staining on splenic subsets is shown as Mean±SEM. Data displayed is a separate group of 5-9 mice per strain than the B-cell analyses presented in FIGS. 2, 3 and 4.

Next, we generated NOD-H2-K$^{-/-}$ mice utilizing CRISPR/Cas9 to target exon 3 of H2-K1$^d$. A line carrying a 2 bp deletion within exon 3 (FIG. 3A) was chosen for in-depth analysis based on breeding proclivity. As expected, NOD-H2-K$^{-/-}$ mice lack H2-K, but retain H2-D expression (FIGS. 3B-3C, FIG. 9). In contrast to the NOD-H2-D$^{-/-}$ stock (FIGS. 2D-2E), NOD-H2-K$^{-/-}$ mice showed a small but significant percentage increase in DP and a reduction in CD8$^+$-SP thymocytes (FIGS. 3D-3E) that did not translate to thymic yields (FIG. 3F). However, a more robust change in splenic and PancLN $CD8^+$ T-cells percentage (FIGS. 3G-3H) was observed than in H2-D$^{-/-}$ mice (FIGS. 2G-2H), leading to a drastic reduction in $CD8^+$ T-cells in both organs, along with a slight rise in splenic $CD4^+$ T-cell yields (FIG. 3I).

Figure 4A:
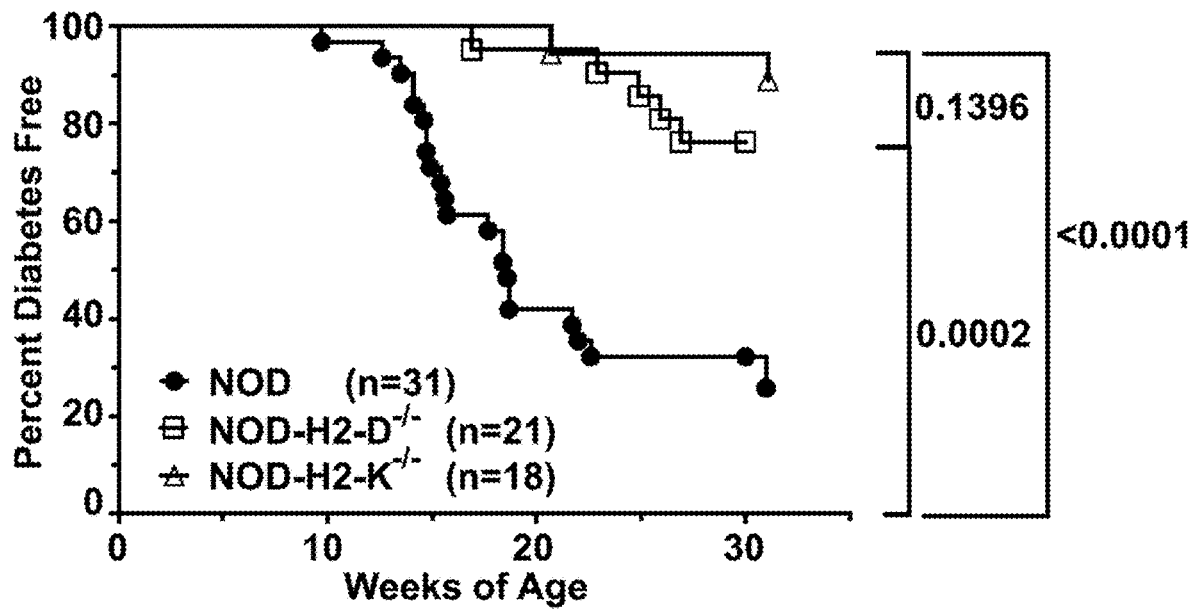
FIGS. 4A-4G. NOD-H2-D$^{-/-}$ and NOD-H2-K$^{-/-}$ have decreased diabetes and insulitis.
Figure 4B:
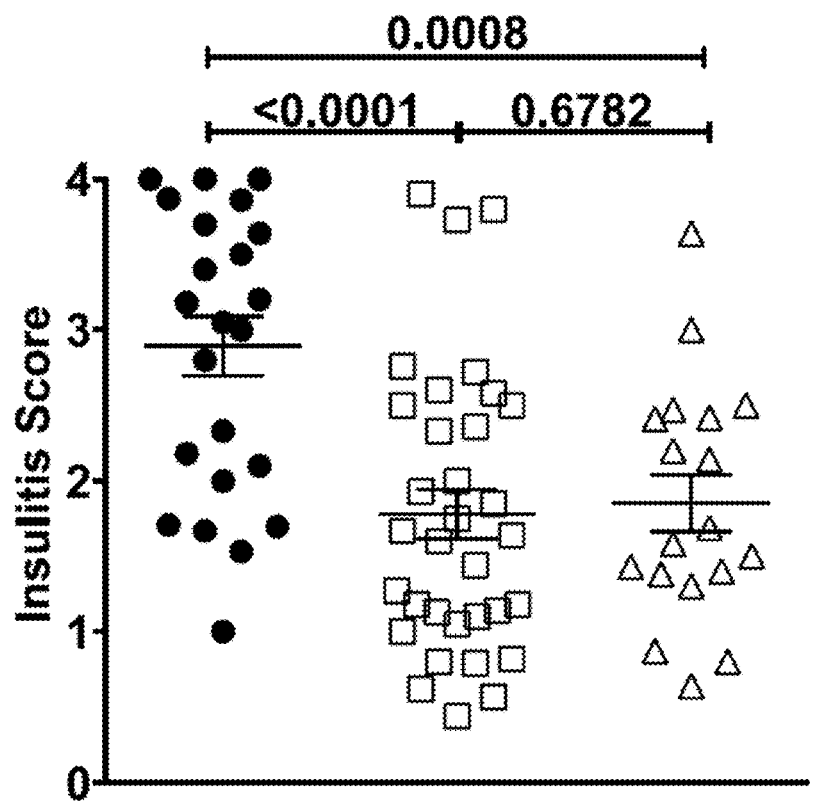
Figure 4C:
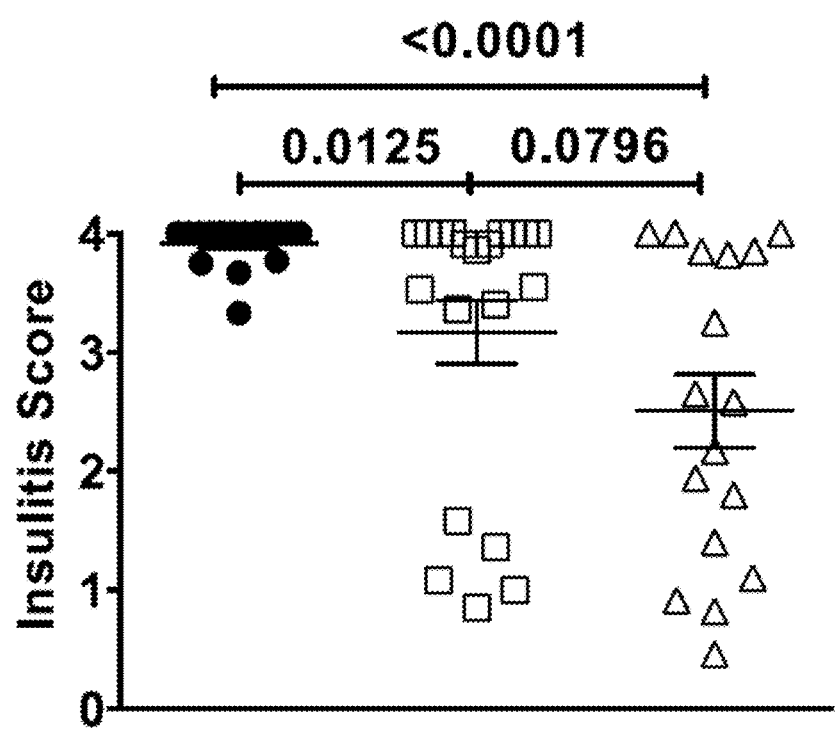
Figure 8A:
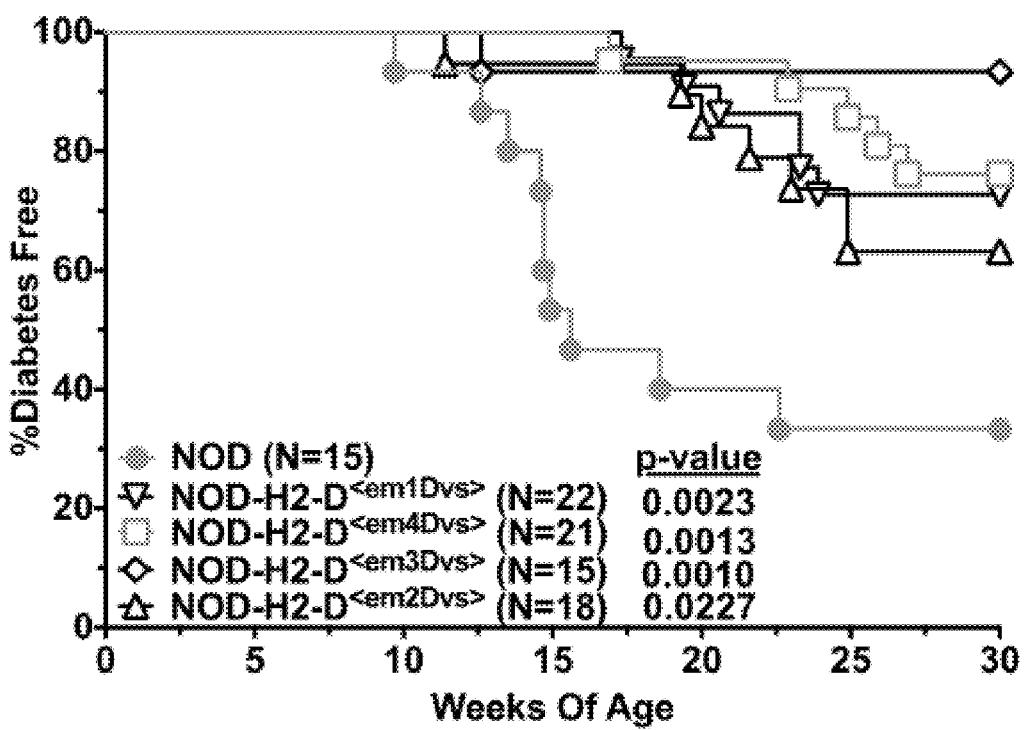
FIGS. 8A-8C. Diabetes incidence (and fate) of additional lines generated during this work. Diabetes incidence of additional knockout lines generated in this work.
Figure 8B:
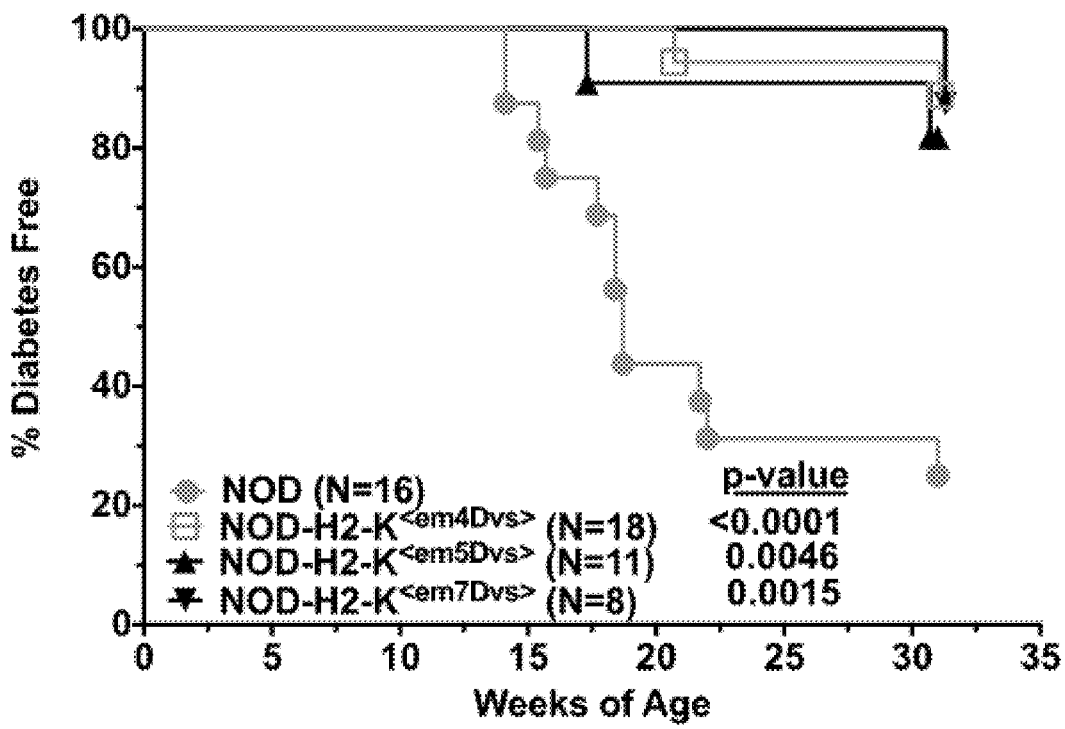

Having generated H2-D$^{-/-}$ and H2-K$^{-/-}$ NOD mice, we assessed the individual contributions of these variants to T1D development. Both NOD-H2-D$^{-/-}$ and NOD-H2-K$^{-/-}$ mice had significantly delayed and reduced T1D development compared to standard NOD controls but did not significantly differ from one another (FIG. 4A). Prior to their cryopreservation, several additional H2-D and H2-K knockout lines were assessed for T1D incidence, showing similar kinetics and penetrance (FIGS. 8A-8B). Additionally, compared to NOD controls, insulitis was decreased in both NOD-H2-D$^{-/-}$ and NOD-H2-K$^{-/-}$ mice at 10-15 weeks of age, as well as at the end of incidence, with no differences between the two groups (FIGS. 4B-4C).

Figure 4D:
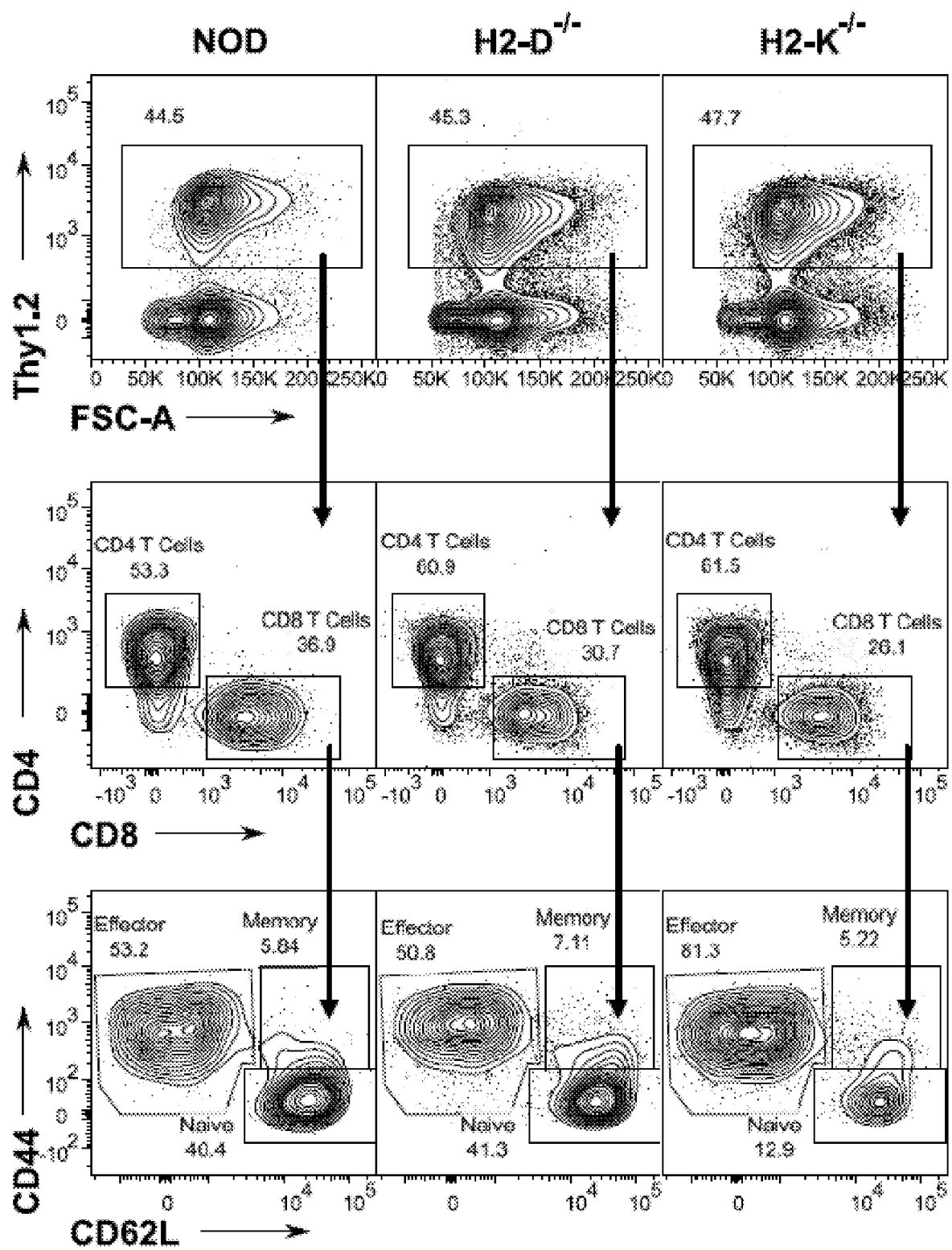
Figure 4E:
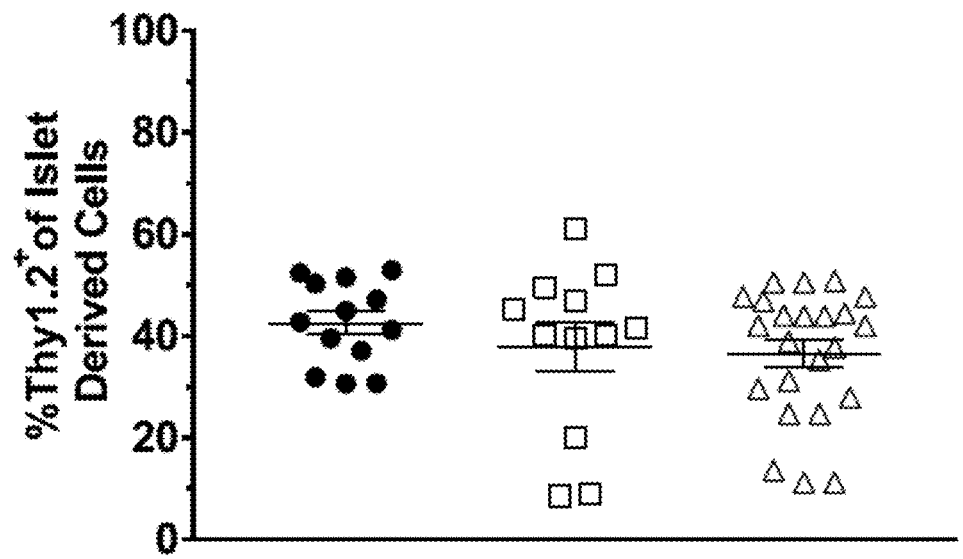
Figure 4F:
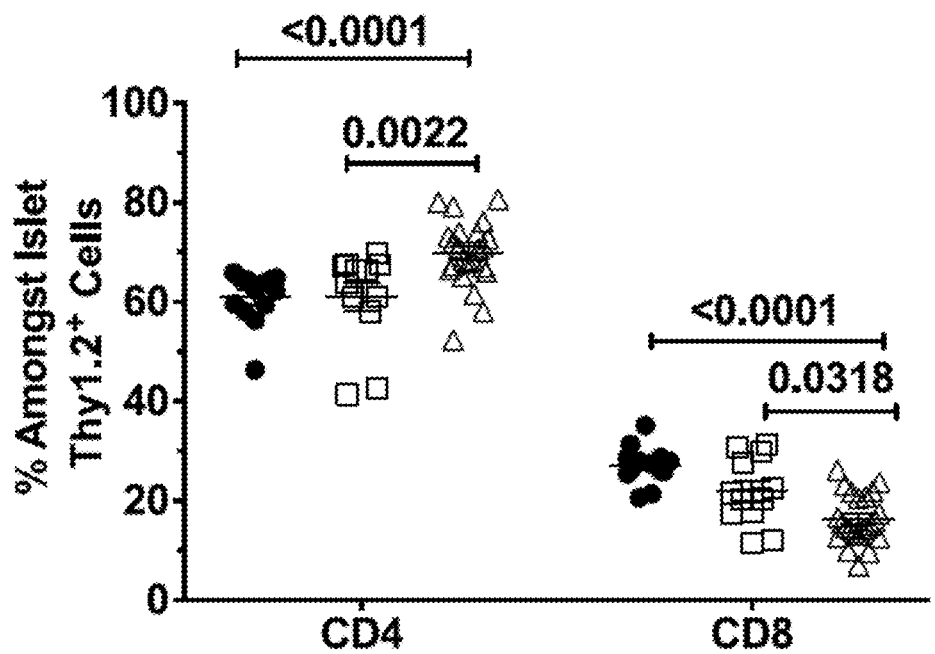
Figure 4G:
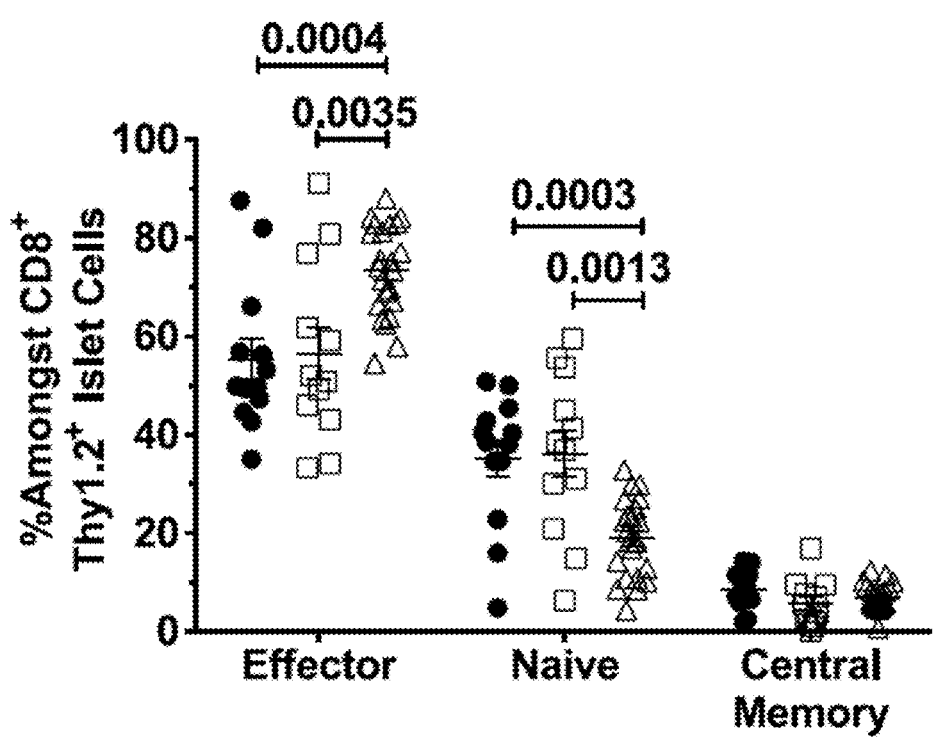

We next examined the makeup of islet infiltrating $CD8^+$ T-cells in NOD-H2-D$^{-/-}$ and NOD-H2-K$^{-/-}$ mice. Amongst islet infiltrating leukocytes, we found no difference in the percentage of T-cells between NOD and the two knockout lines (FIGS. 4D-4E). Interestingly, H2-D$^{-/-}$ mice had similar frequencies of $CD8^+$ T-cells amongst islet-infiltrating T-cells as NOD controls (FIGS. 4D-4F). H2K$^{-/-}$ mice, however, had reduced and increased percentages of $CD8^+$ and $CD4^+$ T-cells, respectively, compared to both NOD and NOD-H2-D$^{-/-}$ mice. Unexpectedly, the frequencies of $CD44^+CD62L^-$ effector $CD8^+$ T-cells but not $CD44^+$ $CD62L^+$ central memory T-cells were increased in H2-K$^{-/-}$ mice compared to both NOD and NOD-H2-D$^{-/-}$ mice, with a concomitant reduction of $CD44^-$ $CD62L^+$ naïve cells (FIG. 4G).

Example 2. Creation of NOD-cMHCI$^{-/-}$ Mice

Figure 5A:
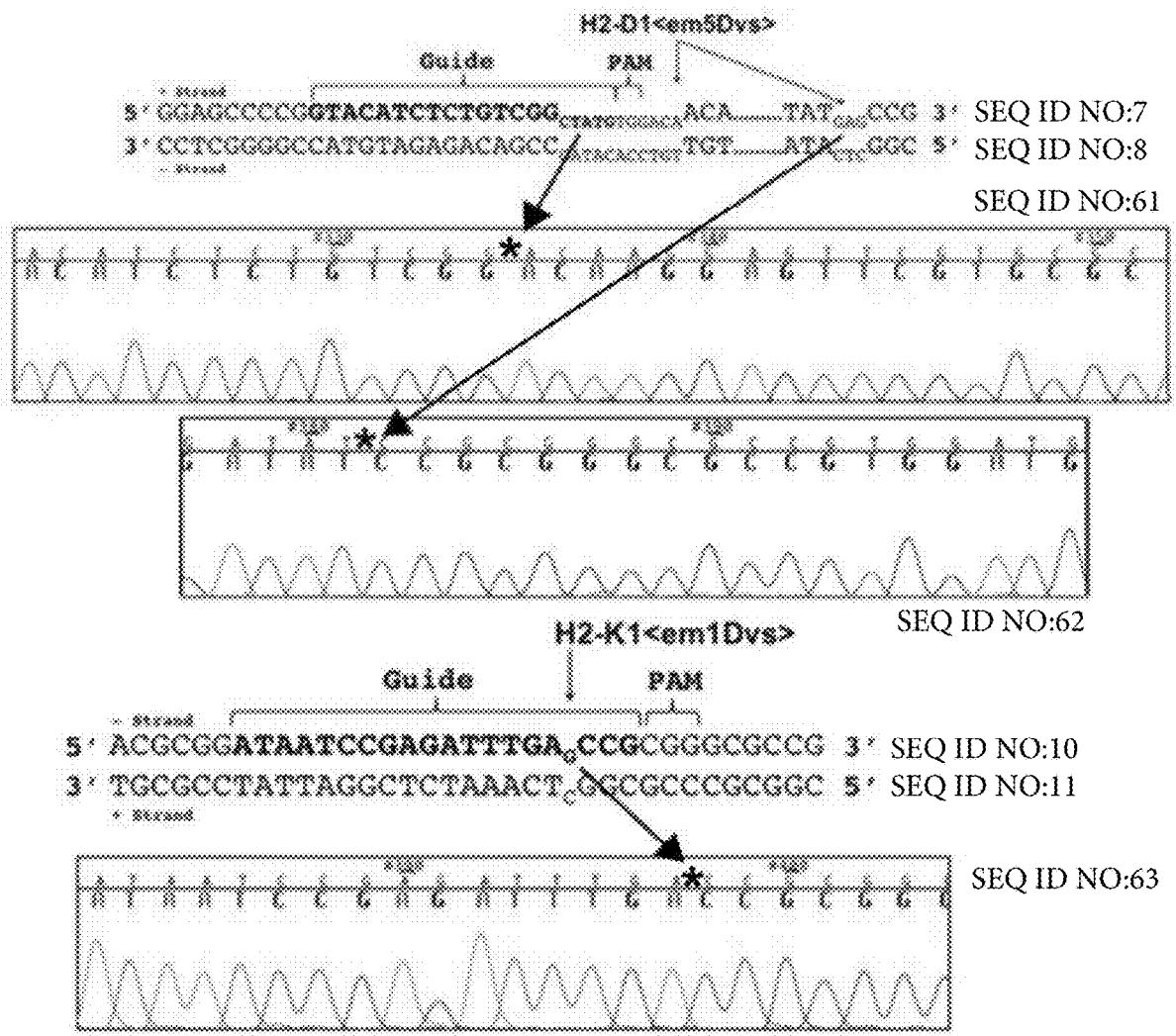
FIGS. 5A-5F. Novel direct-in-NOD H2-D/H2-K double knockout mice generated by CRISPR/Cas9.
Figure 5B:
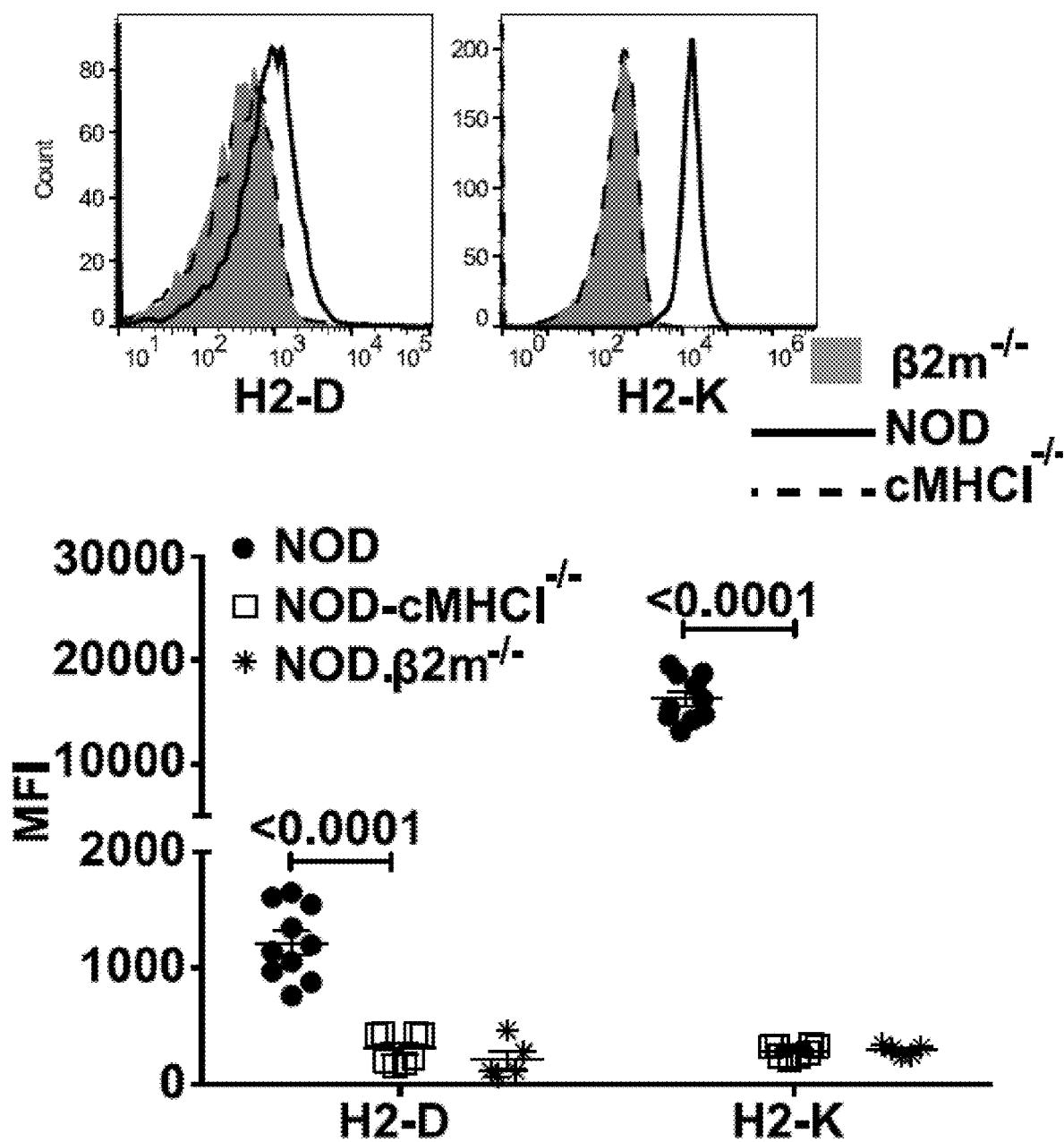
Figure 5C:
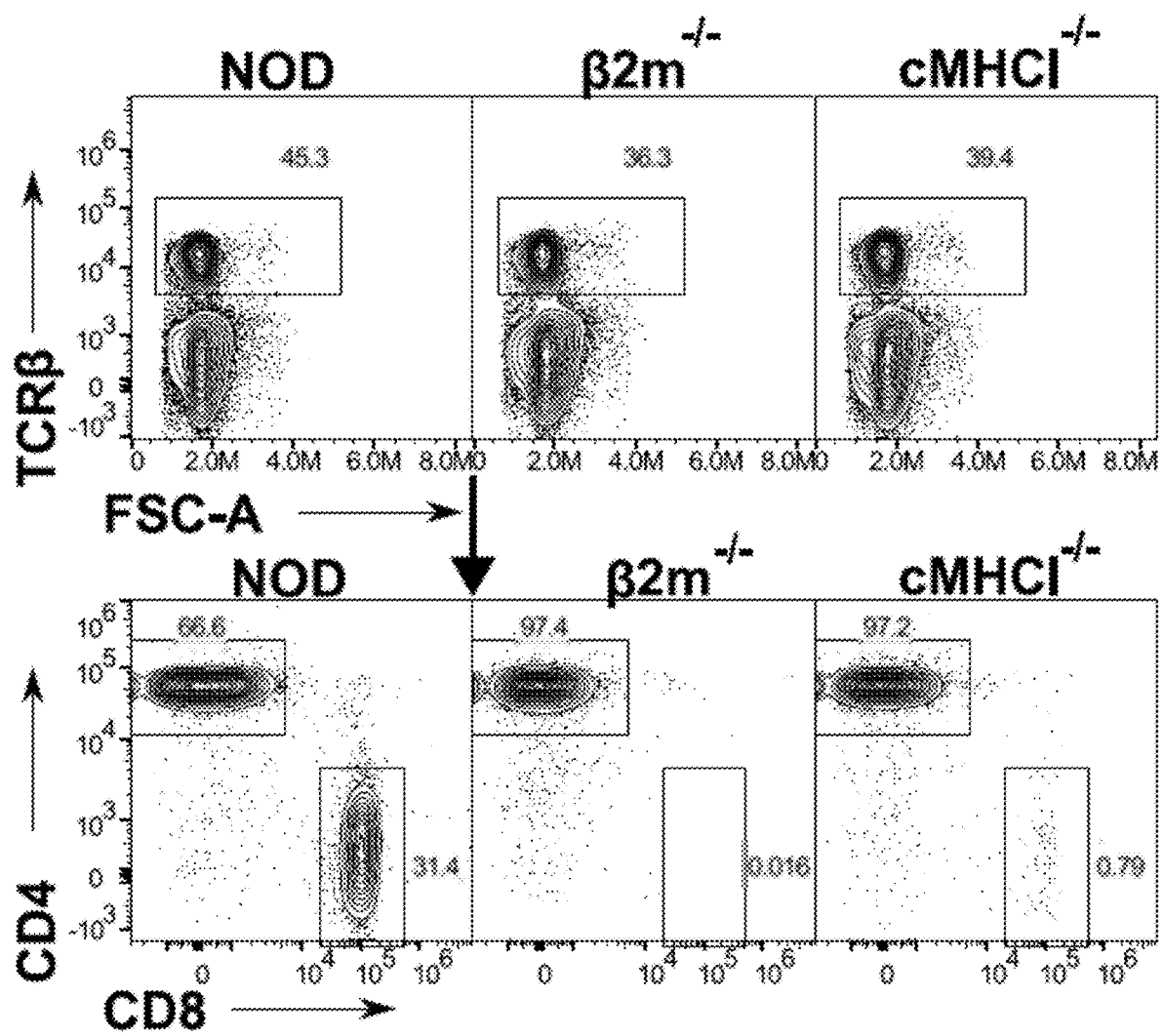
Figure 5D:
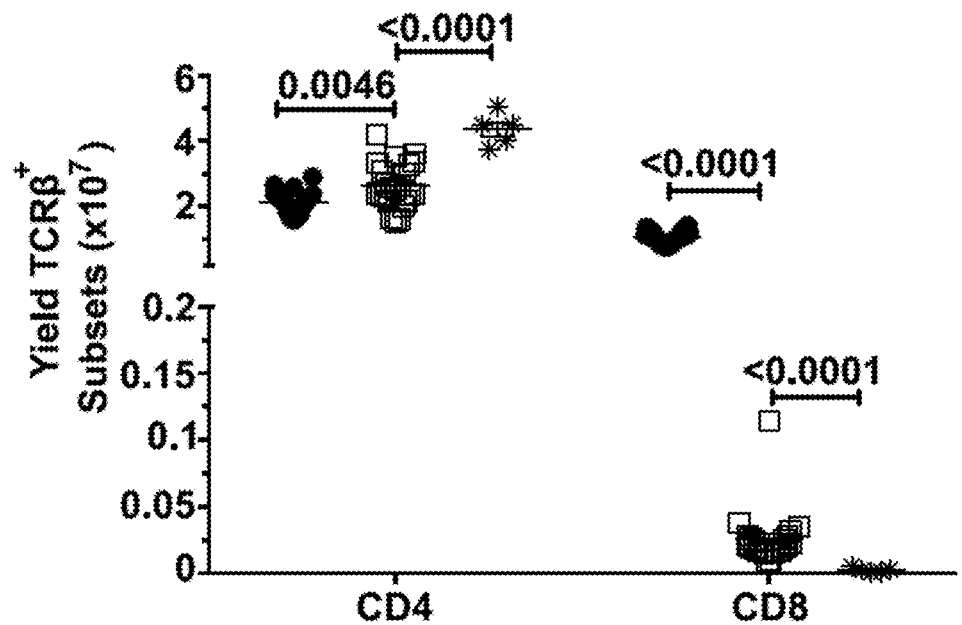
Figure 5E:
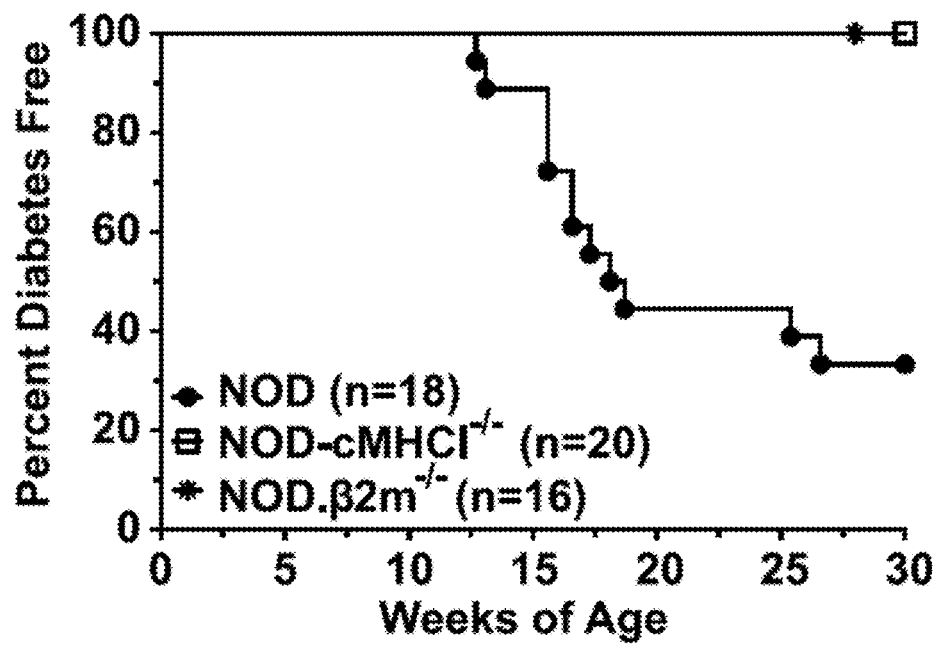
Figure 5F:
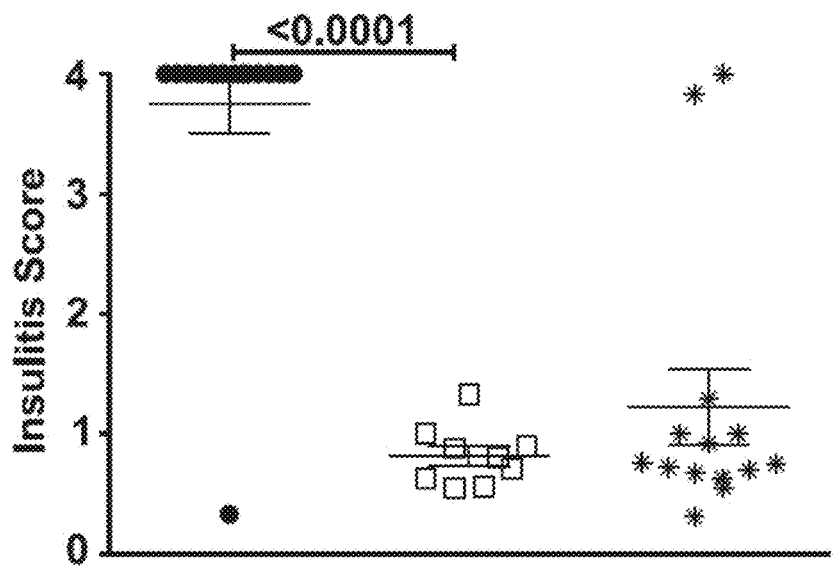
Figure 8C:
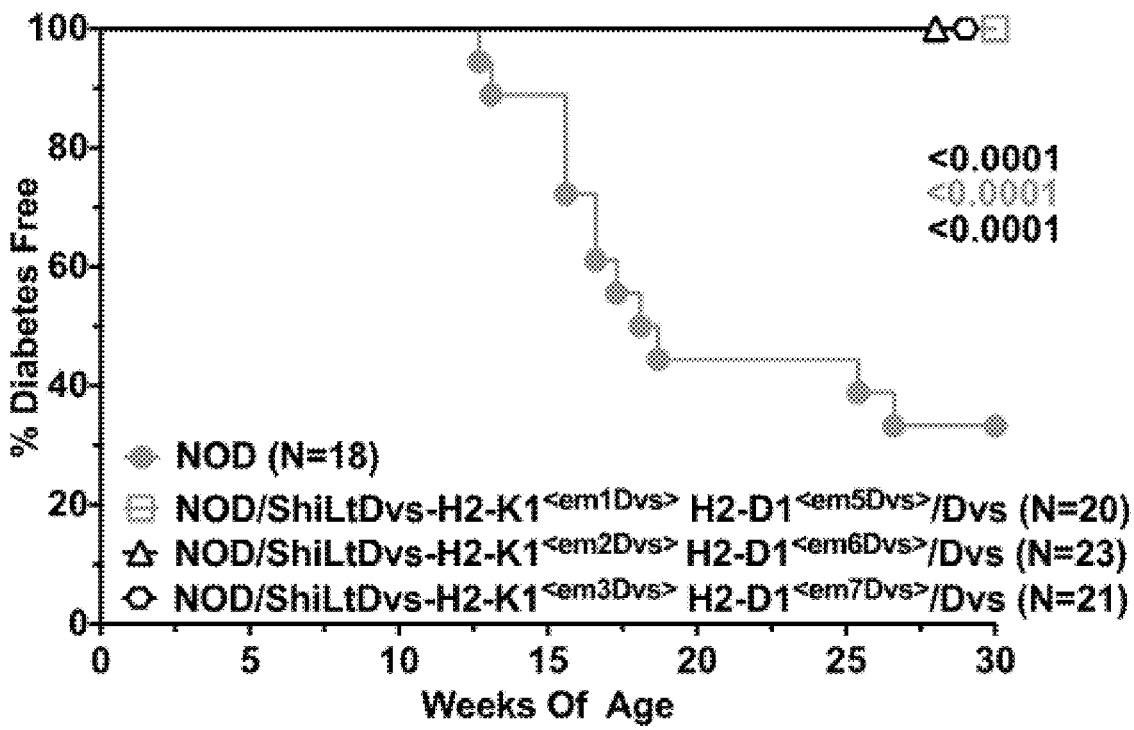

We next simultaneously targeted H2-D1$^b$ and H2-K1$^d$ to generate NOD mice directly lacking expression of both classical murine MHC class I molecules. Three founders were generated carrying predicted frameshift mutations within exon 2 of H2-D1$^b$ and H2-K1$^d$ (FIG. 5A, and data not shown). Based on breeding proclivity we selected a NOD-cMHCI$^{-/-}$ line carrying spaced 11 and 3 bp deletions within H2-D1 and a 1 bp deletion in H2-K1 (FIG. 5A) for analyses. As expected, these NOD-cMHCI$^{-/-}$ mice lack H2-D and H2-K (FIG. 5B, FIG. 9). This lack of MHC I expression corresponded with a paucity of splenic CD8$^+$ TCRβ$^+$ cells (FIGS. 5C-5D). Due to the ability of the NOD-cMHCI$^{-/-}$ stock to express non-classical MHC Ib molecules, they were characterized by small, but significant increase in the yield of splenic CD8$^+$ T-cells compared to NOD.β2m$^{-/-}$ mice (FIGS. 5C-5D). Compared to standard NOD controls, both NOD-cMHCI$^{-/-}$ and NOD.β2m$^{-/-}$ mice had increased CD4$^+$ yields, with this elevation greatest in the latter stock (FIG. 5D). Similar to NOD.β2m$^{-/-}$ mice, NOD-cMHCI$^{-/-}$ mice were resistant to T1D (FIG. 5E, FIG. 8C) and insulitis out to thirty weeks of age (FIG. 5F).

Figure 6A:
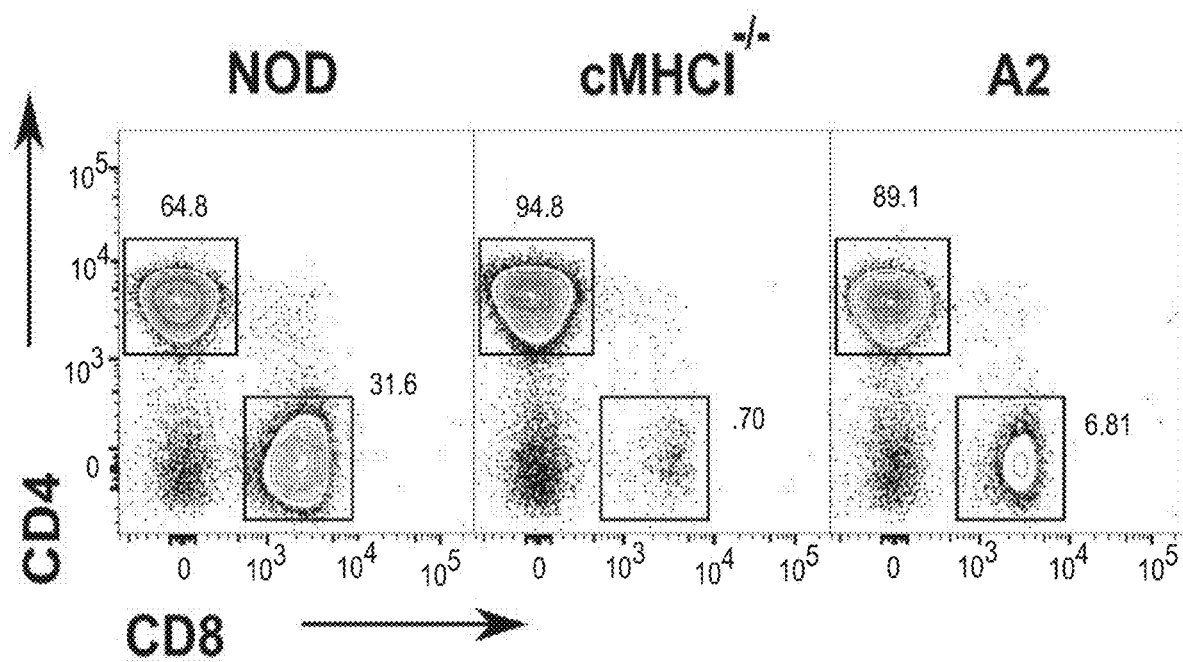
Figure 6B:
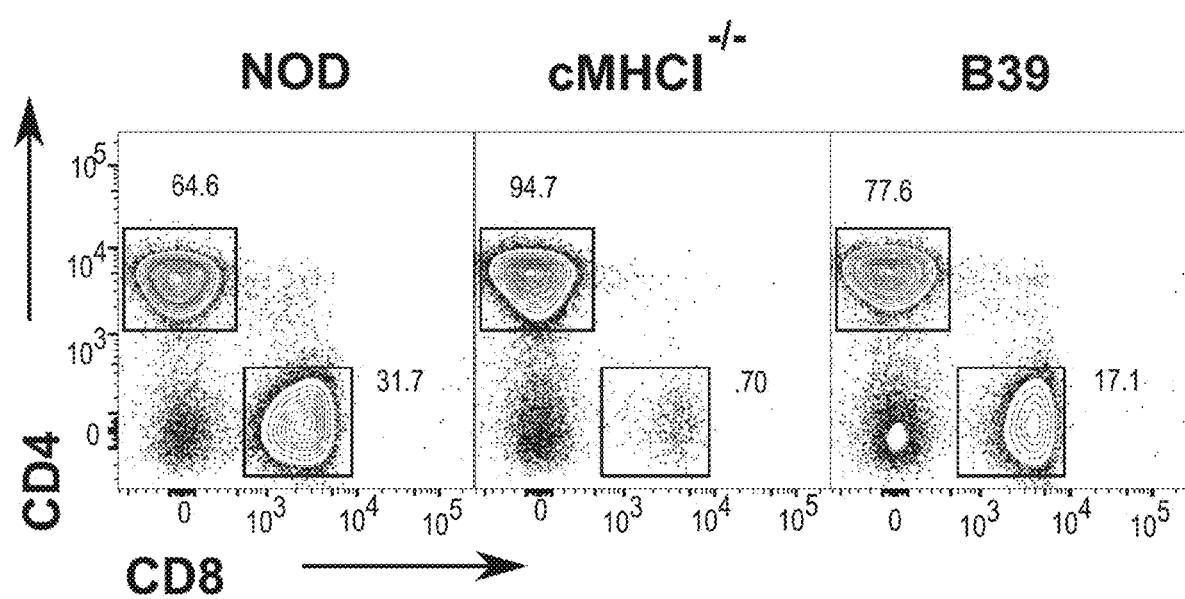
Figure 6H:
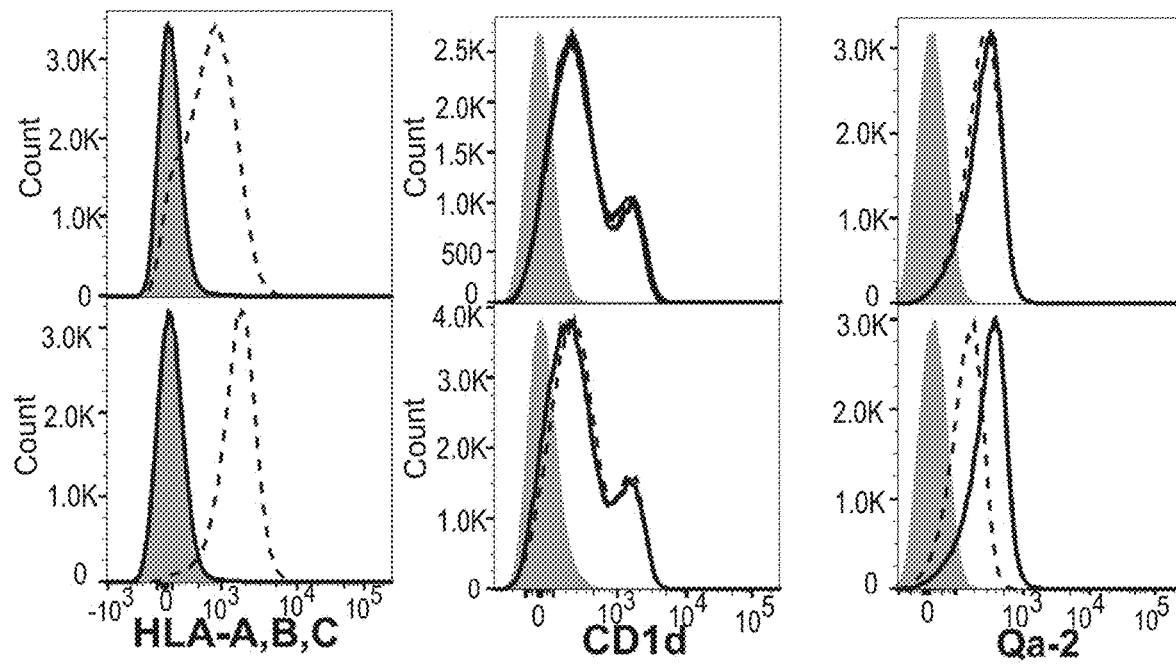
Figure 6H:
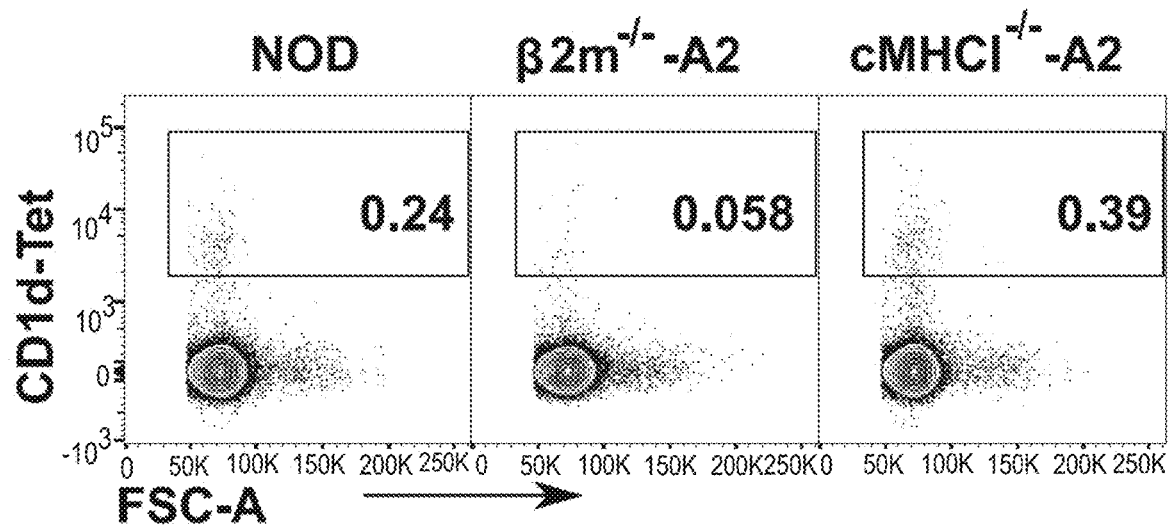
Figure 6I:
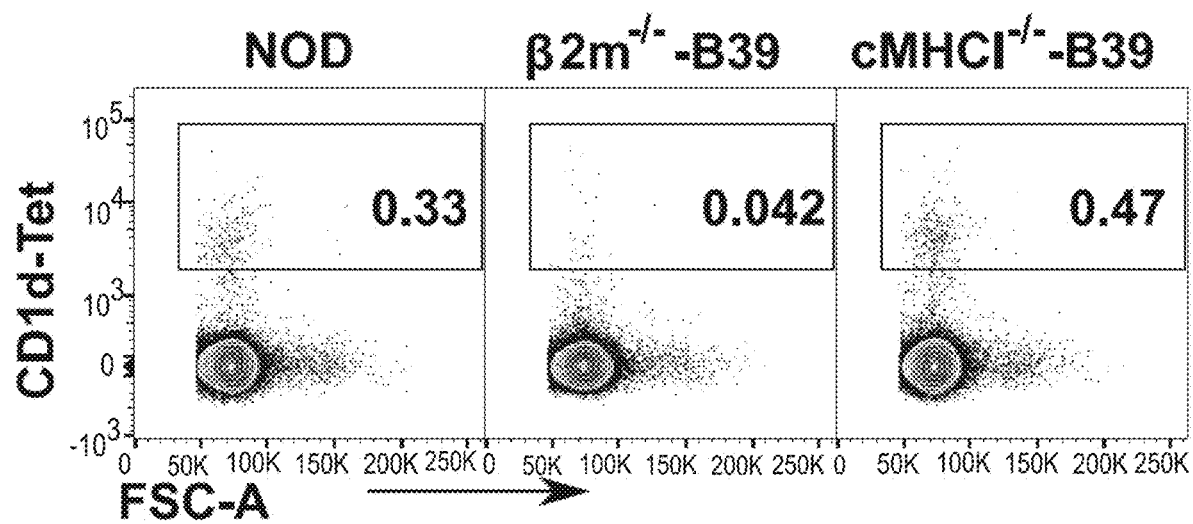
Figure 6J:
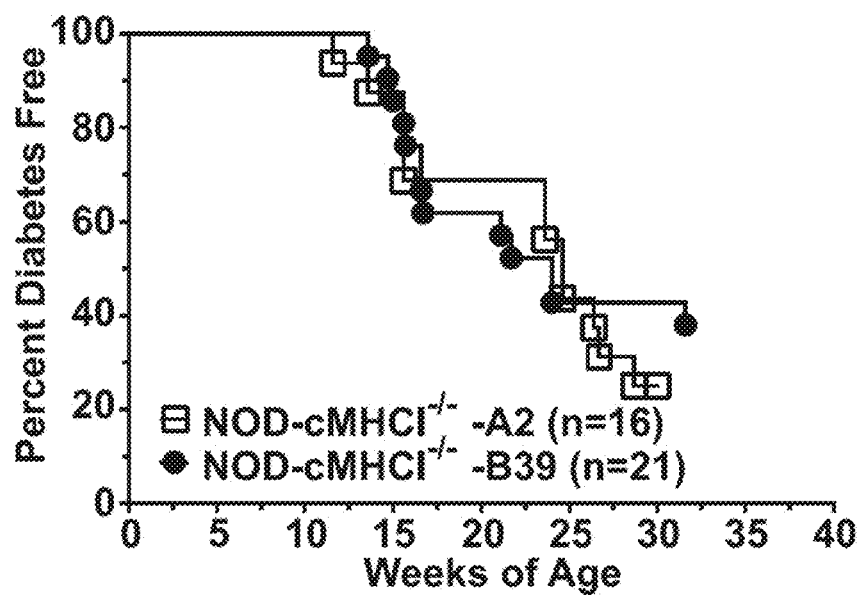
Figure 6K:
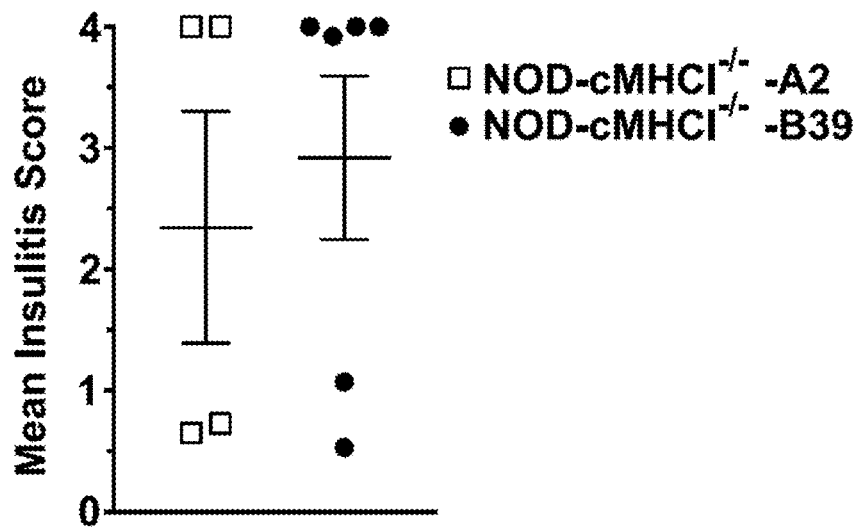

Example 3. Second Generation NOD-cMHCI$^{-/-}$-A2 and NOD-cMHCI$^{-/-}$-B39 Mice To test if it could be used as a new base model for HLA-"humanization" in lieu of stocks carrying the β2m$^{-/-}$ mutation, we crossed NOD-A2 and NOD-B39 mice with the newly created NOD-cMHCI$^{-/-}$ line. Like their earlier NOD.β2m$^{-/-}$ counterparts, NOD-cMHCI$^{-/-}$ mice carrying A2-(FIG. 6A) or B39-(FIG. 6B) encoding transgenes have CD8$^+$ T-cells. Also, similar to the earlier NOD.β2m$^{-/-}$ platform, NOD-cMHCI$^{-/-}$-HLA mice express their respective HLA-transgenes, but not murine H2-D and H2-K class I molecules (FIGS. 6C-6E). However, unlike their NOD.β2m$^{-/-}$ counterparts, NOD-cMHCI$^{-/-}$-A2 and NOD-cMHCI$^{-/-}$-B39 mice express non-classical CD1d and Qa-2 (although for unknown reasons at different levels in the transgenics FIG. 10) class I molecules (FIGS. 6F-6G). One functional consequence of this is that NOD-cMHCI$^{-/-}$-HLA class I mice have CD1d-restricted NKT cells (FIGS. 6H-6I) a population whose therapeutic expansion could provide a means for T1D inhibition (42-44). Finally, T1D development and insulitis in both NOD-cMHCI$^{-/-}$-A2 and NOD-cMHCI$^{-/-}$-B39 mice is highly penetrant (FIGS. 6J-6K).

Figure 6L:
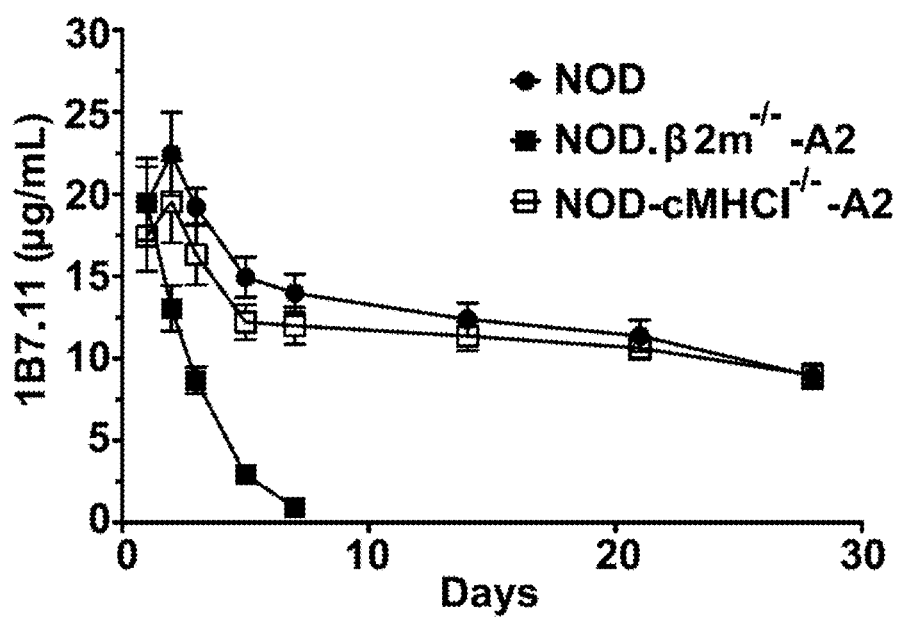
Figure 6M:
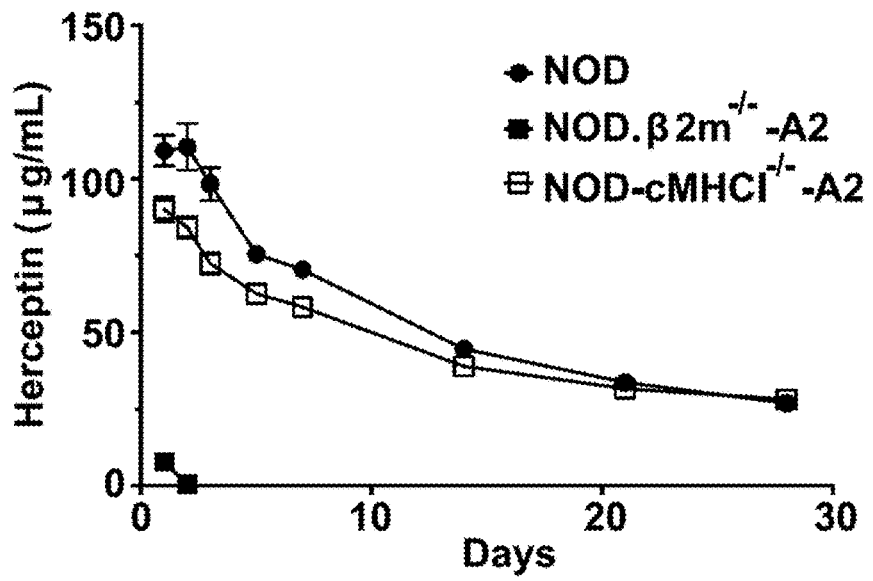

Next, we determined whether FcRn functionality was restored in NOD-cMHCI$^{-/-}$-HLA class I mice. NOD, NOD.β2m$^{-/-}$-A2 and NOD-cMHCI$^{-/-}$-A2 were injected with mouse TNP-specific antibody 1B7.11 (FIG. 6L) or humanized Herceptin IgG1 antibody (FIG. 6M). As expected, murine 1B7.11 antibody was cleared within a week in NOD.β2m$^{-/-}$-A2 mice (FIG. 6L). NOD-cMHCI$^{-/-}$-A2 and NOD mice both retained detectable 1B7.11 antibody out to thirty days post-injection (FIG. 6L). Injected Herceptin was rapidly cleared in NOD.β2 m$^{-/-}$-A2 mice, but was retained at detectable levels out to 30 days in both NOD and NOD-cMHCI$^{-/-}$-A2 mice (FIG. 6M). These data indicate NOD-cMHCI$^{-/-}$-HLA mice retain FcRn functionality.

Example 4. Creation of NOD-cMHCI/II$^{-/-}$ Mice

Figure 7A:
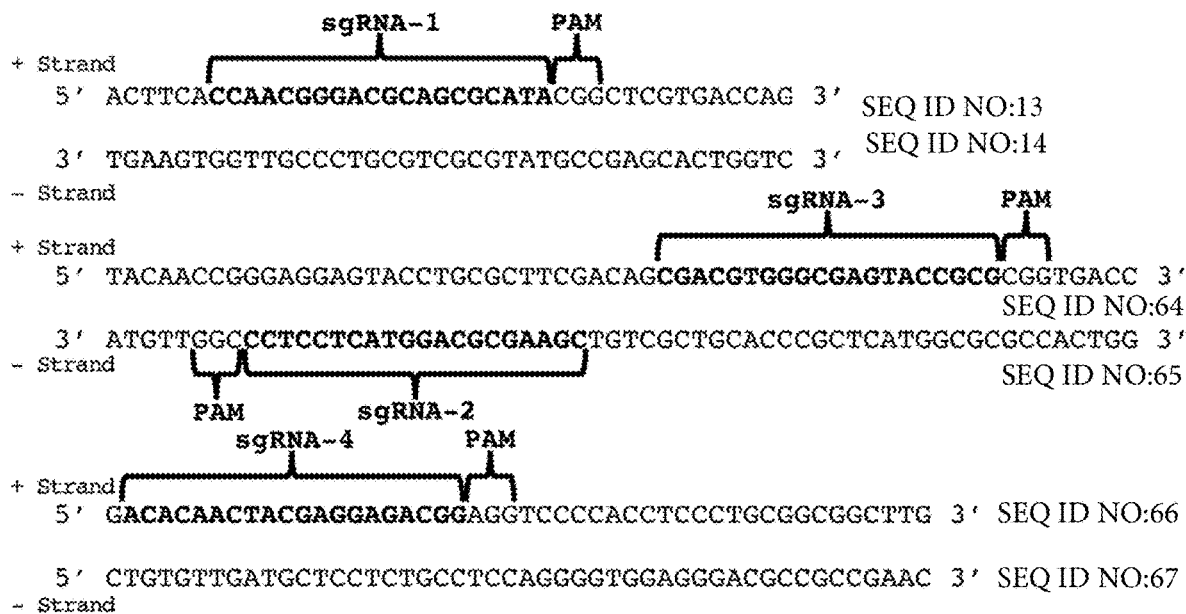
Figure 7D:
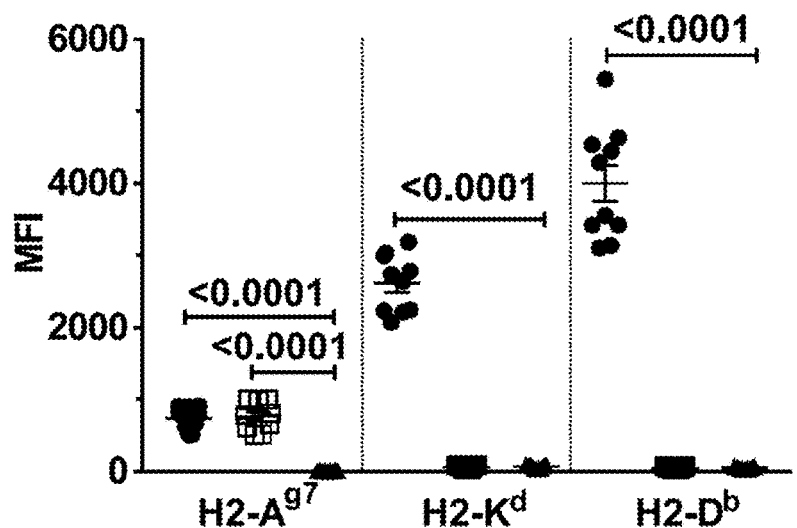
Figure 7E:
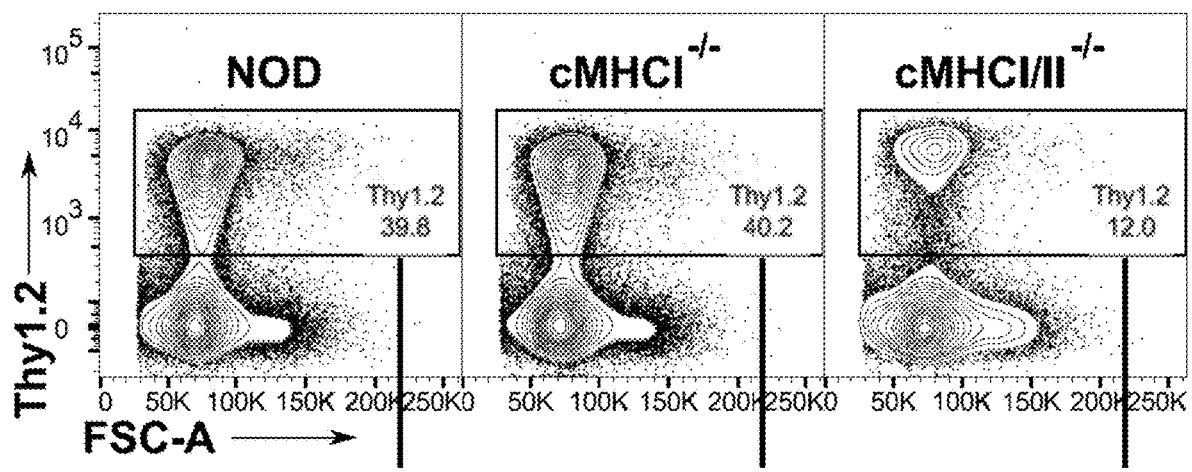
Figure 7F:
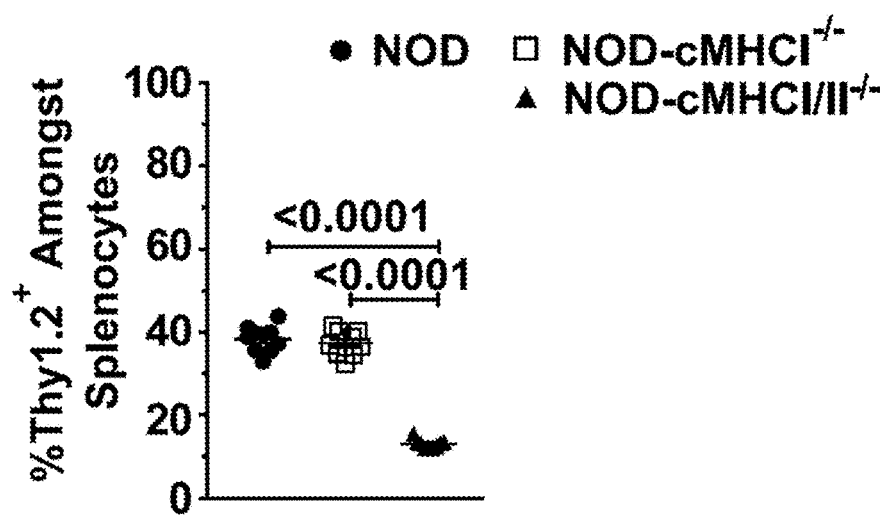
Figure 7G:
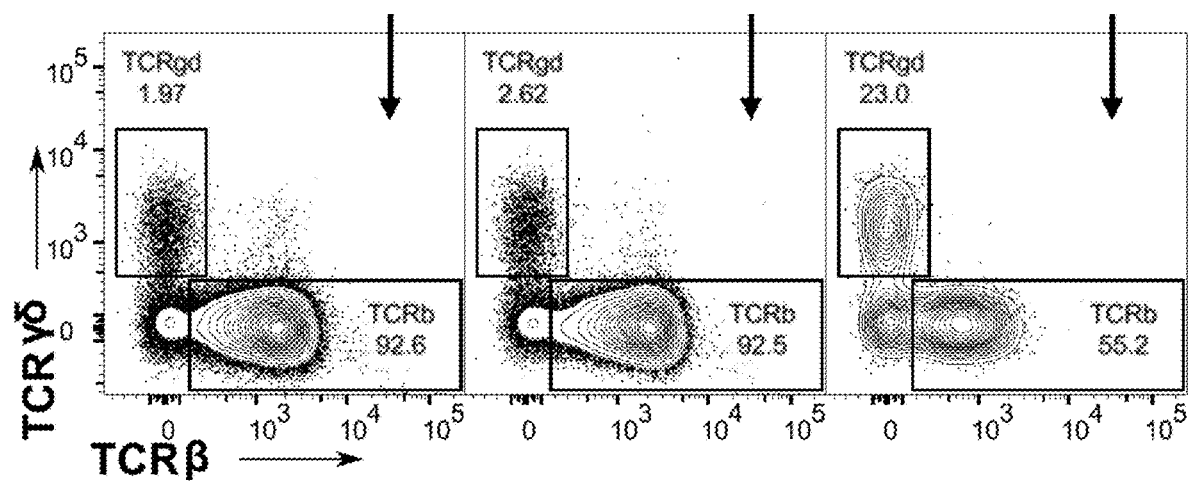
Figure 7H:
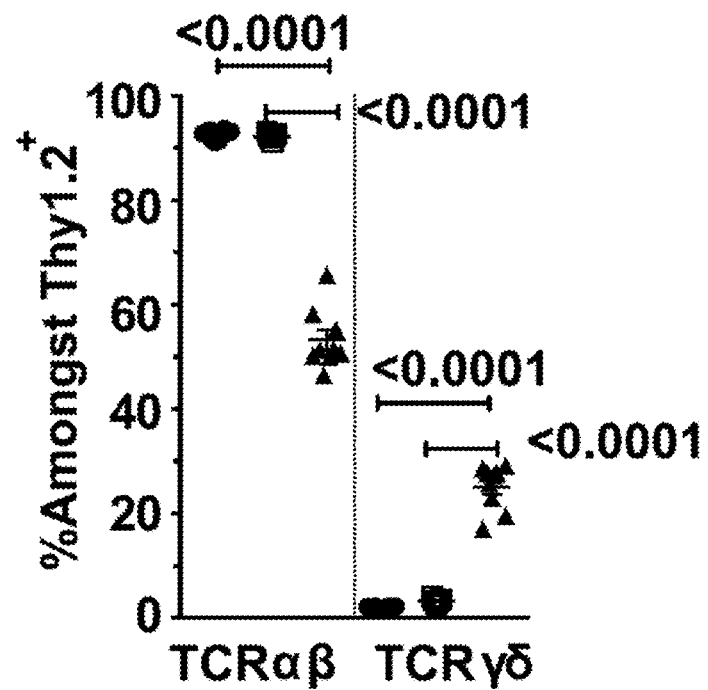
Figure 7I:
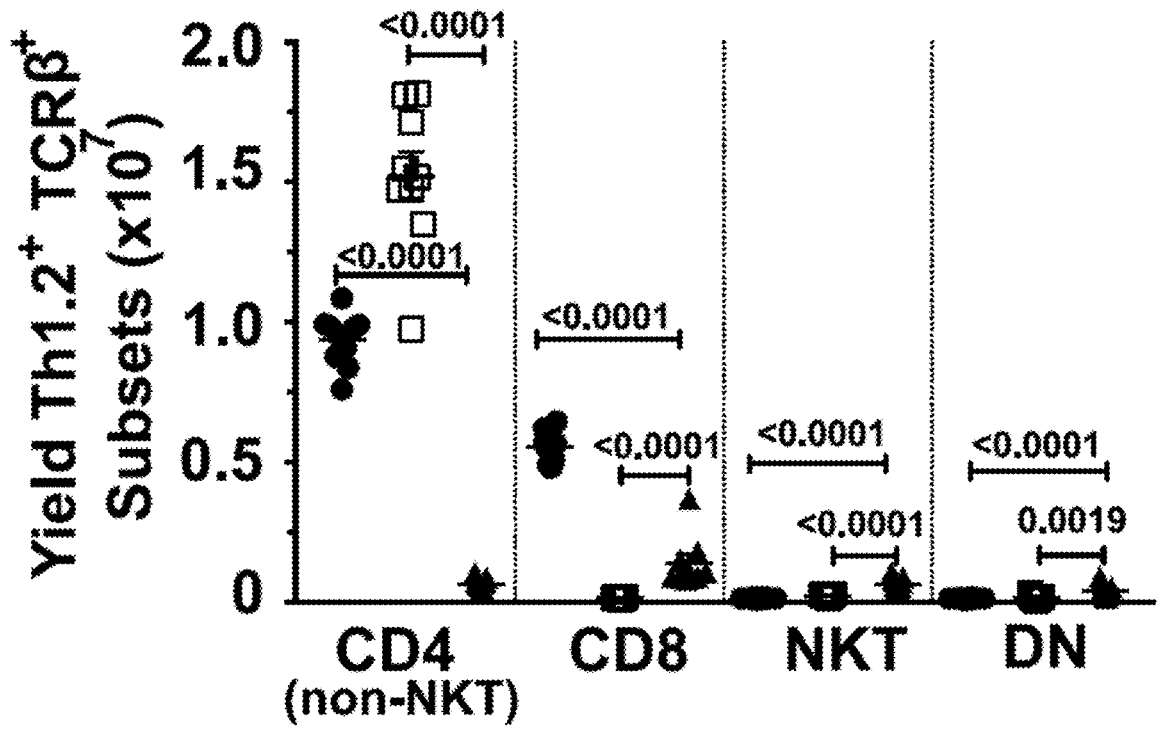
Figure 7J:
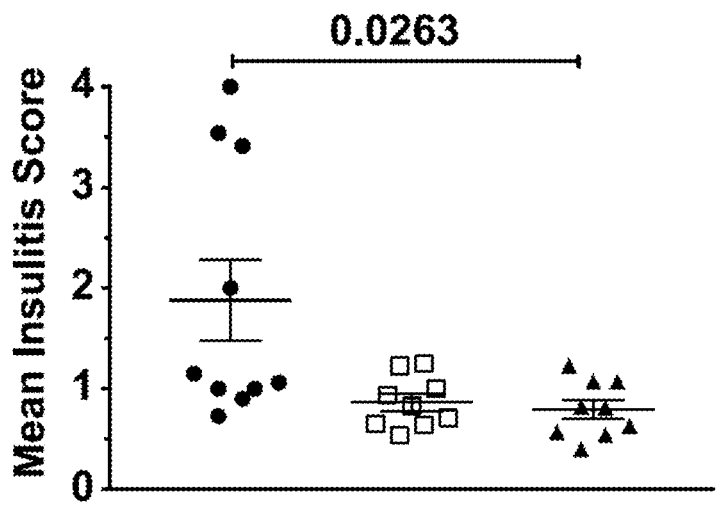
Figure 11A:
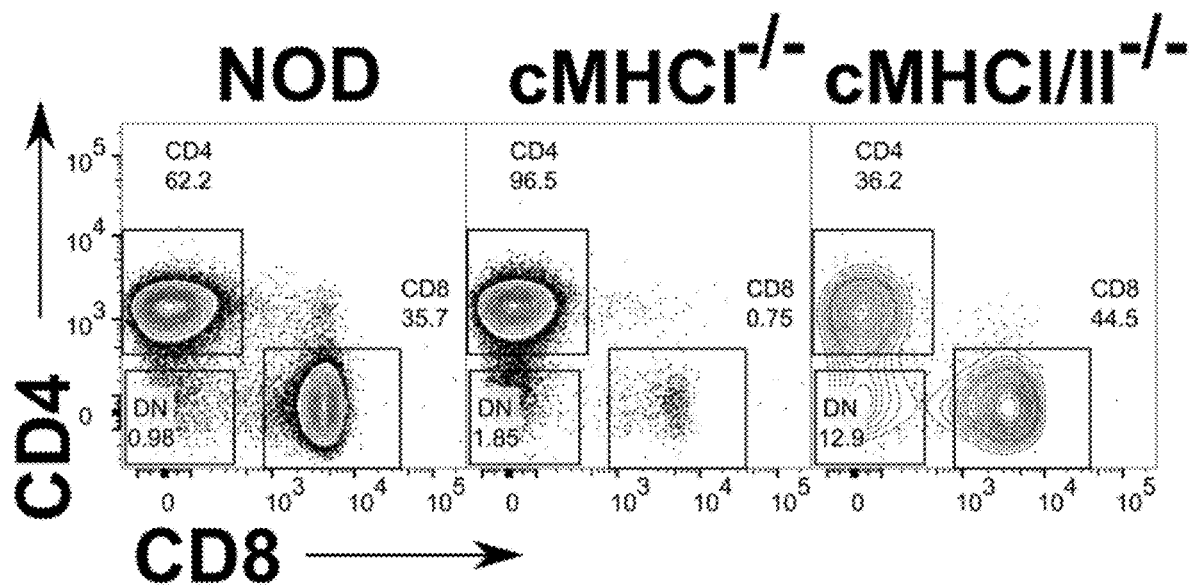
FIGS. 11A-11B. T-cell subsets in NOD-cMHCI/II$^{-/-}$ mice.
Figure 11B:
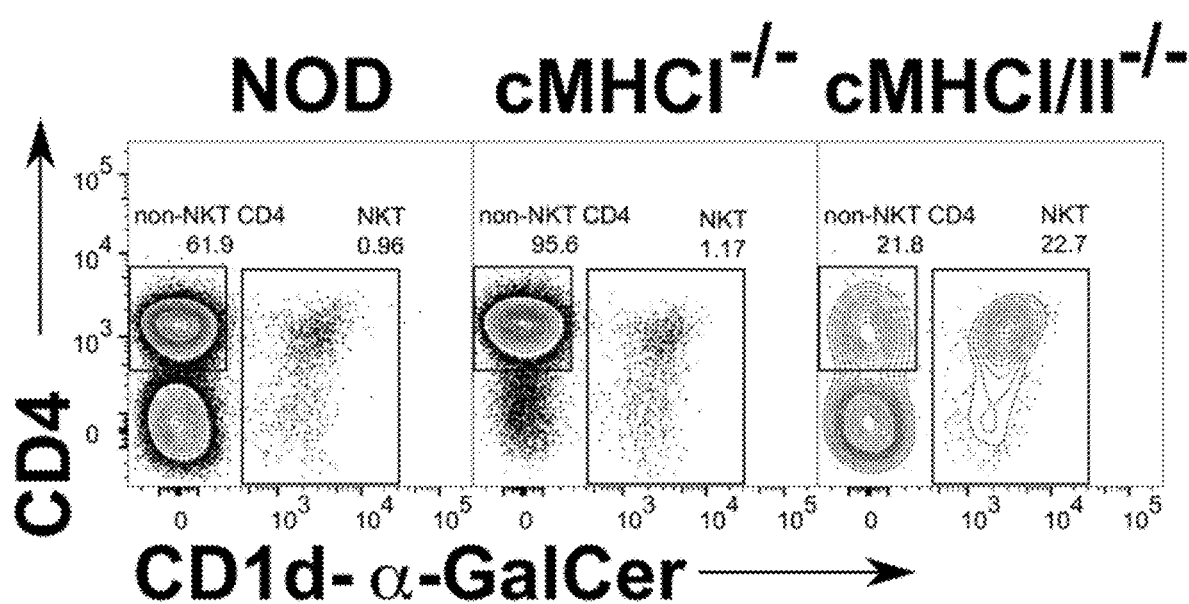

Further advancement of humanized NOD models would incorporate relevant combinations of both HLA class I and II susceptibility alleles. Towards this end, we generated NOD mice completely lacking in expression of classical murine MHC molecules (NOD-cMHCI/II$^{-/-}$) mice by CRISPR/Cas9 targeting exon 2 of H2-Ab1$^{g7}$ in the NOD-cMHCI$^{-/-}$ stock (FIG. 7A). This resulted in an 181 bp deletion within exon 2 of H2-Ab1$^{g7}$ (FIG. 7B). As expected, NOD-cMHCI/II$^{-/-}$ mice lack expression of H2-A$^{g7}$, H2-K, and H2-D (FIGS. 7C-7D). Thy1.2$^+$ cells were reduced to ~12% of total splenocytes in NOD-cMHCI/II$^{-/-}$ mice (FIGS. 7E-7F). Amongst residual Thy1.2$^+$ cells, TCRαβ$^+$ cells were reduced to 60% with a concomitant increase in the percentage of TCRγδ cells (FIGS. 7G-7H). Amongst residual TCRαβ$^+$ cells, the yield of CD4$^+$ T-cells was drastically reduced compared to both NOD and NOD-cMHCI$^{-/-}$ mice (FIG. 11A, FIG. 7I). The yield of CD8$^+$ T-cells was reduced compared to NOD mice, but expanded compared to NOD-cMHCI$^{-/-}$ mice (FIG. 11A, FIG. 7I). CD4+ and CD8$^+$ double negative (FIG. 11A) and NKT-cells (FIG. 11B) were both slightly expanded in NOD-cMHCI/II$^{-/-}$ mice in comparison to NOD and NOD-cMHCI$^{-/-}$ mice (FIG. 7I). Finally, when examined at nine-twelve weeks of age NOD-cMHCI/II$^{-/-}$ mice were virtually free of insulitis (FIG. 7J).

Methods

Mice—General

NOD/ShiLtDvs (hereafter NOD) (Simecek P. et al. G3: GENES, GENOMES, GENETICS, 2015, doi.org/10.1534/g3.115.017046) and all other mouse strains described herein are maintained at The Jackson Laboratory under specific pathogen-free conditions. NOD-Tg(HLA-A/H2-D/B2M)1Dvs/Dvs (commonly called NOD-HHD, hereafter NOD-A2), NOD.Cg-B2m$^{<tm1Unc>}$ Tg(HLA-A/H2-D/B2M)1Dvs/Dvs (hereafter NOD.β2 m$^{-/-}$-A2), NOD.129P2(B6)-B2m$^{<tm1Unc>}$ (hereafter NOD.β2m$^{-/-}$), and NOD/ShiLtDvs-Tg(HLA-B39/H2-D/B2M)2Dvs/Dvs (hereafter NOD-B39) have been previously described (11; 21; 31).

Mouse Model Development

NOD zygotes were injected with 100 ng/μL Cas9 mRNA and 50 ng/μL sgRNA containing specific guide sequences for the targeted gene and described in more detail in the figure legends. Mosaic founders were crossed back to the NOD background for at least one generation and resulting offspring analyzed for mutations using the procedures detailed below.

Genotyping NOD-H2-D$^{-/-}$

PCR amplification of exon 1 and 2 of H2-D1$^b$ was performed with Batch 1: forward primer 5'-TCAGACACCCGGGATCCCAGATGG-3' (SEQ ID NO:23) and reverse primer 5'-CGCGCTCTGGTTGTAGTAGCCGAG-3' (SEQ ID NO:24) or Batch 2 forward primer 5'-GGCGAGATTCCAGGAGCCAA-3' (SEQ ID NO:25) and reverse primer 5'-TTCCGGGTCCGTTCTGTTCC-3' (SEQ ID NO:26). Sequencing for Batch 1 was performed with reverse primer 5'-CAGGTTCCTCAGGCTCACTC-3' (SEQ ID NO:27) or 5'-TTTCCCGCTCCCAATACTC-3' (SEQ ID NO:28). Sequencing primer for Batch 2 was performed with either the two reverse sequencing primers from Batch 1, or with Batch 1's forward primer. Zygosity was determined by restriction length polymorphisms using the above Batch 2 primers as the mutation described herein disrupts an XhoI restriction site within exon 2 (data not shown).

Genotyping NOD-H2-K$^{-/-}$

PCR amplification of Exon 2 and 3 of H2-K1$^d$ was performed using forward primer 5'-ATTCGCTGAGGTATTTCGTC-3' (SEQ ID NO:29) and reverse primer 5'-TTCTCTCCTTCCCTCCTGAGAC-3' (SEQ ID NO:30). Sequencing was performed using forward primer 5'-CCCGGAACCGGTTTCCCTTT-3' (SEQ ID NO:31). Homozygosity was confirmed by flow cytometry showing a lack of H2-K expression on blood B-cells.

Genotyping NOD-cMHCI$^{-/-}$

Sequencing of H2-D1$^b$ was performed as described above. In order to sequence H2-K1$^d$, a PCR product spanning most of exon 1 and 2 was amplified using forward primer 5'-AGTCGCTAATCGCCGACCAGT-3' (SEQ ID NO:32) and reverse primer 5'-CGGGAAGTG-GAGGGGTCGTG-3' (SEQ ID NO:33). These primers were also used for sequencing. Homozygosity was additionally typed by flow cytometry analysis of peripheral blood B220$^+$ cells showing a lack of H2-K and H2-D.

NOD-cMHCI$^{-/-}$-A2 and NOD-cMHCI$^{-/-}$-B39

NOD-A2 or NOD-B39 mice were crossed to NOD-cMHCI$^{-/-}$ mice. Resulting offspring were backcrossed to NOD-A2 or NOD-B39 mice. Offspring were selected for homozygosity of A2 or B39 transgenes. For qPCR analysis of the B39 transgene, forward primer 5'-GGAGACACG-GAAAGTGAAGG-3' (SEQ ID NO:34), reverse primer 5'-GGCCTCGCTCTGGTTGTAG-3' (SEQ ID NO:35) and transgene probe 5'-6-FAM CCGAGTGGACCTGGGGACCC Black Hole Quencher 1-3' (SEQ ID NO:36) were used. Internal control forward primer 5'-CACGTGGGCTCCAGCATT-3' (SEQ ID NO:37), reverse primer 5'-TCACCAGTCAT-TTCTGCCTTTG-3' (SEQ ID NO:38) and control probe 5'-Cy5-CCAATGGTCGGGCACTGCTCAA Black Hole Quencher 2-3' (SEQ ID NO:39) were also used. The specific qPCR conditions for the HHD transgene are publically available online for NOD-A2 mice (Jax strain 006604). Samples were run on a Light Cycler 480 (Roche). H2-D1 sequencing analysis as described above was used to identify MHCI$^{+/-}$ mice, which were then intercrossed to fix MHCI$^{-/-}$ mutations, and homozygosity was determined by flow cytometry analysis of peripheral blood B220$^+$ cells showing a lack of H2-K and H2-D.

Genotyping NOD-cMHCI/II$^{-/-}$

To sequence H2-Ab1$^{g7}$, a PCR product spanning exon 2 was amplified using the forward primer 5'-CATCCCTCCCTTGCTCTTCCTTAC-3' (SEQ ID NO:40) and reverse primer 5'-TGAGGT-CACAGCAGAGCCAG-3' (SEQ ID NO:41). The same forward primer was used for sequencing this PCR product. Mice were additionally genotyped by amplification length polymorphisms (data not shown).

Sequencing

PCR products were amplified as described for each strain above (and FIGS. 8 and 11), then purified and analyzed by sequencing on the ABI 3730 DNA analyzer (Applied Biosystems, Inc.). Mutant sequences were separated from WT using the PolyPeakParser package (37) for R.

Flow Cytometry

Single cell leukocyte suspensions were stained and run on a LSRII SORP (BD Biosciences), Attune Cytometer (ThermoFisher Scientific), or FACSAria II (BD Bioscience) with all analyses performed using FlowJo 10 (FlowJo, LLC). For splenic samples, single cell suspensions were lysed with Gey's Buffer to remove red blood cells (38). Doublet discrimination was performed (FSC-A vs FSC-H with additional SSC-A vs SSC-H gating for LSRII or SORP and FACSAria II panels), and live/dead discrimination assessed via propidium iodide staining. The following monoclonal antibodies were used: From BD Biosciences: H2-K$^d$ (SF1-1.1), B220 (RA3-6B2), CD8α (53-6.7), CD4 (GK1.5 and RM4-5), CD62L (MEL-14), CD44 (IM7.8.1), CD19 (1D3), CD45.1 (A201.7), CD90.2 (53-2.1), H-2D$^b$ (KH95), I-A$^d$ (AMS-32.1); From BioLegend: H-2L$^d$/H-2D$^b$ (28-14-8), H-2D$^b$ (KH95), HLA-A,B,C (W6,32), CD8α (53-6.7), CD4 (GK1.5), Qa-2 (695H1-9-9), CD1d (1B1), CD90.2 (30-H12), TCRγδ (GL3). HLA-A2.1-specific mAb CR11-351 (21; 39) was also used. Mouse PBS-57:CD1d tetramer (hereafter CD1d-α-GalCer tetramer) was obtained from the NIH Tetramer Facility.

Monitoring T1D Development

Ames Diastix (Bayer) were used to assess glycosuria weekly. T1D onset was defined by two readings of ≥0.25% (≥300 mg/dl in blood) on two separate days.

Insulitis Scoring

Mean insulitis scores were determined as previously described using a 0 (no visible lesions) to 4 (75-100% islet destruction) scoring method (40).

Islet Associated Leukocyte Isolation

Islet-infiltrating leukocyte populations were isolated for flow cytometry as previously described (41).

Antibody PK Study

Herceptin was detected from plasma samples using a human IgG ELISA kit according to the manufacturer's instructions (Mabtech). TNP/DNP cross-reactive IgG1 antibody 1B7.11 was detected from plasma samples by capturing with DNP-BSA (Calbiochem) coated onto ELISA plates (Costar) at 0.5 µg/ml PBS, blocked with 1% BSA in PBS+0.05% Tween 20, and detected with goat anti-mouse kappa-alkaline phosphatase (Southern Biotech).

Statistical Analysis

Prism 6 (GraphPad) was used to generate all graphs and statistics. All p-values for scatter dot plots are two-tailed Mann-Whitney analyses. All p-values for diabetes incidence studies are calculated by Mantel-Cox analysis.

---

CONSTRUCTS AND SEQUENCES

"H2-K$^d$"
H2-K1 (Havana Gene, NOD: OTTMUSG00000039404, GenBank: L36065.1)

```
ATGGCACCCTGCACGCTGCTCCTGCTGTTGGCGGCGGCCCTGGCCCCCACTCAGACCCGCGCGGGCCCACATT
CGCTGAGGTATTTCGTCACCGCCGTGTCCCGGCCCGGCCTCGGGGAGCCCCGGTTCATCGCTGTCGGCTACGT
GGACGACACGCAGTTCGTGCGCTTCGACAGCGACGCGGATAATCCGAGATTTGAGCCGCGGGCGCCGTGGAT
GGAGCAGGAGGGGCCGGAGTATTGGGAGGAGCAGACACAGAGAGCCAAGAGCGATGAGCAGTGGTTCCGAG
TGAGCCTGAGGACCGCACAGAGATACTACAACCAGAGCAAGGGCGGCTCTCACACGTTCCAGCGGATGTTCG
GCTGTGACGTGGGGTCGGACTGGCGCCTTCCTCCGCGGGTACCAGCAGTTCGCCTACGACGGCCGCGATTACAT
CGCCCTGAACGAAGACCTGAAAACGTGGACGGCGGCGGACACGGCGGCGCTGATCACCAGACGCAAGTGGG
AGCAGGCTGGTGATGCAGAGTATTACAGGGCCTACCTAGAGGGCGAGTGCGTGGAGTGGCTCCGCAGATACC
TGGAGCTCGGGAATGAGACGCTGCTGCGCACAGATTCCCCAAAGGCCCATGTGACCTATCACCCCAGATCTC
AAGTTGATGTCACCCTGAGGTGCTGGGCCCTGGGCTTCTACCCTGCTGATATCACCCTGACCTGGCAGTTGAA
TGGGGAGGACCTGACCCAGGACATGGAGCTTGTAGAGACCAGGCCTGCAGGGGATGGAACCTTCCAGAAGTG
GGCAGCTGTGGTGGTGCCTCTTGGGAAGGAGCAGAATTACACATGCCATGTGCACCATAAGGGGCTGCCTGA
GCCTCTCACCCTGAGATGGAAGCTTCCTCCATCCACTGTCTCCAACACGGTAATCATTGCTGTTCTGGTTGTCC
TTGGAGCTGCAATAGTCACTGGAGCTGTGGTGGCTTTTGTGATGAAGATGAGAAGGAACACAGGTGGAAAAG
GAGTGAACTATGCTCTGGCTCCAGGCTCCCAGACCTCTGATCTGTCTCTCCCAGATGGTAAAGTGATGGTTCA
TGACCCTCATTCTCTAGCGTGA (SEQ ID NO: 42)
```

| CONSTRUCTS AND SEQUENCES |
|---|
| H2-K1<em1Dvs><br>ATGGCACCCTGCACGCTGCTCCTGCTGTTGGCGGCCGCCCTGGCCCCCACTCAGACCCGCGCGGGCCCACATT<br>CGCTGAGGTATTTCGTCACCGCCGTGTCCCGGCCCGGCCTCGGGGAGCCCCGGTTCATCGCTGTCGGCTACGT<br>GGACGACACGCAGTTCGTGCGCTTCGACAGCGACGCGGATAATCCGAGATTTGA*CCGCGGGCGCCGTGGAT<br>GGAGCAGGAGGGGCCGGAGTATTGGGAGGAGCAGACACAGAGAGCCAAGAGCGATGAGCAGTGGTTCCGAG<br>TGAGCCTGAGGACCGCACAGAGATACTACAACCAGAGCAAGGGCGGCTCTCACACGTTCCAGCGGATGTTCG<br>GCTGTGACGTGGGGTCGGACTGGCGCCTCCTCCGCGGGTACCAGCAGTTCGCCTACGACGGCCGCGATTACAT<br>CGCCCTGAACGAAGACCTGAAAACGTGGACGGCGGCGGACACGGCGGCGCTGATCACCAGACGCAAGTGGG<br>AGCAGGCTGGTGATGCAGAGTATTACAGGGCCTACCTAGAGGGCGAGTGCGTGGAGTGGCTCCGCAGATACC<br>TGGAGCTCGGGAATGAGACGCTGCTGCGCACAGATTCCCCAAAGGCCCATGTGACCTATCACCCCAGATCTC<br>AAGTTGATGTCACCCTGAGGTGCTGGGCCCTGGGCTTCTACCCTGCTGATATCACCCTGACCTGGCAGTTGAA<br>TGGGGAGGACCTGACCCAGGACATGGAGCTTGTAGAGACCAGGCCTGCAGGGGATGGAACCTTCCAGAAGTG<br>GGCAGCTGTGGTGGTGCCTCTTGGGAAGGAGCAGAATTACACATGCCATGTGCACCATAAGGGGCTGCCTGA<br>GCCTCTCACCCTGAGATGGAAGCTTCCTCCATCCACTGTCTCCAACACGGTAATCATTGCTGTTCTGGTTGTCC<br>TTGGAGCTGCAATAGTCACTGGAGCTGTGGTGGCTTTTGTGATGAAGATGAGAAGGAACACAGGTGGAAAAG<br>GAGTGAACTATGCTCTGGCTCCAGGCTCCCAGACCTCTGATCGTCTGTCTCTCCCAGATGGTAAAGTGATGGTTCA<br>TGACCCTCATTCTCTAGCGTGA (SEQ ID NO: 43) |
| H2-K1<em4Dvs><br>ATGGCACCCTGCACGCTGCTCCTGCTGTTGGCGGCCGCCCTGGCCCCCACTCAGACCCGCGCGGGCCCACATT<br>CGCTGAGGTATTTCGTCACCGCCGTGTCCCGGCCCGGCCTCGGGGAGCCCCGGTTCATCGCTGTCGGCTACGT<br>GGACGACACGCAGTTCGTGCGCTTCGACAGCGACGCGGATAATCCGAGATTTGAGCCGCGGGCGCCGTGGAT<br>GGAGCAGGAGGGGCCGGAGTATTGGGAGGAGCAGACACAGAGAGCCAAGAGCGATGAGCAGTGGTTCCGAG<br>TGAGCCTGAGGACCGCACAGAGATACTACAACCAGAGCAAGGGCGGCTCTCACACGTTCCAGCGGATGTTCG<br>GCTGTGACGTGGGGTCGGACTGGCGCCTCCTCCGCGGGTACCAGCAGTTCGCCTACGACGGCCGCGATTACAT<br>CGCCCTGAACGAAGACCTGAAAACGTGGACGGCGGCGGACACGGCGGCGCTGATCACCAGACGCAAGTGGG<br>AGCAGGCTGGTGATGCAGAGT**TACAGGGCCTACCTAGAGGGCGAGTGCGTGGAGTGGCTCCGCAGATACC<br>TGGAGCTCGGGAATGAGACGCTGCTGCGCACAGATTCCCCAAAGGCCCATGTGACCTATCACCCCAGATCTC<br>AAGTTGATGTCACCCTGAGGTGCTGGGCCCTGGGCTTCTACCCTGCTGATATCACCCTGACCTGGCAGTTGAA<br>TGGGGAGGACCTGACCCAGGACATGGAGCTTGTAGAGACCAGGCCTGCAGGGGATGGAACCTTCCAGAAGTG<br>GGCAGCTGTGGTGGTGCCTCTTGGGAAGGAGCAGAATTACACATGCCATGTGCACCATAAGGGGCTGCCTGA<br>GCCTCTCACCCTGAGATGGAAGCTTCCTCCATCCACTGTCTCCAACACGGTAATCATTGCTGTTCTGGTTGTCC<br>TTGGAGCTGCAATAGTCACTGGAGCTGTGGTGGCTTTTGTGATGAAGATGAGAAGGAACACAGGTGGAAAAG<br>GAGTGAACTATGCTCTGGCTCCAGGCTCCCAGACCTCTGATCTGTCTCTCCCAGATGGTAAAGTGATGGTTCA<br>TGACCCTCATTCTCTAGCGTGA (SEQ ID NO: 44) |
| "H2-D$^b$"<br>H2-D1 (Havana Gene, NOD: OTTMUSG00000039527 GenBank: L36068.1)<br>ATGGGGGCGATGGCTCCGCGCACGCTGCTCCTGCTGCTGGCGGCCGCCCTGGCCCCGACTCAGACCCGCGCG<br>GGCCCACACTCGATGCGGTATTTCGAGACCGCCGTGTCCCGGCCCCGGCCATCGAGGAGCCCCGGTACATCTCT<br>GTCGGCTATGTGGACAACAAGGAGTTCGTGCGCTTCGACAGCGACGCGGAGAATCCGAGATATGAGCCGCG<br>GGCGCCGTGGATGGAGCAGGAGGGGCCGGAGTATTGGGAGCGGGAAACACAGAAAGCCAAGGGCCAAGAG<br>CAGTGGTTCCGAGTGAGCCTGAGGAACCTGCTCGGCTACTACAACCAGAGCGCGGGCGGCTCTCACACACTC<br>CAGCAGATGTCTGGCTGTGACTTGGGGTCGGACTGGCGCCTCCTCCGCGGGTACCTGCAGTTCGCCTATGAAG<br>GCCGCGATTACATCGCCCTGAACGAAGACCTGAAAACGTGGACGGCGGCGGACATGGCGGCGCAGATCACCC<br>GACGCAAGTGGGAGCAGAGTGGTGCTGCAGAGCATTACAAGGCCTACCTGGAGGGCGAGTGCGTGGAGTGG<br>CTCCACAGATACCTGAAGAACGGGAACGCGACGCTGCTGCGCACAGATTCCCCAAAGGCACATGTGACCCAT<br>CACCCCAGATCTAAAGGTGAAGTCACCCTGAGGTGCTGGGCCCTGGGTTCTACCCTGCTGACATCACCCTGA<br>CCTGGCAGTTGAATGGGGAGGAGCTGACCCAGGACATGGAGCTTGTGGAGACCAGGCCTGCAGGGGATGGA<br>ACCTTCCAGAAGTGGGCATCTGTGGTGGTGCCTCTTGGGAAGGAGCAGAATTACACATGCCGTGTGTACCATG<br>AGGGGCTGCCTGAGCCCCTCACCCTGAGATGGGAGCCTCCTCCGTCCACTGACTCTTACATGGTGATCGTTGC<br>TGTTCTGGGTGTCCTTGGAGCTATGGCCATCATTGGAGCTGTGGTGGCTTTTGTGATGAAGAGAAGGAGAAAC<br>ACAGGTGGAAAAGGAGGGGACTATGCTCTGGCTCCAGGCTCCCAGAGCTCTGAAATGTCTCTCCGAGATTGT<br>AAAGCGTGA (SEQ ID NO: 45) |
| H2-D1<em4Dvs><br>ATGGGGGCGATGGCTCCGCGCACGCTGCTCCTGCTGCTGGCGGCCGCCCTGGCCCCGACTCAGACCCGCGCG<br>GGCCCACACTCGATGCGGTATTTCGAGACCGCCGTGTCCCGGCCCGGCC**CGAGGAGCCCCGGTACATCTCT<br>GTCGGCTATGTGGACAACAAGGAGTTCGTGCGCTTCGACAGCGACGCGGAGAATCCGAGATATGAGCCGCGG<br>GCGCCGTGGATGGAGCAGGAGGGGCCGGAGTATTGGGAGCGGGAAACACAGAAAGCCAAGGGCCAAGAGC<br>AGTGGTTCCGAGTGAGCCTGAGGAACCTGCTCGGCTACTACAACCAGAGCGCGGGCGGCTCTCACACACTCC<br>AGCAGATGTCTGGCTGTGACTTGGGGTCGGACTGGCGCCTCCTCCGCGGGTACCTGCAGTTCGCCTATGAAGG<br>CCGCGATTACATCGCCCTGAACGAAGACCTGAAAACGTGGACGGCGGCGGACATGGCGGCGCAGATCACCCG<br>ACGCAAGTGGGAGCAGAGTGGTGCTGCAGAGCATTACAAGGCCTACCTGGAGGGCGAGTGCGTGGAGTGGCT<br>CCACAGATACCTGAAGAACGGGAACGCGACGCTGCTGCGCACAGATTCCCCAAAGGCACATGTGACCCATCA<br>CCCCAGATCTAAAGGTGAAGTCACCCTGAGGTGCTGGGCCCTGGGCTTCTACCCTGCTGACATCACCCTGACC<br>TGGCAGTTGAATGGGGAGGAGCTGACCCAGGACATGGAGCTTGTGGAGACCAGGCCTGCAGGGGATGGAAC<br>CTTCCAGAAGTGGGCATCTGTGGTGGTGCCTCTTGGGAAGGAGCAGAATTACACATGCCGTGTGTACCATGAG<br>GGGCTGCCTGAGCCCCTCACCCTGAGATGGGAGCCTCCTCCGTCCACTGACTCTTACATGGTGATCGTTGCTG<br>TTCTGGGTGTCCTTGGAGCTATGGCCATCATTGGAGCTGTGGTGGCTTTTGTGATGAAGAGAAGGAGAAACAC<br>AGGTGGAAAAGGAGGGGACTATGCTCTGGCTCCAGGCTCCCAGAGCTCTGAAATGTCTCTCCGAGATTGTAA<br>AGCGTGA (SEQ ID NO: 46) |
| H2 D1<em5Dvs><br>ATGGGGGCGATGGCTCCGCGCACGCTGCTCCTGCTGCTGGCGGCCGCCCTGGCCCCGACTCAGACCCGCGCG<br>GGCCCACACTCGATGCGGTATTTCGAGACCGCCGTGTCCCGGCCCGGCCATCGAGGAGCCCCGGTACATCTCT |

| CONSTRUCTS AND SEQUENCES |
|---|
| GTCGG\*\*\*\*\*\*\*\*\*\*\*ACAAGGAGTTCGTGCGCTTCGACAGCGACGCGGAGAATCCGAGATAT\*\*\*CCGCGGGCGC<br>CGTGGATGGAGCAGGAGGGGCCGGAGTATTGGGAGCGGGAAACACAGAAAGCCAAGGGCCAAGAGCAGTG<br>GTTCCGAGTGAGCCTGAGGAACCTGCTCGGCTACTACAACCAGAGCGCGGCGGCTCTCACACACTCCAGCA<br>GATGTCTGGCTGTGACTTGGGGTCGGACTGGCGCCTCCTCCGCGGGTACCTGCAGTTCGCCTATGAAGGCCGC<br>GATTACATCGCCCTGAACAAGACCTGAAAACGTGGACGGCGGCGGACATGGCGGCGCAGATCACCCGACGC<br>AAGTGGGAGCAGAGTGGTGCTGCAGAGCATTACAAGGCCTACCTGGAGGGCGAGTGCGTGGAGTGGCTCCAC<br>AGATACCTGAAGAACGGGAACGCGACGCTGCTGCGCACAGATTCCCCAAAGGCACATGTGACCCATCACCCC<br>AGATCTAAAGGTGAAGTCACCCTGAGGTGCTGGGCCCTGGGCTTCTACCCTGCTGACATCACCCTGACCTGGC<br>AGTTGAATGGGGAGGAGCTGACCCAGGACATGGAGCTTGTGGAGACCAGGCCTGCAGGGGATGGAACCTTCC<br>AGAAGTGGGCATCTGTGGTGGTGCCTCTTGGGAAGGAGCAGAATTACACATGCCGTGTGTACCATGAGGGGC<br>TGCCTGAGCCCCTCACCCTGAGATGGGAGCCTCCTCCGTCCACTGACTCTTACATGGTGATCGTTGCTGTTCTG<br>GGTGTCCTTGGAGCTATGGCCATCATTGGAGCTGTGGTGGCTTTTGTGATGAAGAGAAGGAGAAACACAGGT<br>GGAAAAGGAGGGGACTATGCTCTGGCTCCAGGCTCCCAGAGCTCTGAAATGTCTCTCCGAGATTGTAAAGCG<br>TGA (SEQ ID NO: 47) |

"H2-A$^{g7}$"
H2-Ab1$^{g7}$ (Havana Gene, NOD: OTTMUSG00000039432 GenBank: M15848.1)
ATGGCTCTGCAGATCCCCAGCCTCCTCCTCTCGGCTGCTGTGGTGGTGCTGATGGTGCTGAGCAGCCCAGGGA
CTGAGGGCGGAGACTCCGAAAGGCATTTCGTGCACCAGTTCAAGGGCGAGTGCTACTTCACCAACGGGACGC
AGCGCATACGGCTCGTGACCAGATACATCTACAACCGGGAGGAGTACCTGCGCTTCGACAGCGACGTG
GGCGAGTACCGCGCGGTGACCGAGCTGGGGCGGCACTCAGCCGAGTACTACAATAAGCAGTACCTGG
AGCGAACGCGGGCCGAGCTGGACACGGCGTGCAGACACAACTACGAGGAGACGGAGGTCCCCACCTCC
CTGCGGCGGCTTGAACAGCCCAATGTCGCCATCTCCCTGTCCAGGACAGAGGCCCTCAACCACCACAACACTC
TGGTCTGTTCGGTGACAGATTTCTACCCAGCCAAGATCAAAGTGCGCTGGTTCAGGAATGGCCAGGAGGAGA
CAGTGGGGGTCTCATCCACACAGCTTATTAGGAATGGGGACTGGACCTTCCAGGTCCTGGTCATGCTGGAGAT
GACCCCTCATCAGGGAGAGGTCTACACCTGCCATGTGGAGCATCCCAGCCTGAAGAGCCCCATCACTGTGGA
GTGGAGGGCACAGTCCGAGTCTGCCCGGAGCAAGATGTTGAGCGGCATCGGGGCTGCGTGCTTGGGGTGAT
CTTCCTCGGGCTCGGCCTTTTCATCCGTCACAGGAGTCAGAAAGGACCTCGAGGCCCTCCTCCAGCAGGGCTC
CTGCAGTGA (SEQ ID NO: 48)

H2-Aa1$^{d}$ (Havana Gene, NOD: OTTMUSG00000039433 GenBank: K01923.1)
ATGCCTGCAGCAGAGCTCTGATTCTGGGGGTCCTCGCCCTGAACACCATGCTCAGCCTCTGCGGAGGTGAAG
ACGACATTGAGGCCGACCACGTAGGCTTCTATGGTACAACTGTTTATCAGTCTCCTGGAGACATTGGCCAGTA
CACACATGAATTTGATGGTGATGAGTTGTTCTATGTGGACTTGGATAAGAAGAAACTGTCTGGAGGCTTCCT
GAGTTTGGCCAATTGATACTCTTTGAGCCCCAAGGTGGACTGCAAAACATAGCTGCAGAAAAACACAACTTG
GGAATCTTGACTAAGAGGTCAAATTTCACCCCAGCTACCAATGAGGCTCCTCAAGCGACTGTGTTCCCCAAGT
CCCCTGTGCTGCTGGGTCAGCCCAACACCCTTATCTGCTTTGTGGACAACATCTTCCCACCTGTGATCAACATC
ACATGGCTCAGAAATAGCAAGTCAGTCACAGACGGCGTTTATGAGACCAGCTTCCTCGTCAACCGTGACCATT
CCTTCCACAAGCTGTCTTATCTCACCTTCATCCCTTCTGATGATGACATTTATGACTGCAAGGTGGAGCACTGG
GGCCTGGAGGAGCCGGTTCTGAAACACTGGGAACCTGAGATTCCAGCCCCATGTCAGAGCTGACAGAAACT
GTGGTGTGTGCCCTGGGGTTGTCTGTGGGCCTTGTGGGCATCGTGGTGGGCACCATCTTCATCATTCAAGGCC
TGCGATCAGGTGGCACCTCCAGACACCCAGGGCCTTTATGA (SEQ ID NO: 49)

H2-Ab1<em1Dvs>
ATGGCTCTGCAGATCCCCAGCCTCCTCCTCTCGGCTGCTGTGGTGGTGCTGATGGTGCTGAGCAGCCCAGGGA
CTGAGGGCGGAGACTCCGAAAGGCATTTCGTGCACCAGTTCAAGGGCGAGTGCTACTTCACCAACGGGACGC
AGCGC\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*
\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*CGGAGGT
CCCCACCTCCCTGCGGCGGCTTGAACAGCCCAATGTCGCCATCTCCCTGTCCAGGACAGAGGCCCTCAACCAC
CACAACACTCTGGTCTGTTCGGTGACAGATTTCTACCCAGCCAAGATCAAAGTGCGCTGGTTCAGGAATGGCC
AGGAGGAGACAGTGGGGGTCTCATCCACACAGCTTATTAGGAATGGGGACTGGACCTTCCAGGTCCTGGTCA
TGCTGGAGATGACCCCTCATCAGGGAGAGGTCTACACCTGCCATGTGGAGCATCCCAGCCTGAAGAGCCCCA
TCACTGTGGAGTGGAGGGCACAGTCCGAGTCTGCCCGGAGCAAGATGTTGAGCGGCATCGGGGCTGCGTGC
TTGGGGTGATCTTCCTCGGGCTCGGCCTTTTCATCCGTCACAGGAGTCAGAAAGGACCTCGAGGCCCTCCTCC
AGCAGGGCTCCTGCAGTGA (SEQ ID NO: 50)

"HLA-A2.1, HLA-A2"
HLA-A\*02: 01 IMGT/HLA: HLA00005
ATGGCCGTCATGGCGCCCCGAACCCTCGTCCTGCTACTCTCGGGGGCTCTGGCCCTGACCCAGACCTGGGCGG
GCTCTCACTCCATGAGGTATTTCTTCACATCCGTGTCCCGGCCCGGCCGCGGGGAGCCCCGCTTCATCGCAGT
GGGCTACGTGGACGACACGCAGTTCGTGCGGTTCGACAGCGACGCCGCGAGCCAGAGGATGGAGCCGCGGG
CGCCGTGGATAGAGCAGGAGGGTCCGGAGTATTGGGACGGGGAGACACGGAAAGTGAAGGCCCACTCACAG
ACTCACCGAGTGGACCTGGGGACCCTGCGCGGCTACTACAACCAGAGCGAGGCCGGTTCTCACACCATCCAG
AGGATGTATGGCTGCGACGTGGGGTCGGACTGGCGCTTCCTCCGCGGGTACCACCAGTACGCCTACGACGGC
AAGGATTACATCGCCCTGAAAGAGGACCTGCGCTCTTGGACCGCGGCGGACATGGCAGCTCAGACCACCAAG
CACAAGTGGGAGGCGGCCCATGTGGCGGAGCAGTTGAGAGCCTACCTGGAGGGCACGTGCGTGGAGTGGCTC
CGCAGATACCTGGAGAACGGGAAGGAGACGCTGCAGCGCACGGACGCCCCCAAAACGCATATGACTCACCA
CGCTGTCTCTGACCATGAAGCCACCCTGAGGTGCTGGGCCCTGAGCTTCTACCCTGCGGAGATCACACTGACC
TGGCAGCGGGATGGGGAGGACCAGACCCAGGACACGGAGCTCGTGGAGACCAGGCCTGCAGGGGATGGAAC
CTTCCAGAAGTGGGCGGCTGTGGTGGTGCCTTCTGGACAGGAGCAGAGATACACCTGCCATGTGCAGCATGA
GGGTTTGCCCAAGCCCCTCACCCTGAGATGGGAGCCGTCTTCCCAGCCCACCATCCCCATCGTGGGCATCATT
GCTGGCCTGGTTCTCTTTGGAGCTGTGATCACTGGAGCTGTGGTCGCTGCTGTGATGTGGAGGAGGAAGAGCT
CAGATAGAAAAGGAGGGAGCTACTCTCAGGCTGCAAGCAGTGACAGTGCCCAGGGCTCTGATGTGTCTCTCA
CAGCTTGTAAAGTGTGA (SEQ ID NO: 51)

CONSTRUCTS AND SEQUENCES

"HLA-B39"
HLA-B*39: 06 IMGT/HLA: HLA00279
ATGCTGGTCATGGCGCCCCGAACCGTCCTCCTGCTGCTCTCGGCGGCCCTGGCCCTGACCGAGACCTGGGCCG
GCTCCCACTCCATGAGGTATTTCTACACCTCCGTGTCCCGGCCCGGCCGCGGGGAGCCCCGCTTCATCTCAGT
GGGCTACGTGGACGACACGCAGTTCGTGAGGTTCGACAGCGACGCCGCGAGTCCGAGAGAGGAGCCGCGGG
CGCCGTGGATAGAGCAGGAGGGGCCGGAATATTGGGACCGGAACACACAGATCTGCAAGACCAACACACAG
ACTGACCGAGAGAGCCTGCGGAACCTGCGCGGCTACTACAACCAGAGCGAGGCCGGGTCTCACACTTGGCAG
ACGATGTACGGCTGCGACGTGGGGCCGGACGGGCGCCTCCTCCGCGGGCATAACCAGTTCGCCTACGACGGC
AAGGATTACATCGCCCTGAACGAGGACCTGAGCTCCTGGACCGCGGCGGACACCGCGGCTCAGATCACCCAG
CGCAAGTGGGAGGCGGCCCGTGTGGCGGAGCAGCTGAGAACCTACCTGGAGGGCACGTGCGTGGAGTGGCTC
CGCAGATACCTGGAGAACGGGAAGGAGACGCTGCAGCGCGCGGACCCCCCAAAGACACATGTGACCCACCA
CCCCATCTCTGACCATGAGGCACCCTGAGGTGCTGGGCCCTGGGCTTCTACCCTGCGGAGATCACACTGACC
TGGCAGCGGGATGGCGAGGACCAAACTCAGGACACCGAGCTTGTGGAGACCAGACCAGCAGGAGACAGAAC
CTTCCAGAAGTGGGCAGCTGTGGTGGTGCCTTCTGGAGAAGAGCAGAGATACACATGCCATGTACAGCATGA
GGGGCTGCCGAAGCCCCTCACCCTGAGATGGGAGCCATCTTCCCAGTCCACCGTCCCCATCGTGGGCATTGTT
GCTGGCCTGGCTGTCCTAGCAGTTGTGGTCATCGGAGCTGTGGTCGCTGCTGTGATGTGTAGGAGGAAGAGTT
CAGGTGGAAAAGGAGGGAGCTACTCTCAGGCTGCGTCCAGCGACAGTGCCCAGGGCTCTGATGTGTCTCTCA
CAGCTTGA (SEQ ID NO: 52)

"HLA-DQ8"
HLA-DQA1*03: 01 IMGT/HLA: HLA00608
ATGATCCTAAACAAAGCTCTGATGCTGGGGGCCCTCGCCCTGACCACCGTGATGAGCCCTTGTGGAGGTGAA
GACATTGTGGCTGACCATGTTGCCTCTTACGGTGTAAACTTGTACCAGTCTTATGGTCCCTCTGGGCAGTACAG
CCATGAATTTGATGGAGACGAGGAGTTCTATGTGGACCTGGAGAGGAAGGAGACTGTCTGGCAGTTGCCTCT
GTTCCGCAGATTTAGAAGATTTGACCCGCAATTTGCACTGACAAACATCGCTGTGCTAAAACATAACTTGAAC
ATCGTGATTAAACGCTCCAACTCTACCGCTGCTACCAATGAGGTTCCTGAGGTCACAGTGTTTTCCAAGTCTCC
CGTGACACTGGGTCAGCCCAACACCCTCATCTGTCTTGTGGACAACATCTTTCCTCCTGTGGTCAACATCACCT
GGCTGAGCAATGGGCACTCAGTCACAGAAGGTGTTTCTGAGACCAGCTTCCTCTCCAAGAGTGATCATTCCTT
CTTCAAGATCAGTTACCTCACCTTCCTCCCTTCTGCTGATGAGATTTATGACTGCAAGGTGGAGCACTGGGGC
CTGGATGAGCCTCTTCTGAAACACTGGGAGCCTGAGATTCCAACACCTATGTCAGAGCTCACAGAGACTGTGG
TCTGCGCCCTGGGGTTGTCTGTGGGCCTCGTGGGCATTGTGGTGGGGACCGTCTTGATCATC
CGAGGCCTGCGTTCAGTTGGTGCTTCCAGACACCAAGGGCCCTTGTGA (SEQ ID NO: 53)

HLA-DQB1*03: 02 IMGT/HLA: HLA00627
ATGTCTTGGAAGAAGGCTTTGCGGATCCCTGGAGGCCTTCGGGTAGCAACTGTGACCTTGATGCTGGCGATGC
TGAGCACCCCGGTGGCTGAGGGCAGAGACTCTCCCGAGGATTTCGTGTACCAGTTTAAGGGCATGTGCTACTT
CACCAACGGGACGGAGCGCGTGCGTCTTGTGACCAGATACATCTATAACCGAGAGGAGTACGCACGCTTCGA
CAGCGACGTGGGGGTGTATCGGGCGGTGACGCCGCTGGGGCCGCCTGCCGCCGAGTACTGGAACAGCCAGAA
GGAAGTCCTGGAGAGGACCCGGGCGGAGTTGGACACGGTGTGCAGACACAACTACCAGTTGGAGCTCCGCAC
GACCTTGCAGCGGCGAGTGGAGCCCACAGTGACCATCTCCCCATCCAGGACAGAGGCCCTCAACCACCACAA
CCTGCTGGTCTGCTCAGTGACAGATTTCTATCCAGCCCAGATCAAAGTCCGGTGGTTTCGGAATGACCAGGAG
GAGACAACTGGCGTTGTGTCCACCCCCCTTATTAGGAACGGTGACTGGACCTTCCAGATCCTGGTGATGCTGG
AAATGACTCCCCAGCGTGGAGACGTCTACACCTGCCACGTGGAGCACCCCAGCCTCCAGAACCCCATCATCGT
GGAGTGGCGGGCTCAGTCTGAATCTGCCCAGAGCAAGATGCTGAGTGGCATTGGAGGCTTCGTGCTGGGGCT
GATCTTCCTCGGGCTGGGCCTTATTATCCATCACAGGAGTCAGAAAGGGCTCCTGCACTGA (SEQ ID NO: 54)

"HLA-DR3"
HLA-DRB1*03: 01 IMGT/HLA: HLA00671
ATGGTGTGTCTGAGGCTCCCTGGAGGCTCCTGCATGGCAGTTCTGACAGTGACACTGATGGTGCTGAGCTCCC
CACTGGCTTTGGCTGGGGACACCAGACCACGTTTCTTGGAGTACTCTACGTCTGAGTGTCATTTCTTCAATGGG
ACGGAGCGGGTGCGGTACCTGGACAGATACTTCCATAACCAGGAGGAGAACGTGCGCTTCGACAGCGACGTG
GGGGAGTTCCGGGCGGTGACGGAGCTGGGGCGGCCTGATGCCGAGTACTGGAACAGCCAGAAGGACCTCCTG
GAGCAGAAGCGGGCCGGTGGACAACTACTGCAGACACAACTACGGGGTTGTGGAGAGCTTCACAGTGCA
GCGGCGAGTCCATCCTAAGGTGACTGTGTATCCTTCAAAGACCCAGCCCCTGCAGCACCATAACCTCCTGGTC
TGTTCTGTGAGTGGTTTCTATCCAGGCAGCATTGAAGTCAGGTGGTTCCGGAATGGCCAGGAAGAGAAGACT
GGGGTGGTGTCCACAGGCCTGATCCACAATGGAGACTGGACCTTCCAGACCCTGGTGATGCTGGAAACAGTT
CCTCGGAGTGGAGAGGTTTACACCTGCCAAGTGGAGCACCCAAGCGTGACAAGCCCTCTCACAGTGGAATGG
AGAGCACGGTCTGAATCTGCACAGAGCAAGATGCTGAGTGGAGTCGGGGCTTTGTGCTGGGCCTGCTCTTCC
TTGGGGCCGGGCTGTTCATCTACTTCAGGAATCAGAAAGGACACTCTGGACTTCAGCCAAGAGGATTCCTGAG
CTGA (SEQ ID NO: 55)

"HLA-DR4"
HLA-DRB1*04: 01 IMGT/HLA: HLA00685
ATGGTGTGTCTGAAGTTCCCTGGAGGCTCCTGCATGGCAGCTCTGACAGTGACACTGATGGTGCTGAGCTCCC
CACTGGCTTTGGCTGGGGACACCCGACCACGTTTCTTGGAGCAGGTTAAACATGAGTGTCATTTCTTCAACGG
GACGGAGCGGGTGCGGTTCCTGGACAGATACTTCTATCACCAAGAGGAGTACGTGCGCTTCGACAGCGACGT
GGGGGAGTACCGGGCGGTGACGGAGCTGGGGCGGCCTGATGCCGAGTACTGGAACAGCCAGAAGGACCTCC
TGGAGCAGAAGCGGGCCGCGGTGGACACCTACTGCAGACACAACTACGGGGTTGGTGAGAGCTTCACAGTGC
AGCGGCGAGTCTATCCTGAGGTGACTGTGTATCCTGCAAAGACCCAGCCCCTGCAGCACCACAACCTCCTGGT
CTGCTCTGTGAATGGTTTCTATCCAGGCAGCATTGAAGTCAGGTGGTTCCGGAACGGCCAGGAAGAGAAGAC
TGGGGTGGTGTCCACAGGCCTGATCCAGAATGGAGACTGGACCTTCCAGACCCTGGTGATGCTGGAAACAGT
TCCTCGGAGTGGAGAGGTTTACACCTGCCAAGTGGAGCACCCAAGCCTGACGAGCCCTCTCACAGTGGAATG
GAGAGCACGGTCTGAATCTGCACAGAGCAAGATGCTGAGTGGAGTCGGGGGCTTCGTGCTGGGCCTGCTCTT
CCTTGGGGCCGGGCTGTTCATCTACTTCAGGAATCAGAAAGGACACTCTGGACTTCAGCCAACAGGATTCCTG
AGCTGA (SEQ ID NO: 56)

CONSTRUCTS AND SEQUENCES

"HLA-DQ2"
HLA-DQA1*05: 01 IMGT/HLA: HLA00613
ATGATCCTAAACAAAGCTCTGATGCTGGGGGCCCTTGCCCTGACCACCGTGATGAGCCCCTGTGGAGGTGAA
GACATTGTGGCTGACCACGTCGCCTCTTATGGTGTAAACTTGTACCAGTCTTACGGTCCCTCTGGCCAGTACAC
CCATGAATTTGATGGAGATGAGCAGTTCTACGTGGACCTGGGGAGGAAGGAGACTGTCTGGTGTTTGCCTGTT
CTCAGACAATTTAGATTTGACCCGCAATTTGCACTGACAAACATCGCTGTCCTAAAACATAACTTGAACAGTC
TGATTAAACGCTCCAACTCTACCGCTGCTACCAATGAGGTTCCTGAGGTCACAGTGTTTTCCAAGTCTCCCGTG
ACACTGGGTCAGCCCAACATCCTCATCTGTCTTGTGGACAACATCTTTCCTCCTGTGGTCAACATCACATGGCT
GAGCAATGGGCACTCAGTCACAGAAGGTGTTTCTGAGACCAGCTTCCTCTCCAAGAGTGATCATTCCTTCTTC
AAGATCAGTTACCTCACCCTCCTCCCTTCTGCTGAGGAGAGTTATGACTGCAAGGTGGAGCACTGGGGCCTGG
ACAAGCCTCTTCTGAAACACTGGGAGCCTGAGATTCCAGCCCCTATGTCAGAGCTCACAGAGACTGTGGTCTG
CGCCCTGGGATTGTCTGTGGGCCTCGTGGGCATTGTGGTGGGCACTGTCTTCATCATCCGAGGCCTGCGTTCA
GTTGGTGCTTCCAGACACCAAGGGCCCTTGTGA (SEQ ID NO: 57)

HLA-DQB1*02: 01 IMGT/HLA: HLA00622
ATGTCTTGGAAAAAGGCTTTGCGGATCCCCGGAGGCCTTCGGGCAGCAACTGTGACCTTGATGCTGTCGATGC
TGAGCACCCCAGTGGCTGAGGGCAGAGACTCTCCCGAGGATTTCGTGTACCAGTTTAAGGGCATGTGCTACTT
CACCAACGGGACAGAGCGCGTGCGTCTTGTGAGCAGAAGCATCTATAACCGAGAAGAGATCGTGCGCTTCGA
CAGCGACGTGGGGGAGTTCCGGGCGGTGACGCTGCTGGGGCTGCCTGCCGCCGAGTACTGGAACAGCCAGAA
GGACATCCTGGAGAGGAAACGGGCGGCGGTGGACAGGGTGTGCAGACACAACTACCAGTTGGAGCTCCGCA
CGACCTTGCAGCGGCGAGTGGAGCCCACAGTGACCATCTCCCCATCCAGGACAGAGGCCCTCAACCACCACA
ACCTGCTGGTCTGCTCGGTGACAGATTTCTATCCAGCCCAGATCAAAGTCCGGTGGTTTCGGAATGACCAGGA
GGGAGACAGCTGGCGTTGTGTCCACCCCCCTTATTAGGAATGGTGACTGGACCTTCCAGATCCTGGTGATGCTG
GAAATGACTCCCCAGCGTGGAGACGTCTACACCTGCCACGTGGAGCACCCCAGCCTCCAGAGCCCCATCACC
GTGGAGTGGCGGGCTCAATCTGAATCTGCCCAGAGCAAGATGCTGAGTGGCATTGGAGGCTTCGTGCTGGGG
CTGATCTTCCTCGGGCTGGGCCTTATCATCCATCACAGGAGTCAGAAAGGGCTCCTGCACTGA (SEQ ID NO: 58)

REFERENCES

1. Chaparro R J, Dilorenzo T P: An update on the use of NOD mice to study autoimmune (Type 1) diabetes. Expert review of clinical immunology 2010; 6:939-955
2. Atkinson M A, Leiter E H: The NOD mouse model of type 1 diabetes: as good as it gets? Nat Med 1999; 5:601-604
3. Serreze D V, Niens M, Kulik J, DiLorenzo T P: Bridging Mice to Men: Using HLA Transgenic Mice to Enhance the Future Prediction and Prevention of Autoimmune Type 1 Diabetes in Humans. Methods in molecular biology 2016; 1438:137-151
4. Serreze D V, Marron M P, Dilorenzo T P: "Humanized" HLA transgenic NOD mice to identify pancreatic beta cell autoantigens of potential clinical relevance to type 1 diabetes. Annals of the New York Academy of Sciences 2007; 1103:103-111
5. Noble J A, Erlich H A: Genetics of type 1 diabetes. Cold Spring Harbor perspectives in medicine 2012; 2:a007732
6. Pociot F, Akolkar B, Concannon P, Erlich H A, Julier C, Morahan G, Nierras C R, Todd J A, Rich S S, Nerup J: Genetics of type 1 diabetes: what's next? Diabetes 2010; 59:1561-1571
7. Todd J A, Bell J I, McDevitt H O: HLA-DQ beta gene contributes to susceptibility and resistance to insulin-dependent diabetes mellitus. Nature 1987; 329:599-604
8. Tait B D, Drummond B P, Varney M D, Harrison L C: HLA-DRB1*0401 is associated with susceptibility to insulin-dependent diabetes mellitus independently of the DQB1 locus. European journal of immunogenetics: official journal of the British Society for Histocompatibility and Immunogenetics 1995; 22:289-297
9. Erlich H, Valdes A M, Noble J, Carlson J A, Varney M, Concannon P, Mychaleckyj J C, Todd J A, Bonella P, Fear A L, Lavant E, Louey A, Moonsamy P, Type 1 Diabetes Genetics C: HLA DR-DQ haplotypes and genotypes and type 1 diabetes risk: analysis of the type 1 diabetes genetics consortium families. Diabetes 2008; 57:1084-1092
10. Miyazaki T, Uno M, Uehira M, Kikutani H, Kishimoto T, Kimoto M, Nishimoto H, Miyazaki J, Yamamura K: Direct evidence for the contribution of the unique I-ANOD to the development of insulitis in non-obese diabetic mice. Nature 1990; 345:722-724
11. Serreze D V, Leiter E H, Christianson G J, Greiner D, Roopenian D C: Major histocompatibility complex class I-deficient NOD-B2mnull mice are diabetes and insulitis resistant. Diabetes 1994; 43:505-509
12. Noble J A, Valdes A M, Varney M D, Carlson J A, Moonsamy P, Fear A L, Lane J A, Lavant E, Rappner R, Louey A, Concannon P, Mychaleckyj J C, Erlich H A: HLA class I and genetic susceptibility to type 1 diabetes: results from the Type 1 Diabetes Genetics Consortium. Diabetes 2010; 59:2972-2979
13. Nejentsev S, Howson J M, Walker N M, Szeszko J, Field S F, Stevens H E, Reynolds P, Hardy M, King E, Masters J, Hulme J, Maier L M, Smyth D, Bailey R, Cooper J D, Ribas G, Campbell R D, Clayton D G, Todd J A, Wellcome Trust Case Control C: Localization of type 1 diabetes susceptibility to the MHC class I genes HLA-B and HLA-A. Nature 2007; 450:887-892
14. Fennessy M, Metcalfe K, Hitman G A, Niven M, Biro P A, Tuomilehto J, Tuomilehto-Wolf E: A gene in the HLA class I region contributes to susceptibility to IDDM in the Finnish population. Childhood Diabetes in Finland (DiMe) Study Group. Diabetologia 1994; 37:937-944
15. Howson J M, Walker N M, Clayton D, Todd J A, Type 1 Diabetes Genetics C: Confirmation of HLA class II independent type 1 diabetes associations in the major histocompatibility complex including HLA-B and HLA-A. Diabetes, obesity & metabolism 2009; 11 Suppl 1:31-45
16. Valdes A M, Erlich H A, Noble J A: Human leukocyte antigen class I B and C loci contribute to Type 1 Diabetes (T1D) susceptibility and age at T1D onset. Human immunology 2005; 66:301-313
17. Roark C L, Anderson K M, Simon L J, Schuyler R P, Aubrey M T, Freed B M: Multiple HLA epitopes contribute to type 1 diabetes susceptibility. Diabetes 2014; 63:323-331

18. Mikk M L, Heikkinen T, El-Amir M I, Kiviniemi M, Laine A P, Harkonen T, Veijola R, Toppari J, Knip M, Ilonen J, Finnish Paediatric Diabetes R: The association of the HLA-A*24:02, B*39:01 and B*39:06 alleles with type 1 diabetes is restricted to specific HLA-DR/DQ haplotypes in Finns. Hla 2017; 89:215-224
19. Mikk M L, Kiviniemi M, Laine A P, Harkonen T, Veijola R, Simell O, Knip M, Ilonen J, Finnish Paediatric Diabetes R: The HLA-B*39 allele increases type 1 diabetes risk conferred by HLA-DRB1*04:04-DQB1*03:02 and HLA-DRB1*08-DQB1*04 class II haplotypes. Human immunology 2014; 75:65-70
20. Pascolo S, Bervas N, Ure J M, Smith A G, Lemonnier F A, Perarnau B: HLA-A2.1-restricted education and cytolytic activity of CD8(+) T lymphocytes from beta2 microglobulin (beta2m) HLA-A2.1 monochain transgenic H-2db beta2m double knockout mice. The Journal of experimental medicine 1997; 185:2043-2051
21. Takaki T, Marron M P, Mathews C E, Guttmann S T, Bottino R, Trucco M, DiLorenzo T P, Serreze D V: HLA-A*0201-restricted T cells from humanized NOD mice recognize autoantigens of potential clinical relevance to type 1 diabetes. J Immunol 2006; 176:3257-3265
22. Jarchum I, Baker J C, Yamada T, Takaki T, Marron M P, Serreze D V, DiLorenzo T P: In vivo cytotoxicity of insulin-specific CD8+ T-cells in HLA-A*0201 transgenic NOD mice. Diabetes 2007; 56:2551-2560
23. Jarchum I, DiLorenzo T P: Ins2 deficiency augments spontaneous HLA-A*0201-restricted T cell responses to insulin. J Immunol 2010; 184:658-665
24. Jarchum I, Nichol L, Trucco M, Santamaria P, DiLorenzo T P: Identification of novel IGRP epitopes targeted in type 1 diabetes patients. Clinical immunology 2008; 127:359-365
25. Mallone R, Martinuzzi E, Blancou P, Novelli G, Afonso G, Dolz M, Bruno G, Chaillous L, Chatenoud L, Bach J M, van Endert P: CD8+ T-cell responses identify beta-cell autoimmunity in human type 1 diabetes. Diabetes 2007; 56:613-621
26. Unger W W, Pinkse G G, Mulder-van der Kracht S, van der Slik A R, Kester M G, Ossendorp F, Drijfhout J W, Serreze D V, Roep B O: Human clonal CD8 autoreactivity to an IGRP islet epitope shared between mice and men. Annals of the New York Academy of Sciences 2007; 1103:192-195
27. Li Y, Zhou L, Li Y, Zhang J, Guo B, Meng G, Chen X, Zheng Q, Zhang L, Zhang M, Wang L: Identification of autoreactive CD8+ T cell responses targeting chromogranin A in humanized NOD mice and type 1 diabetes patients. Clinical immunology 2015; 159:63-71
28. Ouyang Q, Standifer N E, Qin H, Gottlieb P, Verchere C B, Nepom G T, Tan R, Panagiotopoulos C: Recognition of HLA class I-restricted beta-cell epitopes in type 1 diabetes. Diabetes 2006; 55:3068-3074
29. Pinkse G G, Tysma O H, Bergen C A, Kester M G, Ossendorp F, van Veelen P A, Keymeulen B, Pipeleers D, Drijfhout J W, Roep B O: Autoreactive CD8 T cells associated with beta cell destruction in type 1 diabetes. Proceedings of the National Academy of Sciences of the United States of America 2005; 102:18425-18430
30. Niens M, Grier A E, Marron M, Kay T W, Greiner D L, Serreze D V: Prevention of "Humanized" diabetogenic CD8 T-cell responses in HLA-transgenic NOD mice by a multipeptide coupled-cell approach. Diabetes 2011; 60:1229-1236
31. Schloss J, Ali R, Racine J J, Chapman H D, Serreze D V, DiLorenzo T P. HLA-B*39:06 Efficiently Mediates Type 1 Diabetes in a Mouse Model Incorporating Reduced Thymic Insulin Expression. J Immunol. 2018 May 15; 200(10):3353-3363
33. Baker K, Rath T, Pyzik M, Blumberg R S: The Role of FcRn in Antigen Presentation. Frontiers in immunology 2014; 5:408
34. Chaudhury C, Mehnaz S, Robinson J M, Hayton W L, Pearl D K, Roopenian D C, Anderson C L: The major histocompatibility complex-related Fc receptor for IgG (FcRn) binds albumin and prolongs its lifespan. The Journal of experimental medicine 2003; 197:315-322
35. Roopenian D C, Christianson G J, Sproule T J, Brown A C, Akilesh S, Jung N, Petkova S, Avanessian L, Choi E Y, Shaffer D J, Eden P A, Anderson C L: The MHC class I-like IgG receptor controls perinatal IgG transport, IgG homeostasis, and fate of IgG-Fc-coupled drugs. J Immunol 2003; 170:3528-3533
36. Larsen M T, Kuhlmann M, Hvam M L, Howard K A: Albumin-based drug delivery: harnessing nature to cure disease. Molecular and cellular therapies 2016; 4:3
37. Hill J T, Demarest B L, Bisgrove B W, Su Y C, Smith M, Yost H J: Poly peak parser: Method and software for identification of unknown indels using sanger sequencing of polymerase chain reaction products. Developmental dynamics: an official publication of the American Association of Anatomists 2014; 243:1632-1636
38. Julius M H, Herzenberg L A: Isolation of antigen-binding cells from unprimed mice: demonstration of antibody-forming cell precursor activity and correlation between precursor and secreted antibody avidities. The Journal of experimental medicine 1974; 140:904-920
39. Russo C, Ng A K, Pellegrino M A, Ferrone S: The monoclonal antibody CR11-351 discriminates HLA-A2 variants identified by T cells. Immunogenetics 1983; 18:23-35
40. Johnson E A, Silveira P, Chapman H D, Leiter E H, Serreze D V: Inhibition of autoimmune diabetes in nonobese diabetic mice by transgenic restoration of H2-E MHC class II expression: additive, but unequal, involvement of multiple APC subtypes. J Immunol 2001; 167: 2404-2410
41. Serreze D V, Chapman H D, Niens M, Dunn R, Kehry M R, Driver J P, Haller M, Wasserfall C, Atkinson M A: Loss of intra-islet CD20 expression may complicate efficacy of B-cell-directed type 1 diabetes therapies. Diabetes 2011; 60:2914-2921
42. Sharif S, Arreaza G A, Zucker P, Mi Q S, Sondhi J, Naidenko O V, Kronenberg M, Koezuka Y, Delovitch T L, Gombert J M, Leite-De-Moraes M, Gouarin C, Zhu R, Hameg A, Nakayama T, Taniguchi M, Lepault F, Lehuen A, Bach J F, Herbelin A: Activation of natural killer T cells by alpha-galactosylceramide treatment prevents the onset and recurrence of autoimmune Type 1 diabetes. Nat Med 2001; 7:1057-1062
43. Wang B, Geng Y B, Wang C R: CD1-restricted NK T cells protect nonobese diabetic mice from developing diabetes. The Journal of experimental medicine 2001; 194:313-320
44. Chen Y G, Choisy-Rossi C M, Holl T M, Chapman H D, Besra G S, Porcelli S A, Shaffer D J, Roopenian D, Wilson S B, Serreze D V: Activated NKT cells inhibit autoimmune diabetes through tolerogenic recruitment of dendritic cells to pancreatic lymph nodes. J Immunol 2005; 174:1196-1204

45. Marron M P, Graser R T, Chapman H D, Serreze D V: Functional evidence for the mediation of diabetogenic T cell responses by HLA-A2.1 MHC class I molecules through transgenic expression in NOD mice. Proceedings of the National Academy of Sciences of the United States of America 2002; 99:13753-13758
46. Vance R E, Kraft J R, Altman J D, Jensen P E, Raulet D H: Mouse CD94/NKG2A is a natural killer cell receptor for the nonclassical major histocompatibility complex (MHC) class I molecule Qa-1(b). The Journal of experimental medicine 1998; 188:1841-1848
47. Shi F D, Flodstrom M, Balasa B, Kim S H, Van Gunst K, Strominger J L, Wilson S B, Sarvetnick N: Germ line deletion of the CD1 locus exacerbates diabetes in the NOD mouse. Proceedings of the National Academy of Sciences of the United States of America 2001; 98:6777-6782
48. Simoni Y, Gautron A S, Beaudoin L, Bui L C, Michel M L, Coumoul X, Eberl G, Leite-de-Moraes M, Lehuen A: NOD mice contain an elevated frequency of iNKT17 cells that exacerbate diabetes. European journal of immunology 2011; 41:3574-3585
49. Godfrey D I, Uldrich A P, McCluskey J, Rossjohn J, Moody D B: The burgeoning family of unconventional T cells. Nature immunology 2015; 16:1114-1123
50. Haeryfar S M, Al-Alwan M M, Mader J S, Rowden G, West K A, Hoskin D W: Thy-1 signaling in the context of costimulation provided by dendritic cells provides signal 1 for T cell proliferation and cytotoxic effector molecule expression, but fails to trigger delivery of the lethal hit. J Immunol 2003; 171:69-77

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The terms "about" and "substantially" preceding a numerical value mean±10% of the recited numerical value.

Where a range of values is provided, each value between the upper and lower ends of the range are specifically contemplated and described herein.

What is claimed is:

1. A method comprising:

(a) providing a non-obese diabetic (NOD) mouse having a NOD/ShiLtJ or NOD/ShiLtDvs genetic background, wherein (i) the mouse is homozygous for a knockout mutation in a H2-K1$^d$ allele, the mouse is homozygous for a knockout mutation in a H2-D1$^b$ allele, (iii) murine H2-K and H2-D MHC class I molecules are not expressed in the mouse, and (iv) the mouse is resistant to type 1 diabetes and insulitis out to thirty weeks of age;

(b) administering a test agent to the mouse; and (c) assaying the mouse for a symptom of diabetes.

2. The method of claim 1, wherein the mouse is homozygous for a knockout mutation in a H2-Ab1$^{g7}$ allele, and murine H2-A MHC class II molecules are not expressed in the mouse.

3. The method of claim 1, wherein the mouse further comprises a human HLA-A transgene, and human HLA-A MHC class I molecules are expressed in the mouse; and/or the mouse further comprises a human HLA-B transgene, and human HLA-B MHC class I molecules are expressed in the mouse.

4. The method of claim 3, wherein the human HLA-A transgene is a human HLA-A2 transgene.

5. The method of claim 3, wherein the human HLA-B transgene is a human HLA-B39 transgene.

6. The method of claim 1, wherein the symptom of diabetes is glycosuria.

7. The method of claim 1, wherein the symptom of diabetes is insulitis.

8. The method of claim 1, wherein the test agent is an antibody.

9. The method of claim 1, wherein the test agent is an antigen.

* * * * *

SEQUENCE LISTING

```
<160> NUMBER OF SEQ ID NOS: 67

<210> SEQ ID NO 1
<211> LENGTH: 35
<212> TYPE: DNA
<213> ORGANISM: Artificial Sequence
<220> FEATURE:
<223> OTHER INFORMATION: Synthetic polynucleotide

<400> SEQUENCE: 1
cccggcccgg cctcgaggag ccccggtaca tctct                        35

<210> SEQ ID NO 2
<211> LENGTH: 35
<212> TYPE: DNA
<213> ORGANISM: Artificial Sequence
<220> FEATURE:
<223> OTHER INFORMATION: Synthetic polynucleotide

<400> SEQUENCE: 2
agagatgtac cggggctcct cgaggccggg ccggg                        35

<210> SEQ ID NO 3
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 3
gtaccggggc tcctcgaggc                                         20

<210> SEQ ID NO 4
<211> LENGTH: 30
<212> TYPE: DNA
```

```
<213> ORGANISM: Artificial Sequence
<220> FEATURE:
<223> OTHER INFORMATION: Synthetic polynucleotide

<400> SEQUENCE: 4
aggctggtga tgcagagtat tacagggcct                              30

<210> SEQ ID NO 5
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 5
aggccctgta atactctgca tcaccagcct                              30

<210> SEQ ID NO 6
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 6
tggtgatgca gagtattaca                                         20

<210> SEQ ID NO 7
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 7
ggagccccgg tacatctctg tcggctatgt ggacaacata tgagccg           47

<210> SEQ ID NO 8
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 8
cggctcatat gttgtccaca tacccgacag agatgtaccg gggctcc           47

<210> SEQ ID NO 9
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 9
gtacatctct gtcggctatg                                         20

<210> SEQ ID NO 10
<211> LENGTH: 35
<212> TYPE: DNA
<213> ORGANISM: Artificial Sequence
<220> FEATURE:
<223> OTHER INFORMATION: Synthetic polynucleotide

<400> SEQUENCE: 10
acgcggataa tccgagattt gagccgcggg cgccg                        35
```

<210> SEQ ID NO 11
<211> LENGTH: 35
<212> TYPE: DNA
<213> ORGANISM: Artificial Sequence
<220> FEATURE:
<223> OTHER INFORMATION: Synthetic polynucleotide

<400> SEQUENCE: 11
cggcgcccgc ggctcaaatc tcggattatc cgcgt       35

<210> SEQ ID NO 12
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 12
ataatccgag atttgagccg       20

<210> SEQ ID NO 13
<211> LENGTH: 40
<212> TYPE: DNA
<213> ORGANISM: Artificial Sequence
<220> FEATURE:
<223> OTHER INFORMATION: Synthetic polynucleotide

<400> SEQUENCE: 13
acttcaccaa cgggacgcag cgcatacggc tcgtgaccag       40

<210> SEQ ID NO 14
<211> LENGTH: 40
<212> TYPE: DNA
<213> ORGANISM: Artificial Sequence
<220> FEATURE:
<223> OTHER INFORMATION: Synthetic polynucleotide

<400> SEQUENCE: 14
tgaagtggtt gccctgcgtc gcgtatgccg agcactggtc       40

<210> SEQ ID NO 15
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 15
ccaacgggac gcagcgcata       20

<210> SEQ ID NO 16
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 16
cgacgtgggc gagtaccgcg       20

<210> SEQ ID NO 17
<211> LENGTH: 20
<212> TYPE: DNA
<213> ORGANISM: Artificial Sequence
<220> FEATURE:

<223> OTHER INFORMATION: Synthetic polynucleotide

<400> SEQUENCE: 17
cgaagcgcag gtactcctcc                                                    20

<210> SEQ ID NO 18
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 18
acacaactac gaggagacgg                                                    20

<210> SEQ ID NO 19
<211> LENGTH: 266
<212> TYPE: DNA
<213> ORGANISM: Artificial Sequence
<220> FEATURE:
<223> OTHER INFORMATION: Synthetic polynucleotide

<400> SEQUENCE: 19
ggcatttcgt gcaccagttc aagggcgagt gctacttcac caacggacgc agcgcatacg        60
gctcgtgacc agatacatct acaaccggga ggagtacctg cgcttcgaca gcgacgtggg       120
cgagtaccgc gcggtgaccg agctggggcg gcactcagcc gagtactaca ataagcagta       180
cctggagcga acgcgggccg agctggacac ggcgtgcaga cacaactacg aggagacgga       240
ggtccccacc tccctgcggc ggcttg                                            266

<210> SEQ ID NO 20
<211> LENGTH: 86
<212> TYPE: DNA
<213> ORGANISM: Artificial Sequence
<220> FEATURE:
<223> OTHER INFORMATION: Synthetic polynucleotide

<400> SEQUENCE: 20
ggcatttcgt gcaccagttc aagggcgagt gctacttcac caacgggacg cagcgccgga       60
ggtccccacc tccctgcggc ggcttg                                             86

<210> SEQ ID NO 21
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 21
gtattacagg gcctacctag                                                    20

<210> SEQ ID NO 22
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 22
agatgtaccg gggctcctcg                                                    20

<210> SEQ ID NO 23
<211> LENGTH: 24

```
<212> TYPE: DNA
<213> ORGANISM: Artificial Sequence
<220> FEATURE:
<223> OTHER INFORMATION: Synthetic polynucleotide

<400> SEQUENCE: 23
tcagacaccc gggatcccag atgg                                      24

<210> SEQ ID NO 24
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 24
cgcgctctgg ttgtagtagc cgag                                      24

<210> SEQ ID NO 25
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 25
ggcgagattc caggagccaa                                           20

<210> SEQ ID NO 26
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 26
ttccgggtcc gttctgttcc                                           20

<210> SEQ ID NO 27
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 27
caggttcctc aggctcactc                                           20

<210> SEQ ID NO 28
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 28
tttcccgctc ccaatactc                                            19

<210> SEQ ID NO 29
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 29
```

```
attcgctgag gtatttcgtc                                            20

<210> SEQ ID NO 30
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 30
ttctctcctt ccctcctgag ac                                         22

<210> SEQ ID NO 31
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 31
cccggaaccg gtttcccttt                                            20

<210> SEQ ID NO 32
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 32
agtcgctaat cgccgaccag t                                          21

<210> SEQ ID NO 33
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 33
cgggaagtgg aggggtcgtg                                            20

<210> SEQ ID NO 34
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 34
ggagacacgg aaagtgaagg                                            20

<210> SEQ ID NO 35
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 35
ggcctcgctc tggttgtag                                             19

<210> SEQ ID NO 36
<211> LENGTH: 20
<212> TYPE: DNA
<213> ORGANISM: Artificial Sequence
```

<220> FEATURE:
<223> OTHER INFORMATION: Synthetic polynucleotide

<400> SEQUENCE: 36
ccgagtggac ctggggaccc                                                  20

<210> SEQ ID NO 37
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 37
cacgtgggct ccagcatt                                                    18

<210> SEQ ID NO 38
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 38
tcaccagtca tttctgcctt tg                                               22

<210> SEQ ID NO 39
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 39
ccaatggtcg ggcactgctc aa                                               22

<210> SEQ ID NO 40
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 40
catccctccc ttgctcttcc ttac                                             24

<210> SEQ ID NO 41
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 41
tgaggtcaca gcagagccag                                                  20

<210> SEQ ID NO 42
<211> LENGTH: 1107
<212> TYPE: DNA
<213> ORGANISM: Mus musculus

<400> SEQUENCE: 42
atggcaccct gcacgctgct cctgctgttg gcggccgccc tggccccac tcagacccgc       60 gcgggcccac attcgctgag gtatttcgtc accgccgtgt cccggccgg cctcggggag      120

|  |  |  |  |  |
|---|---|---|---|---|
| ccccggttca | tcgctgtcgg | ctacgtggac | gacacgcagt tcgtgcgctt | cgacagcgac | 180 |
| gcggataatc | cgagatttga | gccgcgggcg | ccgtggatgg agcaggaggg | gccggagtat | 240 |
| tgggaggagc | agacacagag | agccaagagc | gatgagcagt ggttccgagt | gagcctgagg | 300 |
| accgcacaga | gatactacaa | ccagagcaag | ggcggctctc acacgttcca | gcggatgttc | 360 |
| ggctgtgacg | tggggtcgga | ctggcgcctc | ctccgcgggt accagcagtt | cgcctacgac | 420 |
| ggccgcgatt | acatcgccct | gaacgaagac | ctgaaaacgt ggacggcggc | ggacacggcg | 480 |
| gcgctgatca | ccagacgcaa | gtgggagcag | gctggtgatg cagagtatta | cagggcctac | 540 |
| ctagagggcg | agtgcgtgga | gtggctccgc | agatacctgg agctcgggaa | tgagacgctg | 600 |
| ctgcgcacag | attccccaaa | ggcccatgtg | acctatcacc ccagatctca | agttgatgtc | 660 |
| accctgaggt | gctgggccct | gggcttctac | cctgctgata tcaccctgac | ctggcagttg | 720 |
| aatggggagg | acctgaccca | ggacatggag | cttgtagaga ccaggcctgc | aggggatgga | 780 |
| accttccaga | gtgggcagc | tgtggtggtg | cctcttggga aggagcagaa | ttacacatgc | 840 |
| catgtgcacc | ataagggct | gcctgagcct | ctcaccctga gatggaagct | tcctccatcc | 900 |
| actgtctcca | cacggtaat | cattgctgtt | ctggttgtcc ttggagctgc | aatagtcact | 960 |
| ggagctgtgg | tggcttttgt | gatgaagatg | agaaggaaca caggtggaaa | aggagtgaac | 1020 |
| tatgctctgg | ctccaggctc | ccagacctct | gatctgtctc tcccagatgg | taaagtgatg | 1080 |
| gttcatgacc | ctcattctct | agcgtga |  |  | 1107 |

<210> SEQ ID NO 43
<211> LENGTH: 1106
<212> TYPE: DNA
<213> ORGANISM: Artificial Sequence
<220> FEATURE:
<223> OTHER INFORMATION: Synthetic polynucleotide

<400> SEQUENCE: 43

|  |  |  |  |  |
|---|---|---|---|---|
| atggcaccct | gcacgctgct | cctgctgttg | gcggccgccc tggcccccac | tcagacccgc | 60 |
| gcgggcccac | attcgctgag | gtatttcgtc | accgcgtgt cccggcccgg | cctcggggag | 120 |
| ccccggttca | tcgctgtcgg | ctacgtggac | gacacgcagt tcgtgcgctt | cgacagcgac | 180 |
| gcggataatc | cgagatttga | ccgcgggcgc | cgtggatgga gcaggagggg | ccggagtatt | 240 |
| gggaggagca | gacacagaga | gccaagagcg | atgagcagtg gttccgagtg | agcctgagga | 300 |
| ccgcacagag | atactacaac | cagagcaagg | gcggctctca cacgttccag | cggatgttcg | 360 |
| gctgtgacgt | ggggtcggac | tggcgcctcc | tccgcgggta ccagcagttc | gcctacgacg | 420 |
| gccgcgatta | catcgccctg | aacgaagacc | tgaaaacgtg gacggcggcg | gacacggcgg | 480 |
| cgctgatcac | cagacgcaag | tgggagcagg | ctggtgatgc agagtattac | agggcctacc | 540 |
| tagagggcga | gtgcgtggag | tggctccgca | gatacctgga gctcgggaat | gagacgctgc | 600 |
| tgcgcacaga | ttccccaaag | gcccatgtga | cctatcaccc cagatctcaa | gttgatgtca | 660 |
| ccctgaggtg | ctgggccctg | ggcttctacc | ctgctgatat caccctgacc | tggcagttga | 720 |
| atggggagga | cctgacccag | gacatggagc | ttgtagagac caggcctgca | ggggatggaa | 780 |
| ccttccagaa | gtgggcagct | gtggtggtgc | ctcttgggaa ggagcagaat | tacacatgcc | 840 |
| atgtgcacca | taagggctg | cctgagcctc | tcaccctgag atggaagctt | cctccatcca | 900 |
| ctgtctccaa | cacggtaatc | attgctgttc | tggttgtcct tggagctgca | atagtcactg | 960 |
| gagctgtggt | ggcttttgtg | atgaagatga | agaaggaacac aggtggaaaa | ggagtgaact | 1020 |
| atgctctggc | tccaggctcc | cagacctctg | atctgtctct cccagatggt | aaagtgatgg | 1080 | ttcatgaccc tcattctcta gcgtga        1106

<210> SEQ ID NO 44
<211> LENGTH: 1105
<212> TYPE: DNA
<213> ORGANISM: Artificial Sequence
<220> FEATURE:
<223> OTHER INFORMATION: Synthetic polynucleotide

<400> SEQUENCE: 44

| | |
|---|---|
| atggcaccct gcacgctgct cctgctgttg gcggccgccc tggcccccac tcagacccgc | 60 |
| gcgggcccac attcgctgag gtatttcgtc accgccgtgt cccggcccgg cctcggggag | 120 |
| ccccggttca tcgctgtcgg ctacgtggac gacacgcagt tcgtgcgctt cgacagcgac | 180 |
| gcggataatc cgagatttga gccgcgggcg ccgtggatgg agcaggaggg gccggagtat | 240 |
| tgggaggagc agacacagag agccaagagc gatgagcagt ggttccgagt gagcctgagg | 300 |
| accgcacaga gatactacaa ccagagcaag ggcggctctc acacgttcca gcggatgttc | 360 |
| ggctgtgacg tggggtcgga ctggcgcctc ctccgcgggt accagcagtt cgcctacgac | 420 |
| ggccgcgatt acatcgccct gaacgaagac ctgaaaacgt ggacggcggc ggacacggcg | 480 |
| gcgctgatca ccagacgcaa gtgggagcag ctggtgatgc agagttacag ggcctacct | 540 |
| agagggcgag tgcgtggagt ggctccgcag atacctggag ctcggaatg agacgctgct | 600 |
| gcgcacagat tccccaaagg cccatgtgac ctatcacccc agatctcaag ttgatgtcac | 660 |
| cctgaggtgc tgggccctgg gcttctaccc tgctgatatc accctgacct ggcagttgaa | 720 |
| tgggaggac ctgacccagg acatggagct tgtagagacc aggcctgcag gggatggaac | 780 |
| cttccagaag tgggcagctg tggtggtgcc tcttgggaag gagcagaatt acacatgcca | 840 |
| tgtgcaccat aaggggctgc ctgagcctct caccctgaga tggaagcttc ctccatccac | 900 |
| tgtctccaac acggtaatca ttgctgttct ggttgtcctt ggagctgcaa tagtcactgg | 960 |
| agctgtggtg gcttttgtga tgaagatgag aaggaacaca ggtggaaaag gagtgaacta | 1020 |
| tgctctggct ccaggctccc agaccctga tctgtctctc ccagatggta aagtgatggt | 1080 |
| tcatgaccct cattctctag cgtga | 1105 |

<210> SEQ ID NO 45
<211> LENGTH: 1090
<212> TYPE: DNA
<213> ORGANISM: Mus musculus

<400> SEQUENCE: 45

| | |
|---|---|
| atgggggcga tggctccgcg cacgctgctc ctgctgctgg cggccgccct ggccccgact | 60 |
| cagacccgcg cgggcccaca ctcgatgcgg tatttcgaga ccgccgtgtc ccggcccggc | 120 |
| catcgaggag ccccggtaca tctctgtcgg ctatgtggac aacaaggagt tcgtgcgctt | 180 |
| cgacagcgac gcggagaatc cgagatatga gccgcgggcg ccgtggatgg agcaggaggg | 240 |
| gccggagtat tgggagcggg aaacacagaa agccaagggc caagagcagt ggttccgagt | 300 |
| gagcctgagg aacctgctcg gctactacaa ccagagcgcg gcggctctc acacactcca | 360 |
| gcagatgtct ggctgtgact tggggtcgga ctggcgcctc ctccgcgggt acctgcagtt | 420 |
| cgcctatgaa ggccgcgatt acatcgccct gaacgaagac ctgaaaacgt ggacggcggc | 480 |
| ggacatggcg gcgcagatca cccgacgcaa gtgggagcag agtggtgctg cagagcatta | 540 |
| caaggcctac ctggagggcg agtgcgtgga gtggctccac agataccctga gaacgggaa | 600 |

| | |
|---|---|
| cgcgacgctg ctgcgcacag attccccaaa ggcacatgtg acccatcacc ccagatctaa | 660 |
| aggtgaagtc accctgaggt gctgggccct gggcttctac cctgctgaca tcaccctgac | 720 |
| ctggcagttg aatggggagg agctgaccca ggacatggag cttgtggaga ccaggcctgc | 780 |
| aggggatgga accttccaga gtgggcatc tgtggtggtg cctcttggga aggagcagaa | 840 |
| ttacacatgc cgtgtgtacc atgaggggct gcctgagccc ctcaccctga gatgggagcc | 900 |
| tcctccgtcc actgactctt acatggtgat cgttgctgtt ctgggtgtcc ttggagctat | 960 |
| ggccatcatt ggagctgtgg tggcttttgt gatgaagaga aggagaaaca caggtggaaa | 1020 |
| aggaggggac tatgctctgg ctccaggctc ccagagctct gaaatgtctc tccgagattg | 1080 |
| taaagcgtga | 1090 |

<210> SEQ ID NO 46
<211> LENGTH: 1088
<212> TYPE: DNA
<213> ORGANISM: Artificial Sequence
<220> FEATURE:
<223> OTHER INFORMATION: Synthetic polynucleotide

<400> SEQUENCE: 46

| | |
|---|---|
| atgggggcga tggctccgcg cacgctgctc ctgctgctgg cggccgccct ggccccgact | 60 |
| cagacccgcg cgggcccaca ctcgatgcgg tatttcgaga ccgccgtgtc ccggcccggc | 120 |
| ccgaggagcc ccgtacatc tctgtcggct atgtggacaa caaggagttc gtgcgcttcg | 180 |
| acagcgacgc ggagaatccg agatatgagc gcgggcgcc gtggatggag caggaggggc | 240 |
| cggagtattg ggagcgggaa acacagaaag ccaaggccca agagcagtgg ttccgagtga | 300 |
| gcctgaggaa cctgctcggc tactacaacc agagcgcggg cggctctcac acactccagc | 360 |
| agatgtctgg ctgtgacttg gggtcggact ggcgcctcct ccgcgggtac ctgcagttcg | 420 |
| cctatgaagg ccgcgattac atcgccctga cgaagacct gaaaacgtgg acggcggcgg | 480 |
| acatggcggc gcagatcacc cgacgcaagt gggagcagag tggtgctgca gagcattaca | 540 |
| aggcctacct ggagggcgag tgcgtggagt ggctccacag atacctgaag aacgggaacg | 600 |
| cgacgctgct cgcgcacaga tccccaaagg cacatgtgac ccatcacccc agatctaaag | 660 |
| gtgaagtcac cctgaggtgc tgggccctgg cttctaccc tgctgacatc accctgacct | 720 |
| ggcagttgaa tggggaggag ctgacccagg acatggagct gtggagacc aggcctgcag | 780 |
| gggatggaac cttccagaag tgggcatctg tggtggtgcc tcttgggaag gagcagaatt | 840 |
| acacatgccg tgtgtaccat gaggggctgc ctgagcccct caccctgaga tgggagcctc | 900 |
| ctccgtccac tgactcttac atggtgatcg ttgctgttct gggtgtcctt ggagctatgg | 960 |
| ccatcattgg agctgtggtg gcttttgtga tgaagaagag gagaaacaca ggtgaaaag | 1020 |
| gaggggacta tgctctggct ccaggctccc agagctctga atgtctctc cgagattgta | 1080 |
| aagcgtga | 1088 |

<210> SEQ ID NO 47
<211> LENGTH: 1076
<212> TYPE: DNA
<213> ORGANISM: Artificial Sequence
<220> FEATURE:
<223> OTHER INFORMATION: Synthetic polynucleotide

<400> SEQUENCE: 47

| | |
|---|---|
| atgggggcga tggctccgcg cacgctgctc ctgctgctgg cggccgccct ggccccgact | 60 |
| cagacccgcg cgggcccaca ctcgatgcgg tatttcgaga ccgccgtgtc ccggcccggc | 120 |

```
catcgaggag ccccggtaca tctctgtcgg acaaggagtt cgtgcgcttc gacagcgacg      180
cggagaatcc gagatatccg cgggcgccgt ggatggagca ggaggggccg gagtattggg      240
agcgggaaac acagaaagcc aagggccaag agcagtggtt ccgagtgagc ctgaggaacc      300
tgctcggcta ctacaaccag agcgcgggcg gctctcacac actccagcag atgtctggct      360
gtgacttggg gtcggactgg cgcctcctcc gcgggtacct gcagttcgcc tatgaaggcc      420
gcgattacat cgccctgaac gaagacctga aaacgtggac ggcggcggac atggcggcgc      480
agatcacccg acgcaagtgg gagcagagtg gtgctgcaga gcattacaag gcctacctgg      540
agggcgagtg cgtggagtgg ctccacagat acctgaagaa cggaacgcg acgctgctgc       600 gcacagattc cccaaaggca catgtgaccc atcaccccag atctaaaggt gaagtcaccc      660
tgaggtgctg ggccctgggc ttctaccctg ctgacatcac cctgacctgg cagttgaatg      720
gggaggagct gacccaggac atggagcttg tggagaccag gcctgcaggg gatggaacct      780
tccagaagtg ggcatctgtg gtggtgcctc ttgggaagga gcagaattac acatgccgtg      840
tgtaccatga ggggctgcct gagcccctca ccctgagatg ggagcctcct ccgtccactg      900
actcttacat ggtgatcgtt gctgttctgg gtgtccttgg agctatggcc atcattggag      960
ctgtggtggc ttttgtgatg aagagaagga gaaacacagg tggaaaagga ggggactatg     1020
ctctggctcc aggctcccag agctctgaaa tgtctctccg agattgtaaa gcgtga         1076

<210> SEQ ID NO 48
<211> LENGTH: 792
<212> TYPE: DNA
<213> ORGANISM: Mus musculus

<400> SEQUENCE: 48
atggctctgc agatccccag cctcctcctc tcggctgctg tggtggtgct gatggtgctg       60
agcagcccag ggactgaggg cggagactcc gaaaggcatt tcgtgcacca gttcaagggc      120
gagtgctact tcaccaacgg gacgcagcgc atacggctcg tgaccagata catctacaac      180
cgggaggagt acctgcgctt cgacagcgac gtgggcgagt accgcgcggt gaccgagctg      240
gggcggcact cagccgagta ctacaataag cagtacctgg agcgaacgcg ggccgagctg      300
gacacggcgt gcagacacaa ctacgaggag acggaggtcc ccacctccct gcggcggctt      360
gaacagccca atgtcgccat ctccctgtcc aggacagagg ccctcaacca ccacaacact      420
ctggtctgtt cggtgacaga tttctaccca gccaagatca agtgcgctg gttcaggaat       480 ggccaggagg agacagtggg ggtctcatcc acacagctta ttaggaatgg ggactggacc      540
ttccaggtcc tggtcatgct ggagatgacc cctcatcagg gagaggtcta cacctgccat      600
gtggagcatc ccagcctgaa gagccccatc actgtggagt ggagggcaca gtccgagtct      660 gccccggagca agatgttgag cggcatcggg ggctgcgtgc ttggggtgat cttcctcggg      720
ctcggccttt tcatccgtca caggagtcag aaaggacctc gaggccctcc tccagcaggg      780
ctcctgcagt ga                                                          792

<210> SEQ ID NO 49
<211> LENGTH: 771
<212> TYPE: DNA
<213> ORGANISM: Mus musculus

<400> SEQUENCE: 49
atgccgtgca gcagagctct gattctgggg gtcctcgccc tgaacaccat gctcagcctc       60
```

-continued

| | |
|---|---|
| tgcggaggtg aagacgacat tgaggccgac cacgtaggct tctatggtac aactgtttat | 120 |
| cagtctcctg gagacattgg ccagtacaca catgaatttg atggtgatga gttgttctat | 180 |
| gtggacttgg ataagaagaa aactgtctgg aggcttcctg agtttggcca attgatactc | 240 |
| tttgagcccc aaggtggact gcaaaacata gctgcagaaa acacaacttt gggaatcttg | 300 |
| actaagaggt caaatttcac cccagctacc aatgaggctc ctcaagcgac tgtgttcccc | 360 |
| aagtcccctg tgctgctggg tcagcccaac acccttatct gctttgtgga caacatcttc | 420 |
| ccacctgtga tcaacatcac atggctcaga aatagcaagt cagtcacaga cggcgtttat | 480 |
| gagaccagct tcctcgtcaa ccgtgaccat tccttccaca agctgtctta tctcaccttc | 540 |
| atcccttctg atgatgacat ttatgactgc aaggtggagc actggggcct ggaggagccg | 600 |
| gttctgaaac actgggaacc tgagattcca gccccatgt cagagctgac agaaactgtg | 660 |
| gtgtgtgccc tggggttgtc tgtgggcctt gtgggcatcg tggtgggcac catcttcatc | 720 |
| attcaaggcc tgcgatcagg tggcacctcc agacacccag ggcctttatg a | 771 |

<210> SEQ ID NO 50
<211> LENGTH: 611
<212> TYPE: DNA
<213> ORGANISM: Artificial Sequence
<220> FEATURE:
<223> OTHER INFORMATION: Synthetic polynucleotide

<400> SEQUENCE: 50

| | |
|---|---|
| atggctctgc agatccccag cctcctcctc tcggctgctg tggtggtgct gatggtgctg | 60 |
| agcagcccag ggactgaggg cggagactcc gaaaggcatt tcgtgcacca gttcaagggc | 120 |
| gagtgctact tcaccaacgg gacgcagcgc cggaggtccc cacctccctg cggcggcttg | 180 |
| aacagcccaa tgtcgccatc tccctgtcca ggacagaggc cctcaaccac cacaacactc | 240 |
| tggtctgttc ggtgacagat ttctacccag ccaagatcaa agtgcgctgg ttcaggaatg | 300 |
| gccaggagga gacagtgggg gtctcatcca cacagcttat taggaatggg gactggacct | 360 |
| tccaggtcct ggtcatgctg gagatgaccc ctcatcaggg agaggtctac acctgccatg | 420 |
| tggagcatcc cagcctgaag agccccatca ctgtggagtg gagggcacag tccgagtctg | 480 |
| cccggagcaa gatgttgagc ggcatcgggg gctgcgtgct tggggtgatc ttcctcgggc | 540 |
| tcggcctttt catccgtcac aggagtcaga aaggacctcg aggccctcct ccagcagggc | 600 |
| tcctgcagtg a | 611 |

<210> SEQ ID NO 51
<211> LENGTH: 1098
<212> TYPE: DNA
<213> ORGANISM: Artificial Sequence
<220> FEATURE:
<223> OTHER INFORMATION: Synthetic polynucleotide

<400> SEQUENCE: 51

| | |
|---|---|
| atggccgtca tggcgccccg aaccctcgtc ctgctactct cgggggctct ggccctgacc | 60 |
| cagacctggg cgggctctca ctccatgagg tatttcttca catccgtgtc ccggccggc | 120 |
| cgcggggagc ccgcttcat cgcagtgggc tacgtggacg acacgcagtt cgtgcggttc | 180 |
| gacagcgacg ccgcgagcca gaggatggag ccgcgggcgc cgtggataga gcaggagggt | 240 |
| ccggagtatt gggacgggga gacacggaaa gtgaaggccc actcacagac tcaccgagtg | 300 |
| gacctgggga ccctgcgcgg ctactacaac cagagcgagg ccggttctca caccgtccag | 360 |
| aggatgtatg gctgcgacgt ggggtcggac tggcgcttcc tccgcgggta ccaccagtac | 420 |

```
gcctacgacg gcaaggatta catcgccctg aaagaggacc tgcgctcttg gaccgcggcg     480
gacatggcag ctcagaccac caagcacaag tgggaggcgg cccatgtggc ggagcagttg     540
agagcctacc tggagggcac gtgcgtggag tggctccgca gatacctgga gaacgggaag     600
gagacgctgc agcgcacgga cgcccccaaa acgcatatga ctcaccacgc tgtctctgac     660
catgaagcca ccctgaggtg ctgggccctg agcttctacc ctgcggagat cacactgacc     720
tggcagcggg atggggagga ccagacccag gacacggagc tcgtggagac caggcctgca     780
ggggatggaa ccttccagaa gtgggcggct gtggtggtgc cttctggaca ggagcagaga     840
tacacctgcc atgtgcagca tgagggtttg cccaagcccc tcaccctgag atgggagccg     900
tcttcccagc ccaccatccc catcgtgggc atcattgctg gcctggttct ctttggagct     960
gtgatcactg gagctgtggt cgctgctgtg atgtggagga ggaagagctc agatagaaaa     1020
ggagggagct actctcaggc tgcaagcagt gacagtgccc agggctctga tgtgtctctc     1080
acagcttgta aagtgtga                                                   1098
```

<210> SEQ ID NO 52
<211> LENGTH: 1089
<212> TYPE: DNA
<213> ORGANISM: Artificial Sequence
<220> FEATURE:
<223> OTHER INFORMATION: Synthetic polynucleotide

<400> SEQUENCE: 52

```
atgctggtca tggcgccccg aaccgtcctc ctgctgctct cggcggccct ggccctgacc      60
gagacctggg ccggctccca ctccatgagg tatttctaca cctccgtgtc ccggcccggc     120
cgcggggagc cccgcttcat ctcagtgggc tacgtggacg acacgcagtt cgtgaggttc     180
gacagcgacg ccgcgagtcc gagagaggag ccgcgggcgc cgtggataga gcaggagggg     240
ccggaatatt gggaccggaa cacacagatc tgcaagacca cacacagac tgaccgagag     300 agcctgcgga acctgcgcgg ctactacaac cagagcgagg ccgggtctca cacttggcag     360
acgatgtacg gctgcgacgt ggggccggac gggcgcctcc tccgcgggca taaccagttc     420
gcctacgacg gcaaggatta catcgccctg aacgaggacc tgagctcctg gaccgcggcg     480
gacaccgcgg ctcagatcac ccagcgcaag tgggaggcgg cccgtgtggc ggagcagctg     540
agaacctacc tggagggcac gtgcgtggag tggctccgca gatacctgga gaacgggaag     600
gagacgctgc agcgcgcgga ccccccaaag acacatgtga cccaccaccc catctctgac     660
catgaggcca ccctgaggtg ctgggccctg gcttctacc ctgcggagat cacactgacc     720
tggcagcggg atggcgagga ccaaactcag gacaccgagc ttgtggagac cagaccagca     780
ggagacagaa ccttccagaa gtgggcagct gtggtggtgc cttctggaga agagcagaga     840
tacacatgcc atgtacagca tgagggggctg ccgaagcccc tcaccctgag atgggagcca     900
tcttcccagt ccaccgtccc catcgtgggc attgttgctg gctggctgt cctagcagtt     960 gtggtcatcg gagctgtggt cgctgctgtg atgtgtagga ggaagagttc aggtggaaaa    1020
ggagggagct actctcaggc tgcgtccagc gacagtgccc agggctctga tgtgtctctc    1080
acagcttga                                                            1089
```

<210> SEQ ID NO 53
<211> LENGTH: 768
<212> TYPE: DNA
<213> ORGANISM: Artificial Sequence
<220> FEATURE:

<223> OTHER INFORMATION: Synthetic polynucleotide

<400> SEQUENCE: 53

```
atgatcctaa acaaagctct gatgctgggg ccctcgccc tgaccaccgt gatgagccct    60
tgtggaggtg aagacattgt ggctgaccat gttgcctctt acggtgtaaa cttgtaccag   120
tcttatggtc cctctgggca gtacagccat gaatttgatg gagacgagga gttctatgtg   180
gacctggaga ggaaggagac tgtctggcag ttgcctctgt tccgcagatt tagaagattt   240
gacccgcaat ttgcactgac aaacatcgct gtgctaaaac ataacttgaa catcgtgatt   300
aaacgctcca actctaccgc tgctaccaat gaggttcctg aggtcacagt gttttccaag   360
tctcccgtga cactgggtca gcccaacacc ctcatctgtc ttgtggacaa catctttcct   420
cctgtggtca acatcacctg gctgagcaat gggcactcag tcacagaagg tgtttctgag   480
accagcttcc tctccaagag tgatcattcc ttcttcaaga tcagttacct caccttcctc   540
ccttctgctg atgagattta tgactgcaag gtggagcact ggggcctgga tgagcctctt   600
ctgaaacact gggagcctga gattccaaca cctatgtcag agctcacaga gactgtggtc   660
tgcgccctgg ggttgtctgt gggcctcgtg gcattgtgg tggggaccgt cttgatcatc   720
cgaggcctgc gttcagttgg tgcttccaga caccaagggc ccttgtga              768
```

<210> SEQ ID NO 54
<211> LENGTH: 786
<212> TYPE: DNA
<213> ORGANISM: Artificial Sequence
<220> FEATURE:
<223> OTHER INFORMATION: Synthetic polynucleotide

<400> SEQUENCE: 54

```
atgtcttgga agaaggcttt gcggatccct ggaggccttc gggtagcaac tgtgaccttg    60
atgctggcga tgctgagcac cccggtggct gagggcagag actctcccga ggatttcgtg   120
taccagttta agggcatgtg ctacttcacc aacgggacgg agcgcgtgcg tcttgtgacc   180
agatacatct ataaccgaga ggagtacgca cgcttcgaca gcgacgtggg ggtgtatcgg   240
gcggtgacgc cgctgggggcc gcctgccgcc gagtactgga acagccagaa ggaagtcctg   300
gagaggaccc gggcggagtt ggacacggtg tgcagacaca actaccagtt ggagctccgc   360
acgaccttgc agcggcgagt ggagcccaca gtgaccatct ccccatccag acagaggcc   420
ctcaaccacc acaacctgct ggtctgctca gtgacagatt tctatccagc ccagatcaaa   480
gtccggtggt tcggaatga ccaggaggag acaactggcg ttgtgtccac ccccttatt    540
aggaacggtg actggacctt ccagatcctg gtgatgctgg aaatgactcc ccagcgtgga   600
gacgtctaca cctgccacgt ggagcacccc agcctccaga cccccatcat cgtggagtgg   660
cgggctcagt ctgaatctgc ccagagcaag atgctgagtg gcattggagg cttcgtgctg   720
gggctgatct tcctcgggct gggccttatt atccatcaca ggagtcagaa agggctcctg   780
cactga                                                              786
```

<210> SEQ ID NO 55
<211> LENGTH: 801
<212> TYPE: DNA
<213> ORGANISM: Artificial Sequence
<220> FEATURE:
<223> OTHER INFORMATION: Synthetic polynucleotide

<400> SEQUENCE: 55

```
atggtgtgtc tgaggctccc tggaggctcc tgcatggcag ttctgacagt gacactgatg    60
```

| | | |
|---|---|---|
| gtgctgagct ccccactggc tttggctggg acaccagac cacgtttctt ggagtactct | 120 | |
| acgtctgagt gtcatttctt caatgggacg gagcgggtgc ggtacctgga cagatacttc | 180 | |
| cataaccagg aggagaacgt gcgcttcgac agcgacgtgg gggagttccg ggcggtgacg | 240 | |
| gagctggggc ggcctgatgc cgagtactgg aacagccaga aggacctcct ggagcagaag | 300 | |
| cggggccggg tggacaacta ctgcagacac aactacgggg ttgtggagag cttcacagtg | 360 | |
| cagcggcgag tccatcctaa ggtgactgtg tatccttcaa agacccagcc cctgcagcac | 420 | |
| cataacctcc tggtctgttc tgtgagtggt ttctatccag gcagcattga agtcaggtgg | 480 | |
| ttccggaatg gccaggaaga gaagactggg gtggtgtcca caggcctgat ccacaatgga | 540 | |
| gactggacct tccagaccct ggtgatgctg gaaacagttc ctcggagtgg agaggtttac | 600 | |
| acctgccaag tggagcaccc aagcgtgaca agccctctca cagtggaatg gagagcacgg | 660 | |
| tctgaatctg cacagagcaa gatgctgagt ggagtcgggg gctttgtgct gggcctgctc | 720 | |
| ttccttgggg ccgggctgtt catctacttc aggaatcaga aggacactc tggacttcag | 780 | |
| ccaagaggat tcctgagctg a | 801 | |

<210> SEQ ID NO 56
<211> LENGTH: 801
<212> TYPE: DNA
<213> ORGANISM: Artificial Sequence
<220> FEATURE:
<223> OTHER INFORMATION: Synthetic polynucleotide

<400> SEQUENCE: 56

| | | |
|---|---|---|
| atggtgtgtc tgaagttccc tggaggctcc tgcatggcag ctctgacagt gacactgatg | 60 | |
| gtgctgagct ccccactggc tttggctggg acacccgac cacgtttctt ggagcaggtt | 120 | |
| aaacatgagt gtcatttctt caacgggacg gagcgggtgc ggttcctgga cagatacttc | 180 | |
| tatcaccaag aggagtacgt gcgcttcgac agcgacgtgg gggagtaccg ggcggtgacg | 240 | |
| gagctggggc ggcctgatgc cgagtactgg aacagccaga aggacctcct ggagcagaag | 300 | |
| cgggccgcgg tggacaccta ctgcagacac aactacgggg ttggtgagag cttcacagtg | 360 | |
| cagcggcgag tctatcctga ggtgactgtg tatcctgcaa agacccagcc cctgcagcac | 420 | |
| cacaacctcc tggtctgctc tgtgaatggt ttctatccag gcagcattga agtcaggtgg | 480 | |
| ttccggaacg gccaggaaga gaagactggg gtggtgtcca caggcctgat ccagaatgga | 540 | |
| gactggacct tccagaccct ggtgatgctg gaaacagttc ctcggagtgg agaggtttac | 600 | |
| acctgccaag tggagcaccc aagcctgacg agccctctca cagtggaatg gagagcacgg | 660 | |
| tctgaatctg cacagagcaa gatgctgagt ggagtcgggg gcttcgtgct gggcctgctc | 720 | |
| ttccttgggg ccgggctgtt catctacttc aggaatcaga aggacactc tggacttcag | 780 | |
| ccaacaggat tcctgagctg a | 801 | |

<210> SEQ ID NO 57
<211> LENGTH: 765
<212> TYPE: DNA
<213> ORGANISM: Artificial Sequence
<220> FEATURE:
<223> OTHER INFORMATION: Synthetic polynucleotide

<400> SEQUENCE: 57

| | | |
|---|---|---|
| atgatcctaa acaaagctct gatgctgggg gcccttgccc tgaccaccgt gatgagcccc | 60 | |
| tgtggaggtg aagacattgt ggctgaccac gtcgcctctt atggtgtaaa cttgtaccag | 120 | |

```
tcttacggtc cctctggcca gtacacccat gaatttgatg gagatgagca gttctacgtg    180
gacctgggga ggaaggagac tgtctggtgt ttgcctgttc tcagacaatt tagatttgac    240
ccgcaatttg cactgacaaa catcgctgtc ctaaaacata acttgaacag tctgattaaa    300
cgctccaact ctaccgctgc taccaatgag gttcctgagg tcacagtgtt ttccaagtct    360
cccgtgacac tgggtcagcc caacatcctc atctgtcttg tggacaacat ctttcctcct    420
gtggtcaaca tcacatggct gagcaatggg cactcagtca cagaaggtgt ttctgagacc    480
agcttcctct ccaagagtga tcattccttc ttcaagatca gttacctcac cctcctccct    540
tctgctgagg agagttatga ctgcaaggtg gagcactggg gcctggacaa gcctcttctg    600
aaacactggg agcctgagat tccagcccct atgtcagagc tcacagagac tgtggtctgc    660
gccctgggat tgtctgtggg cctcgtgggc attgtggtgg gcactgtctt catcatccga    720
ggcctgcgtt cagttggtgc ttccagacac caagggccct tgtga                    765

<210> SEQ ID NO 58
<211> LENGTH: 786
<212> TYPE: DNA
<213> ORGANISM: Artificial Sequence
<220> FEATURE:
<223> OTHER INFORMATION: Synthetic polynucleotide

<400> SEQUENCE: 58
atgtcttgga aaaggctttt gcggatcccc ggaggccttc gggcagcaac tgtgaccttg     60
atgctgtcga tgctgagcac cccagtggct gagggcagag actctcccga ggatttcgtg    120
taccagttta agggcatgtg ctacttcacc aacgggacag agcgcgtgcg tcttgtgagc    180
agaagcatct ataaccgaga agagatcgtg cgcttcgaca gcgacgtggg ggagttccgg    240
gcggtgacgc tgctggggct gcctgccgcc gagtactgga acagccagaa ggacatcctg    300
gagaggaaac gggcggcggt ggacagggtg tgcagacaca actaccagtt ggagctccgc    360
acgaccttgc agcggcgagt ggagcccaca gtgaccatct ccccatccag gacagaggcc    420
ctcaaccacc acaacctgct ggtctgctcg gtgacagatt tctatccagc ccagatcaaa    480
gtccggtggt tcggaatga ccaggaggag acagctggcg ttgtgtccac ccccttatt    540 aggaatggtg actggacctt ccagatcctg gtgatgctgg aaatgactcc ccagcgtgga    600
gacgtctaca cctgccacgt ggagcacccc agcctccaga gccccatcac cgtggagtgg    660
cgggctcaat ctgaatctgc ccagagcaag atgctgagtg gcattggagg cttcgtgctg    720
gggctgatct tcctcgggct gggccttatc atccatcaca ggagtcagaa agggctcctg    780
cactga                                                               786

<210> SEQ ID NO 59
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 59
gtcccggccc ggcccgagga gcc                                             23

<210> SEQ ID NO 60
<211> LENGTH: 23
<212> TYPE: DNA
<213> ORGANISM: Artificial Sequence
<220> FEATURE:
<223> OTHER INFORMATION: Synthetic polynucleotide
```

<400> SEQUENCE: 60
ggtgatgcag agttacaggg cct                                    23

<210> SEQ ID NO 61
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 61
acatctctgt cggacaagga gttcgtgcgc                             30

<210> SEQ ID NO 62
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 62
gatatccgcg ggcgccgtgg atg                                    23

<210> SEQ ID NO 63
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 63
ataatccgag atttgaccgc ggc                                    23

<210> SEQ ID NO 64
<211> LENGTH: 61
<212> TYPE: DNA
<213> ORGANISM: Artificial Sequence
<220> FEATURE:
<223> OTHER INFORMATION: Synthetic polynucleotide

<400> SEQUENCE: 64
tacaaccggg aggagtacct gcgcttcgac agcgacgtgg gcgacgtacc gcgcggtgac    60
c                                                                   61

<210> SEQ ID NO 65
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 65
atgttggccc tcctcatgga cgcgaagctg tcgctgcacc cgctcatggc gcgccactgg    60

<210> SEQ ID NO 66
<211> LENGTH: 48
<212> TYPE: DNA
<213> ORGANISM: Artificial Sequence
<220> FEATURE:
<223> OTHER INFORMATION: Synthetic polynucleotide

<400> SEQUENCE: 66
gacacaacta cgaggagacg gaggtcccca cctccctgcg gcggcttg              48

```
<210> SEQ ID NO 67
<211> LENGTH: 48
<212> TYPE: DNA
<213> ORGANISM: Artificial Sequence
<220> FEATURE:
<223> OTHER INFORMATION: Synthetic polynucleotide

<400> SEQUENCE: 67
ctgtgttgat gctcctctgc ctccaggggt ggagggacgc cgccgaac            48
```